(12) United States Patent
Kawamura et al.

(10) Patent No.: US 7,425,654 B2
(45) Date of Patent: Sep. 16, 2008

(54) AROMATIC TRIAMINE COMPOUND AND ORGANIC ELECTROLUMINESCENCE DEVICE USING THE SAME

(75) Inventors: Masahiro Kawamura, Chiba (JP); Nobuhiro Yabunouchi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/341,375

(22) Filed: Jan. 30, 2006

(65) Prior Publication Data

US 2006/0232198 A1 Oct. 19, 2006

(30) Foreign Application Priority Data

Apr. 18, 2005 (JP) ............................. 2005-119910

(51) Int. Cl.
*C07C 211/54* (2006.01)

(52) U.S. Cl. ...................................... 564/434; 428/917

(58) Field of Classification Search ........................ None
See application file for complete search history.

(56) References Cited

U.S. PATENT DOCUMENTS 6,541,129 B1 * 4/2003 Kawamura et al. .......... 428/690

2003/0143430 A1 * 7/2003 Kawamura et al. .......... 428/690

FOREIGN PATENT DOCUMENTS

| JP | 9-301934 | 11/1997 |
|---|---|---|
| JP | 10-265773 | 10/1998 |
| JP | 11-219787 | 8/1999 |

OTHER PUBLICATIONS

Meng-Yen Chou, et al., "Electropolymerization of Starburst Triarylamines and Their Application to Electrochromism and Electroluminescence", Chem. Mater., vol. 16, No. 4, 2004, pp. 654-661.
U.S. Appl. No. 11/411,141, filed Apr. 26, 2006, Kawamura, et al.
U.S. Appl. No. 11/362,159, filed Feb. 27, 2006, Kawamura, et al.
U.S. Appl. No. 11/576,892, filed Apr. 9, 2007, Kawamura, et al.

* cited by examiner

*Primary Examiner*—Brian J Davis
(74) *Attorney, Agent, or Firm*—Oblon, Spivak, McClelland, Maier & Neustadt, P.C.

(57) ABSTRACT

Provided are an aromatic triamine compound of a specific structure having at least one terphenyl structure and an organic electroluminescence device in which an organic thin film layer comprising a single layer or plural layers having at least a luminescent layer is interposed between a cathode and an anode, wherein at least one layer of the above organic thin film layers contains the aromatic triamine compound described above in the form of a single component or a mixed component, and provided are the organic electroluminescence device having a high luminous efficiency and a long life and the novel aromatic triamine compound for materializing the same.

6 Claims, 8 Drawing Sheets

AROMATIC TRIAMINE COMPOUND AND ORGANIC ELECTROLUMINESCENCE DEVICE USING THE SAME

BACKGROUND OF THE INVENTION

Figure 1:
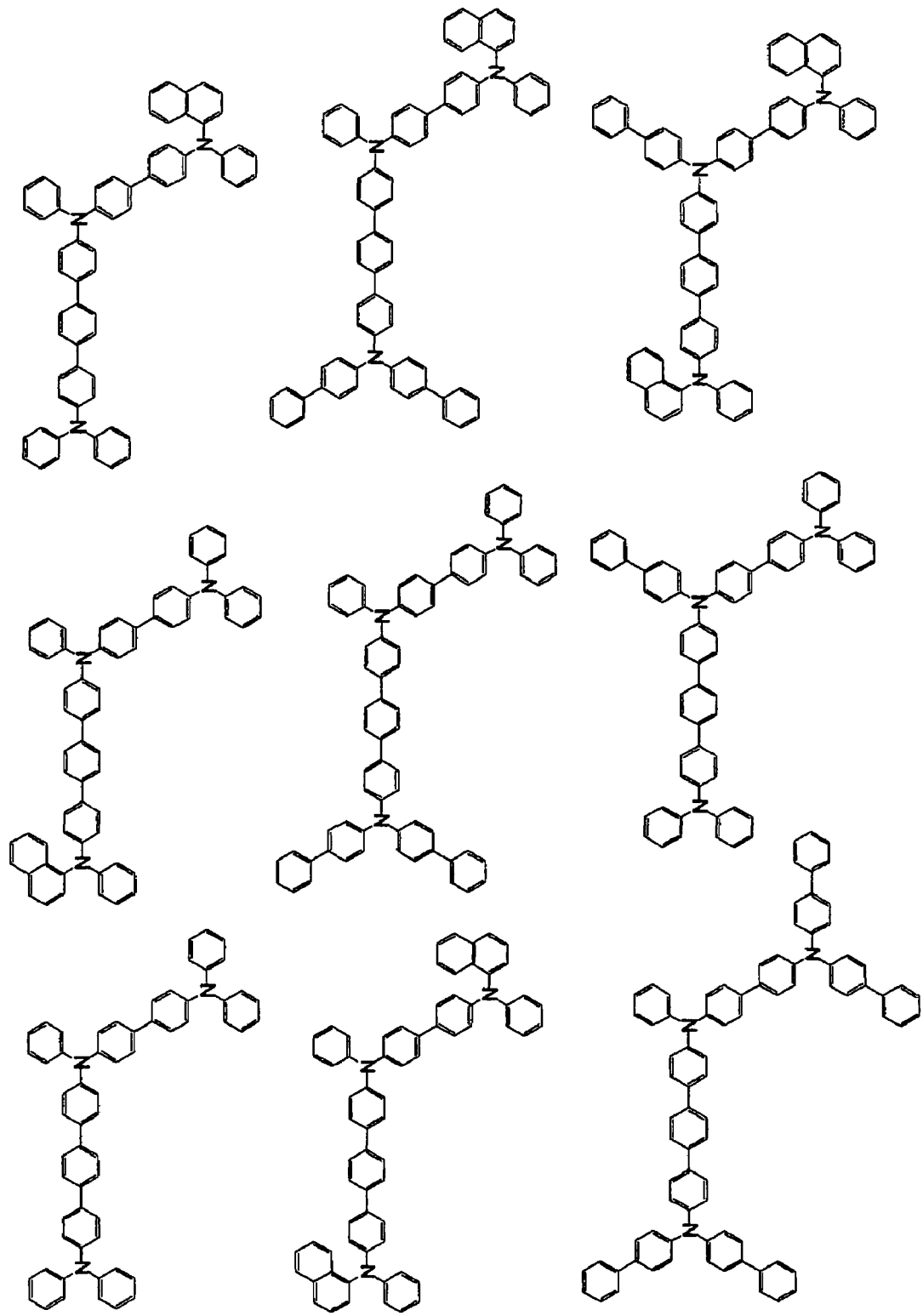

The present invention relates to an aromatic triamine compound and an organic electroluminescence device using the same, specifically to an organic electroluminescence device which is excellent in a hole injecting property and which has a high luminous efficiency and a long life and a novel aromatic triamine compound which materializes the same.

RELATED ART

An organic electroluminescence (EL) device is a spontaneous luminescent device making use of the principle that a fluorescent substance emits light by recombination energy of holes injected from an anode and electrons injected from a cathode by applying an electric field. Since a low voltage-driven organic EL device of a laminate type was reported by C. W. Tang of Eastman Kodak Company (C. W. Tang and S. A. Vanslyke, Applied Physics Letters, Vol. 51, p. 913, 1987), researches on organic EL devices comprising organic materials as structural materials have actively been carried out. Tang et al. use tris(8-hydroxyquinolinol)aluminum for the luminescent layer and a triphenyldiamine derivative for the hole transporting layer. The advantages of a laminate structure include a rise in an efficiency of holes injected into a luminescent layer, an improvement in a forming efficiency of excitons formed by blocking electrons injected from a cathode to recombine them and shutting up of excitons formed in a luminescent layer. As shown in the above example, a two layer type comprising a hole transporting (injecting) layer and an electron transporting luminescent layer and a three layer type comprising a hole transporting (injecting) layer, a luminescent layer and an electron transporting (injecting) layer are well known as the device structure of the organic EL device. In such laminate type structural device, a device structure, a forming method and structural components are studied in order to enhance a recombination efficiency of holes and electrons injected.

Aromatic diamine derivatives described in a patent document 1 and aromatic condensed ring diamine derivatives described in a patent document 2 have so far been known as a hole transporting material used for an organic EL device, and disclosed as those obtained by improving the above compounds are a triamine compound represented by the following Formula (A) in a patent document 3, an organic triamine compound represented by the following Formula (B) in a patent document 4 and a terphenylenediamine compound represented by the following Formula (C) in a patent document 5:

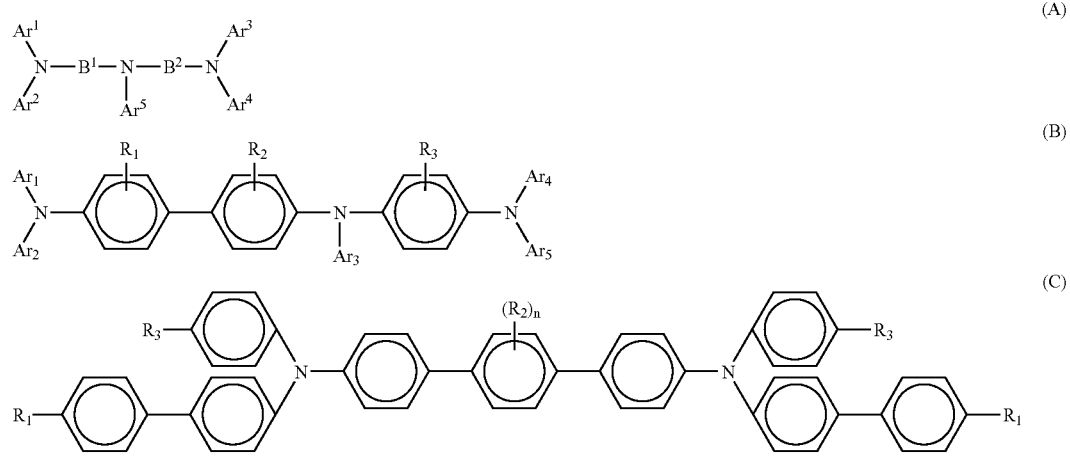

in Formula (A), $B^1$ and $B^2$ each represent a substituted or unsubstituted biphenylene group which is independently selected, and $Ar^1$, $Ar^2$, $Ar^3$, $Ar^4$ and $Ar^5$ each represent a hydrogen atom, a substituted or unsubstituted biphenylene group or an aryl group which is independently selected;

in Formula (B), $Ar^1$, $Ar^2$, $Ar^3$, $Ar^4$ and $Ar^5$ each represent independently an alkyl group which may have a substituent, an aralkyl group, an aryl group, a biphenyl group or a heterocyclic group, and $R^1$, $R^2$ and $R^3$ each represent independently a hydrogen atom, an alkoxy group or a halogen atom; and in Formula (C), $R^1$ is a hydrogen atom or methyl; $R^2$ is a hydrogen atom or methyl; n is 1 or 2; and $R^3$ is a hydrogen atom, methoxy or a phenyl group in which a p-position may be substituted with methyl.

However, devices in which the above compounds are used for a hole injecting and transporting layer are not satisfactory in a life, a driving voltage and a luminous efficiency, and organic EL devices having a lower driving voltage, a higher luminous efficiency and a longer life are desired.

Patent document 1: U.S. Pat. No. 4,720,432
Patent document 2: U.S. Pat. No. 5,061,569
Patent document 3: JP. Patent 3565870
Patent document 4: JP. Patent 3220867
Patent document 5: JP. Patent 3398548

DISCLOSURE OF THE INVENTION

The present invention has been made in order to solve the problems described above, and an object thereof is to provide an organic EL device which is excellent in a hole injecting property and which has a high luminous efficiency and a long life and a novel aromatic triamine compound which materializes the same.

Intensive researches repeated by the present inventors in order to achieve the object described above have resulted in finding that the object described above is achieved by an aromatic triamine compound of a specific structure having at least one terphenyl structure, and thus they have come to complete the present invention.

That is, the present invention provides an aromatic triamine compound represented by the following Formula (1):

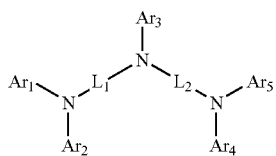

(1)

wherein $Ar_1$ to $Ar_5$ each are independently a substituted or unsubstituted aryl group having 6 to 30 nuclear carbon atoms; and $L_1$ and $L_2$ each are independently a linkage group having 6 to 30 nuclear carbon atoms which has one or more benzene rings, and at least one of $L_1$ and $L_2$ is a substituted or unsubstituted terphenylene group.

Further, the present invention provides an organic EL device in which an organic thin film layer comprising a single layer or plural layers having at least a luminescent layer is interposed between a cathode and an anode, wherein at least one layer of the above organic thin film layers contains the aromatic triamine compound described above in the form of a single component or a mixed component.

An organic EL device using the aromatic triamine compound of the present invention is excellent in a hole injecting property and has a high luminous efficiency and a long life.

BEST MODE FOR CARRYING OUT THE INVENTION

The aromatic triamine compound of the present invention is a compound represented by the following Formula (1):

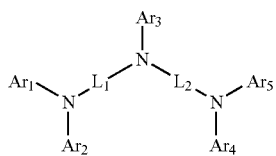

(1)

In Formula (1), $Ar_1$ to $Ar_5$ each are independently a substituted or unsubstituted aryl group having 6 to 30 nuclear carbon atoms (preferably 6 to 20 nuclear carbon atoms).

The aryl group represented by $Ar_1$ to $Ar_5$ described above include, for example, phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl) phenyl, 3-methyl-2-naphthyl, 4-methyl-1-naphthyl, 4-methyl-1-anthryl, 4'-methylbiphenylyl, 4"-t-butyl-p-terphenyl-4-yl and fluorenyl.

Among them, phenyl, naphthyl, biphenylyl, anthranyl, phenanthryl, pyrenyl, chrysenyl and fluorenyl are preferred, and phenyl and naphthyl are particularly preferred.

A substituent for the aryl group described above includes, for example, an alkyl group (having preferably 1 to 20 carbon atoms, more preferably 1 to 12 carbon atoms and particularly preferably 1 to 8 carbon atoms and including, for example, methyl, ethyl, iso-propyl, tert-butyl, n-octyl, n-decyl, n-hexadecyl, cyclopropyl, cyclopentyl and cyclohexyl), an aryl group (having preferably 6 to 30 nuclear carbon atoms, more preferably 6 to 20 nuclear carbon atoms and including, for example, phenyl, naphthyl, biphenylyl, anthranyl, phenanthryl, pyrenyl, pyrenyl, chrysenyl and fluorenyl), an alkenyl group (having preferably 2 to 20 carbon atoms, more preferably 2 to 12 carbon atoms and particularly preferably 2 to 8 carbon atoms and including, for example, vinyl, allyl, 2-butenyl and 3-pentenyl), an alkynyl group (having preferably 2 to 20 carbon atoms, more preferably 2 to 12 carbon atoms and particularly preferably 2 to 8 carbon atoms and including, for example, propargyl and 3-pentynyl), an amino group (having preferably 0 to 20 carbon atoms, more preferably 0 to 12 carbon atoms and particularly preferably 0 to 6 carbon atoms and including, for example, amino, methylamino, dimethylamino, diethylamino, diphenylamino and dibenzylamino), an alkoxy group (having preferably 1 to 20 carbon atoms, more preferably 1 to 12 carbon atoms and particularly preferably 1 to 8 carbon atoms and including, for example, methoxy, ethoxy and butoxy), an aryloxy group (having preferably 6 to 20 carbon atoms, more preferably 6 to 16 carbon atoms and particularly preferably 6 to 12 carbon atoms and including, for example, phenyloxy and 2-naphthyloxy), an acyl group (having preferably 1 to 20 carbon atoms, more preferably 1 to 16 carbon atoms and particularly preferably 1 to 12 carbon atoms and including, for example, acetyl, benzoyl, formyl and pivaloyl), an alkoxycarbonyl group (having preferably 2 to 20 carbon atoms, more preferably 2 to 16 carbon atoms and particularly preferably 2 to 12 carbon atoms and including, for example, methoxycarbonyl and ethoxycarbonyl), an aryloxycarbonyl group (having preferably 7 to 20 carbon atoms, more preferably 7 to 16 carbon atoms and particularly preferably 7 to 10 carbon atoms and including, for example, phenyloxycarbonyl and the like), an acyloxy group (having preferably 2 to 20 carbon atoms, more preferably 2 to 16 carbon atoms and particularly preferably 2 to 10 carbon atoms and including, for example, acetoxy and benzoyloxy), an acylamino group (having preferably 2 to 20 carbon atoms, more preferably 2 to 16 carbon atoms and particularly preferably 2 to 10 carbon atoms and including, for example, acetylamino and benzoylamino), an alkoxycarbonylamino group (having preferably 2 to 20 carbon atoms, more preferably 2 to 16 carbon atoms and particularly preferably 2 to 12 carbon atoms and including, for example, methoxycarbonylamino and the like), an aryloxycarbonylamino group (having preferably 7 to 20 carbon atoms, more preferably 7 to 16 carbon atoms and particularly preferably 7 to 12 carbon atoms and including, for example, phenyloxycarbonylamino and the like), a sulfonylamino group (having preferably 1 to 20 carbon atoms, more preferably 1 to 16 carbon atoms and particularly preferably 1 to 12 carbon atoms and including, for example, methanesulfonylamino and benzenesulfonylamino), a sulfamoyl group (having preferably 0 to 20 carbon atoms, more preferably 0 to 16 carbon atoms and particularly preferably 0 to 12 carbon atoms and including, for example, sulfamoyl, methylsulfamoyl, dimethylsulfamoyl and, phenylsulfamoyl), a carbamoyl group (having preferably 1 to 20 carbon atoms, more preferably 1 to 16 carbon atoms and particularly preferably 1 to 12 carbon atoms and including, for example, carbamoyl, methylcarbamoyl, diethylcarbamoyl and, phenylcarbamoyl), an alkylthio group (having preferably 1 to 20 carbon atoms, more preferably 1 to 12 carbon atoms and particularly preferably 1 to 8 carbon atoms and including, for example, methylthio and ethylthio), an arylthio group (having preferably 6 to 20 carbon atoms, more preferably 6 to 16 carbon atoms and particularly preferably 6 to 12 carbon atoms and including, for example, phenylthio and the like), a sulfonyl group (having preferably 1 to 20 carbon atoms, more preferably 1 to 16 carbon atoms and particularly preferably 1 to 12 carbon atoms and including, for example, mesyl and tosyl), a sulfinyl group (having preferably 1 to 20 carbon atoms, more preferably 1 to 16 carbon atoms and particularly preferably 1 to 12 carbon atoms and including, for example, methanesulfinyl and benzenesulfinyl), a ureido group (having preferably 1 to 20 carbon atoms, more preferably 1 to 16 carbon atoms and particularly preferably 1 to 12 carbon atoms and including, for example, ureido, methylureido and phenylureido), a phosphoramide group (having preferably 1 to 20 carbon atoms, more preferably 1 to 16 carbon atoms and particularly preferably 1 to 12 carbon atoms and including, for example, diethylphosphoramide and phenylphosphoramide), a hydroxy group, a mercapto group, a halogen atom (for example, a fluorine atom, a chlorine atom, a bromine atom and an iodine atom), a cyano group, a sulfo group, a carboxyl group, a nitro group, a hydroxamic acid, a sulfino group, a hydrazine group, an imino group, a heterocyclic group (having preferably 1 to 30 carbon atoms, more preferably 1 to 12 carbon atoms, containing, for example, a nitrogen atom, an oxygen atom and a sulfur atom as a hetero atom and including, for example, imidazolyl, pyridyl, quinolyl, furyl, thienyl, piperidyl, morpholino, benzoxazolyl, benzimidazolyl, benzothiazolyl and carbazolyl), and a silyl group (having preferably 3 to 40 carbon atoms, more preferably 3 to 30 carbon atoms and particularly preferably 3 to 24 carbon atoms and including, for example, trimethylsilyl and triphenylsilyl).

In Formula (1), $L_1$ and $L_2$ each are independently a linkage group having 6 to 30 nuclear carbon atoms which has one or more benzene ring, and at least one of $L_1$ and $L_2$ is a substituted or unsubstituted terphenylene group.

The examples of the linkage group of $L_1$ and $L_2$ include groups obtained by converting the same examples as in the aryl group represented by $Ar_1$ to $Ar_5$ described above into divalent groups, and they are preferably groups represented by the following Formula (2):

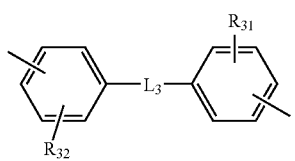

(2)

In Formula (2), $L_3$ is a hetero atom, a substituted or unsubstituted alkylene group having 1 to 6 carbon atoms, a substituted or unsubstituted cycloalkylene group having 3 to 30 carbon atoms, a substituted or unsubstituted arylene group having 6 to 30 nuclear carbon atoms or a substituted or unsubstituted heteroarylene group having 5 to 30 nuclear carbon atoms.

The hetero atom of $L_3$ described above includes, for example, an oxygen atom, a sulfur atom, a nitrogen atom and a silicon atom, and an oxygen atom and a sulfur atom are preferred.

The alkylene group of $L_3$ described above includes, for example, methylene, ethylene, propylene, butylene, pentylene, hexylene, heptylene and octylene, and methylene, dimethylmethylene and diphenylmethylene are preferred.

The cycloalkylene group of $L_3$ described above includes, for example, cyclopropylene, cyclobutylene, cyclopentylene and cyclohexylene, and 1,1-cyclohexylene is preferred.

The arylene group of $L_3$ described above includes, for example, phenylene, biphenylene, terphenylene, quaterphenylene, naphthylene, anthracenylene, phenathrylene, chrysenylene, pyrenylene, fluorenylene, 2,6-diphenylnaphthalene-4',4"-ene and 2-phenylnaphthalene-2,4'-ene, and phenylene, biphenylene, terphenylene fluorenylene.

The heteroarylene group of $L_3$ described above includes, for example, divalent residues such as imidazole, benzimidazole, pyrrole, furan, thiophene, benzothiophene, oxadiazoline, indoline, carbazole, pyridine, quinoline, isoquinoline, benzoquinone, pyralodine, imidazolidine and piperidine, and pyridilene is preferred.

In Formula (2), $R_{31}$ and $R_{32}$ each are independently a hydrogen atom, a substituted or unsubstituted alkyl group having 1 to 6 carbon atoms, a substituted or unsubstituted cycloalkyl group having 3 to 30 carbon atoms or a substituted or unsubstituted aryl group having 6 to 30 nuclear carbon atoms.

The alkyl group of $R_{31}$ and $R_{32}$ described above includes, for example, methyl, ethyl, propyl, isopropyl, n-butyl, s-butyl, isobutyl, t-butyl, n-pentyl, n-hexyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl.

The cycloalkyl group of $R_{31}$ and $R_{32}$ described above includes, for example, cyclopropylene, cyclobutylene, cyclopentylene and cyclohexylene.

The aryl group of $R_{31}$ and $R_{32}$ described above includes, for example, the same examples as those of $Ar_1$ to $Ar_5$ of the aryl group in Formula (1) described above.

$R_{31}$ and $R_{32}$ described above each may be plural, and in such case, plural $R_{31}$ themselves and $R_{32}$ themselves may be combined with each other to form a saturated or unsaturated ring.

The examples of the above ring include cycloalkane having 4 to 12 carbon atoms such as cyclobutane, cyclopentane, cyclohexane, adamantane and norbornane, cycloalkene having 4 to 12 carbon atoms such as cyclobutene, cyclopentene, cyclohexene, cycloheptene and cyclooctene, cycloalkadiene having 6 to 12 carbon atoms such as cyclohexadiene, cycloheptadiene and cyclooctadiene, an aromatic ring having 6 to 50 carbon atoms such as benzene, naphthalene, phenanthrene, anthracene, pyrene, chrysene and acenaphthylene and a heterocyclic ring having 5 to 50 carbon atoms such as imidazole, pyrrole, furan, thiophene and pyridine.

The substituents of the respective groups represented by $L_3$, $R_{31}$ and $R_{32}$ described above include the same examples as the substituents of $Ar_1$ to $Ar_5$ of the aryl group in Formula (1) described above.

Further, the linkage group of $L_1$ and/or $L_2$ is preferably a terphenylene group represented by any of the following formulas:

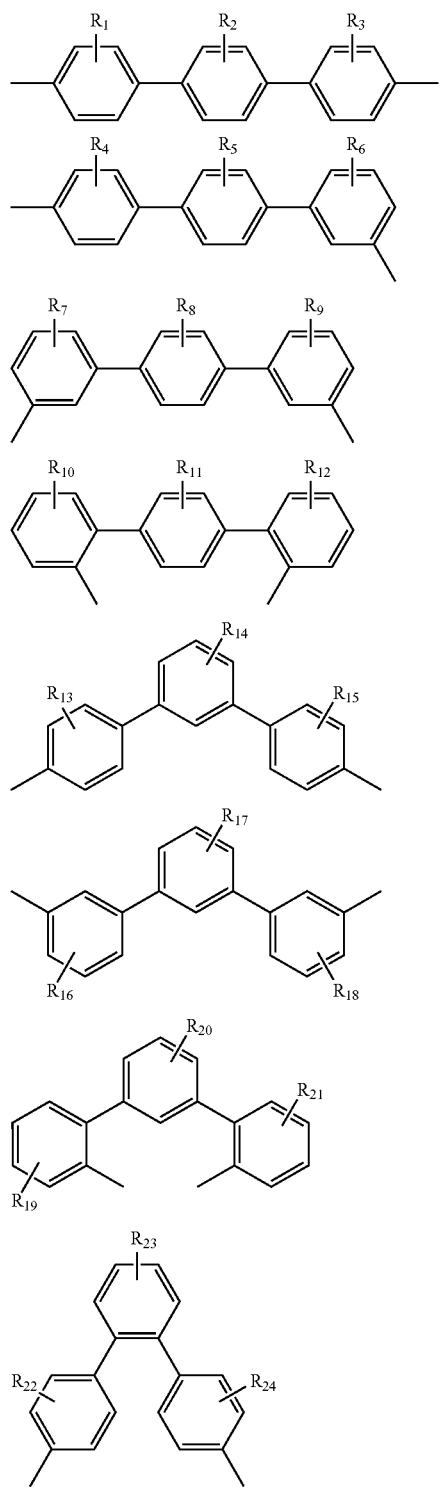

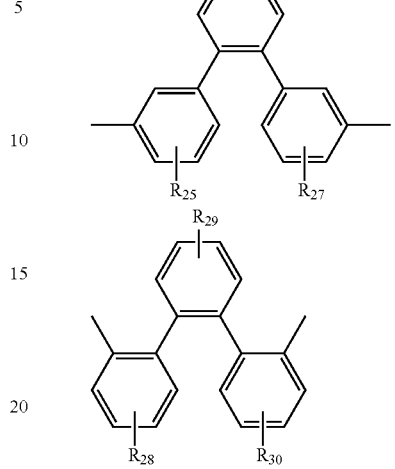

wherein $R_1$ to $R_{30}$ each are independently a hydrogen atom, a substituted or unsubstituted alkyl group having 1 to 6 carbon atoms, a substituted or unsubstituted cycloalkyl group having 3 to 30 carbon atoms or a substituted or unsubstituted aryl group having 6 to 30 nuclear carbon atoms; $R_1$ to $R_{30}$ each may be plural; in such case, adjacent plural $R_{31}$ to $R_{32}$ themselves may be combined with each other to form a saturated or unsaturated ring, and the adjacent groups out of $R_1$ to $R_{30}$ may be combined with each other to form a saturated or unsaturated ring.

The specific examples of the alkyl group, the cycloalkyl group and the aryl group of $R_1$ to $R_{30}$ described above include the same examples as given in $R_{31}$ and $R_{32}$ described above in Formula (2) described above, and the substituents thereof include the same examples as given in $R_{31}$ and $R_{32}$. Further, the examples of the ring which may be formed by $R_1$ to $R_{30}$ include the same examples as given in $R_{31}$ and $R_{32}$.

Among the terphenylene groups described above, the terphenylene group represented by the following Formula (3) is preferred. $R_1$ to $R_3$ are the same as those described above.

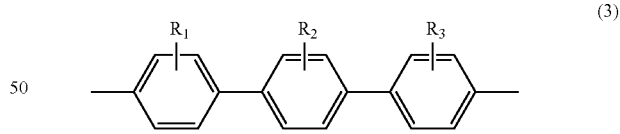

(3)

Figure 2:
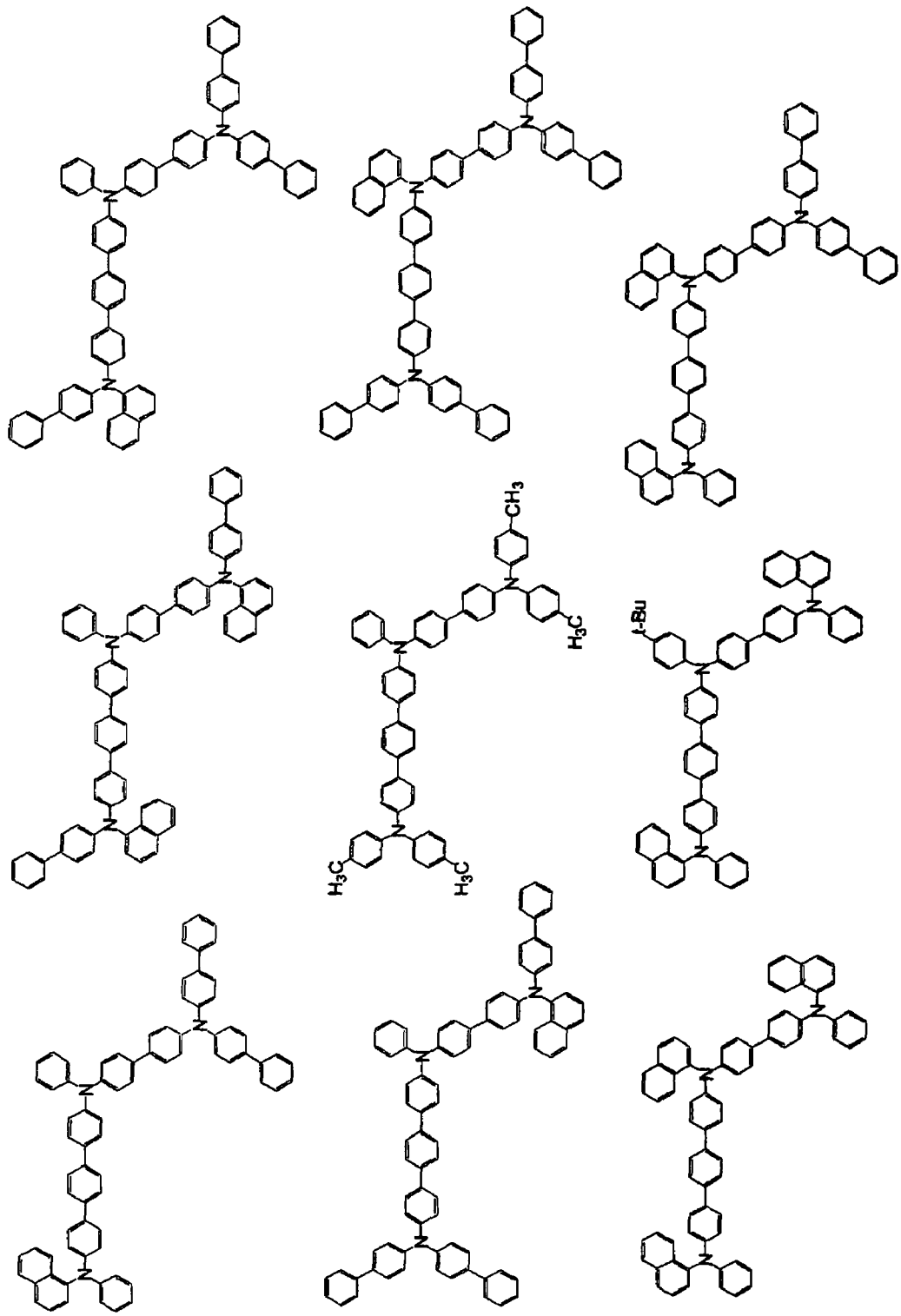
Figure 3:
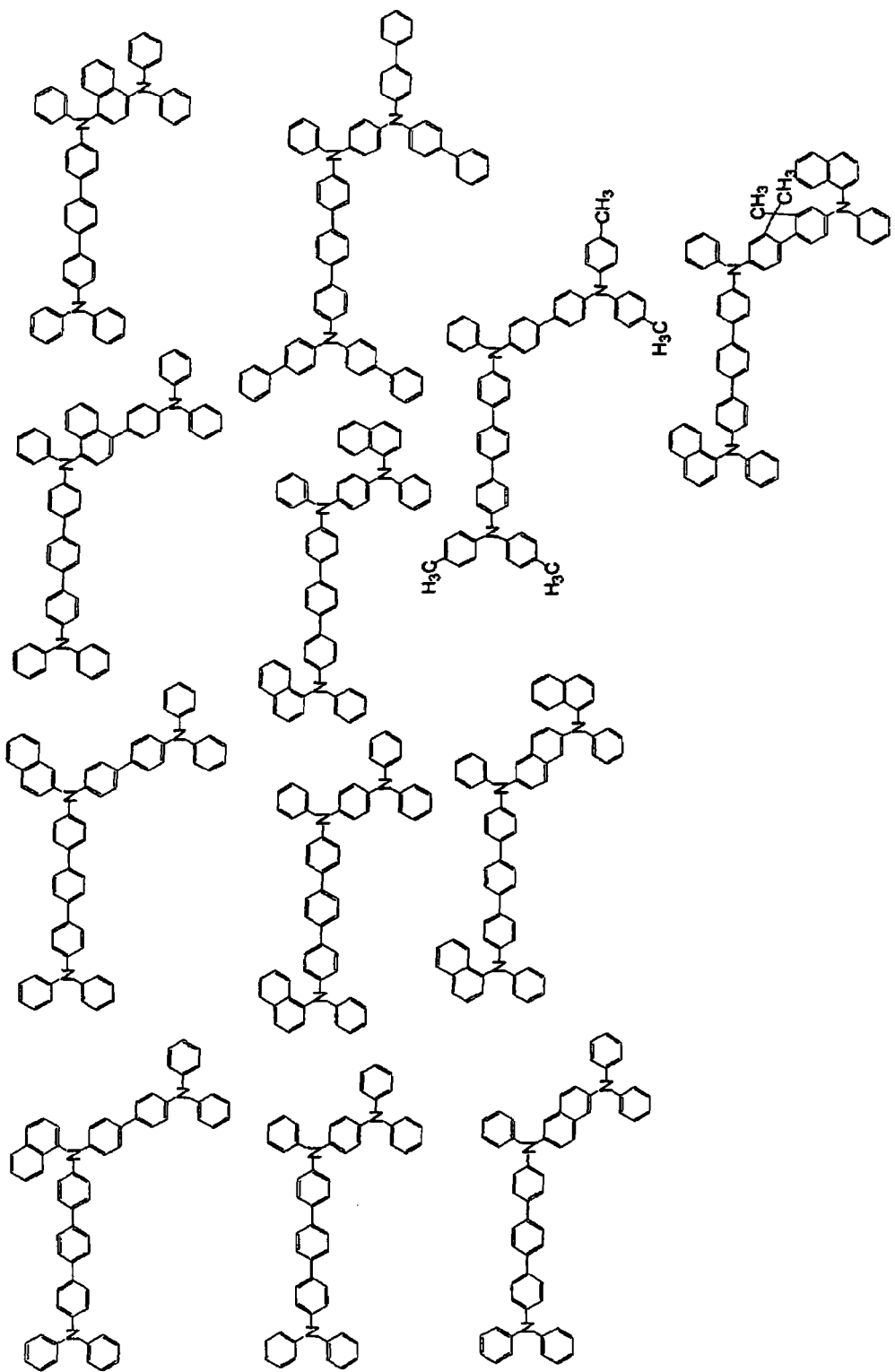
Figure 4:
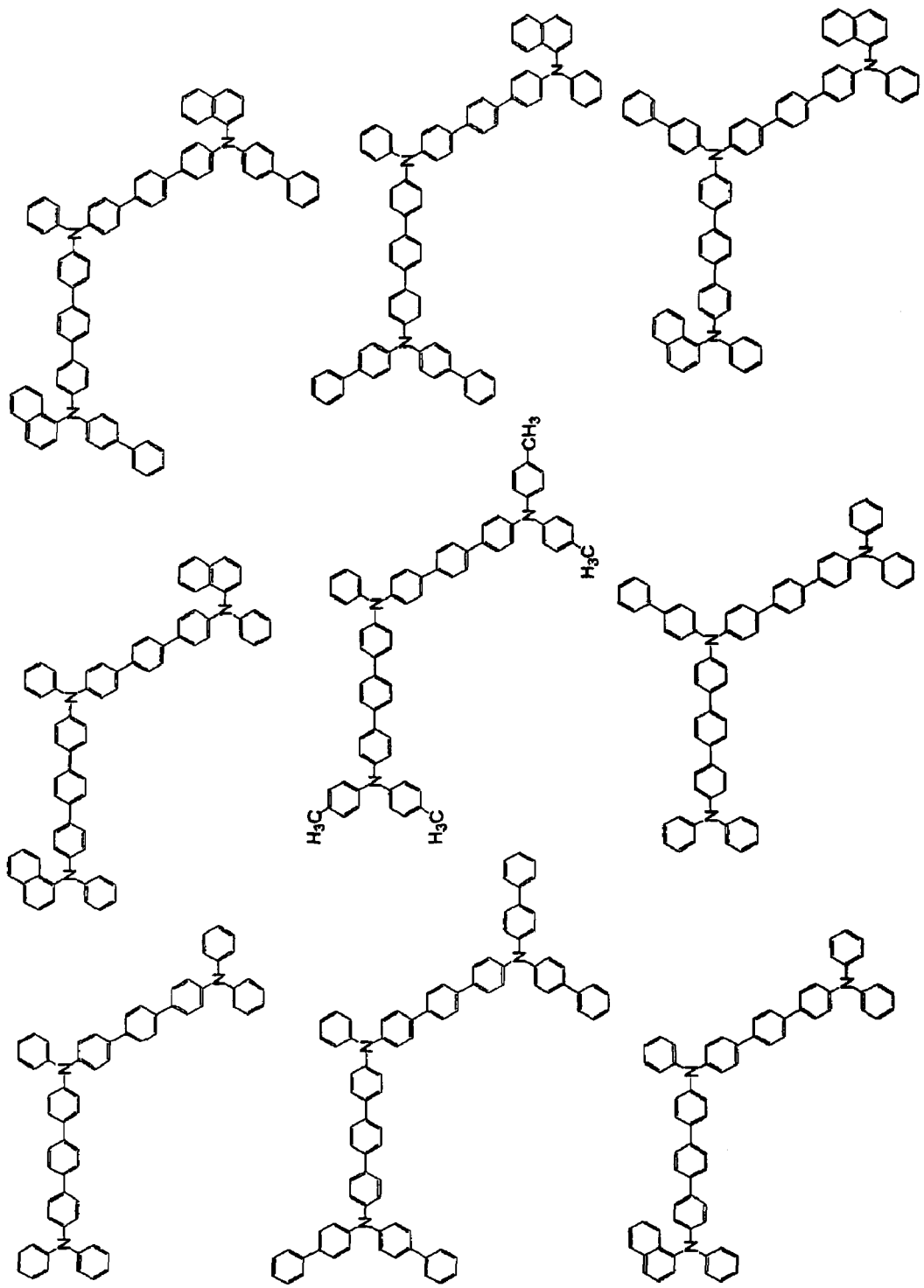
Figure 5:
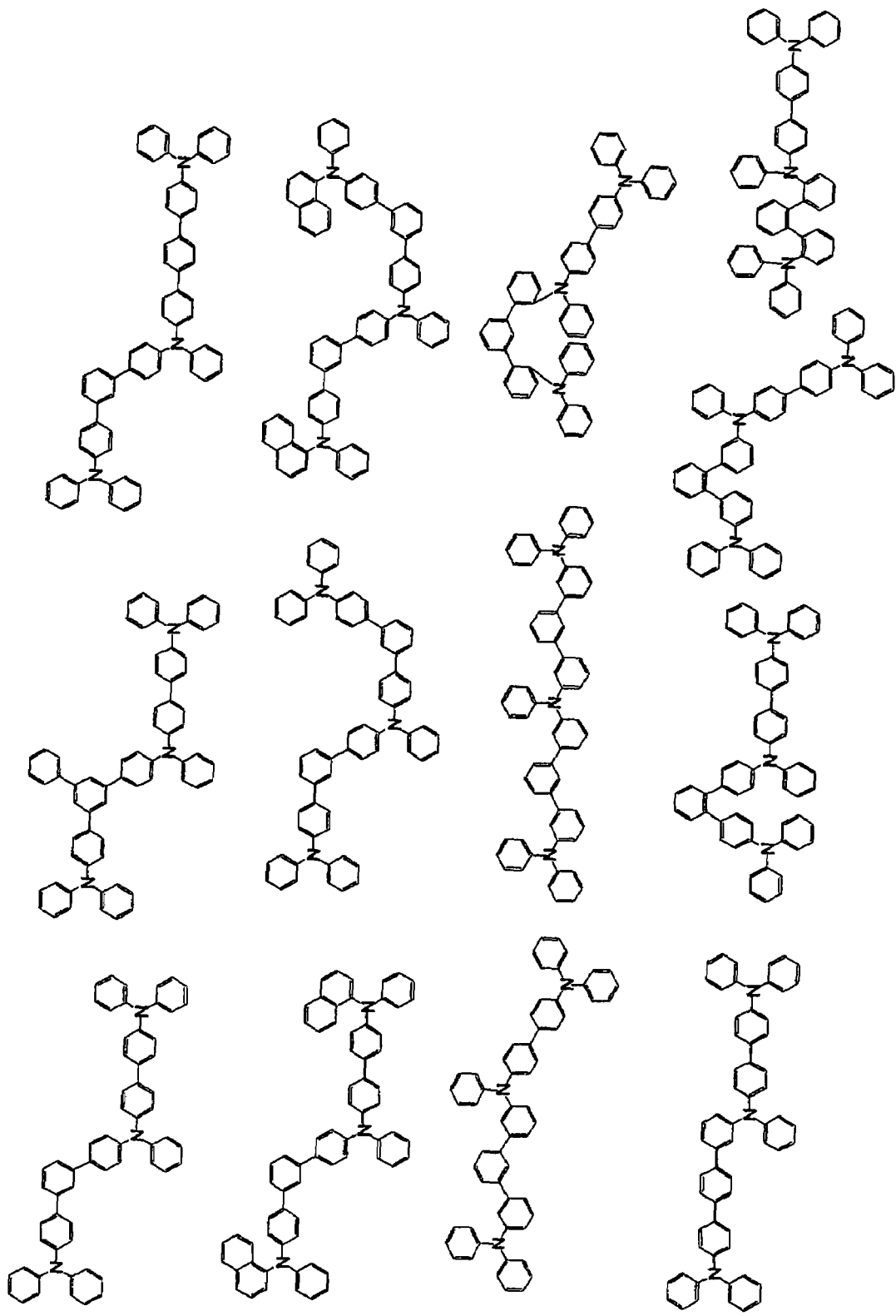
Figure 6:
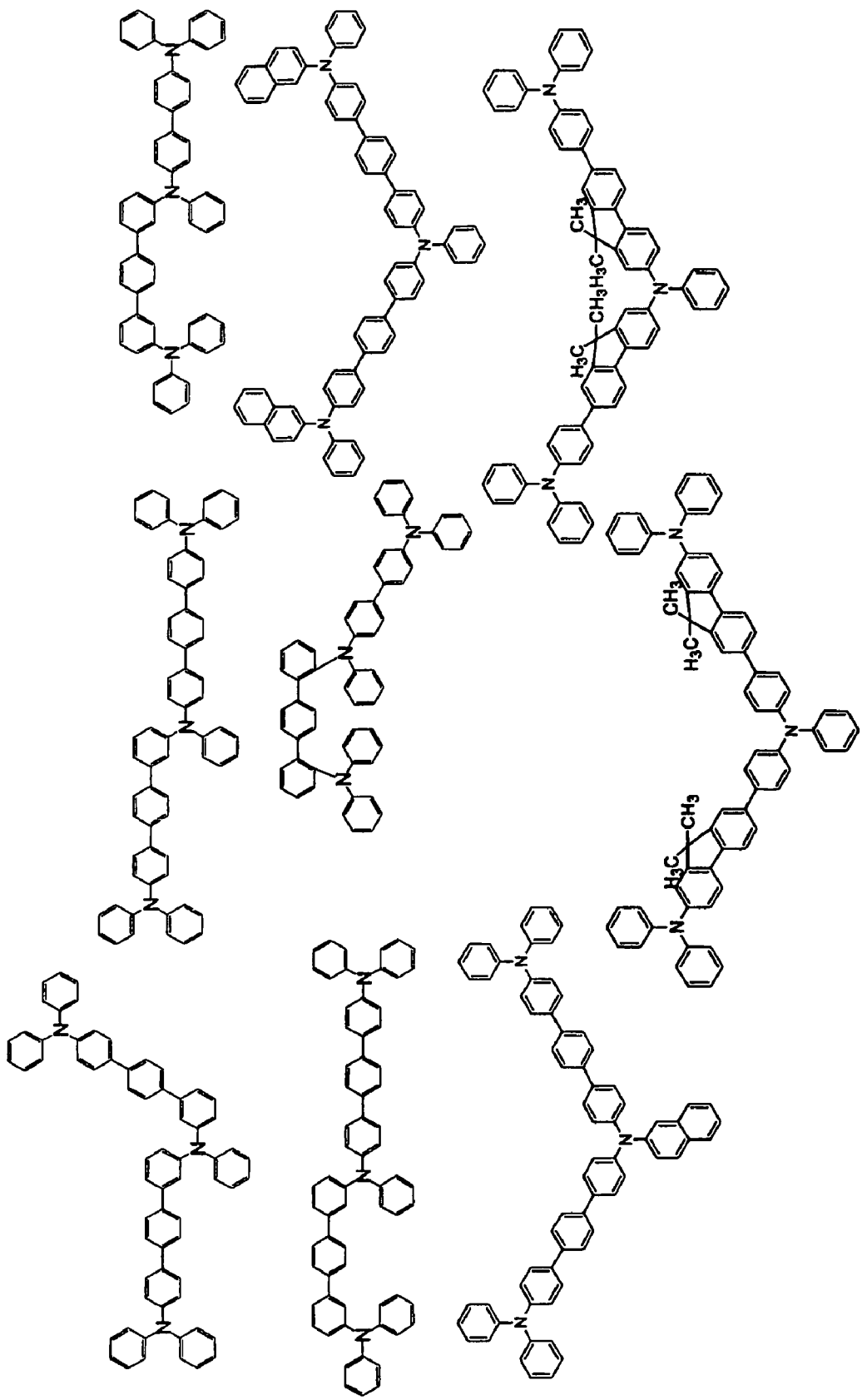
Figure 7:
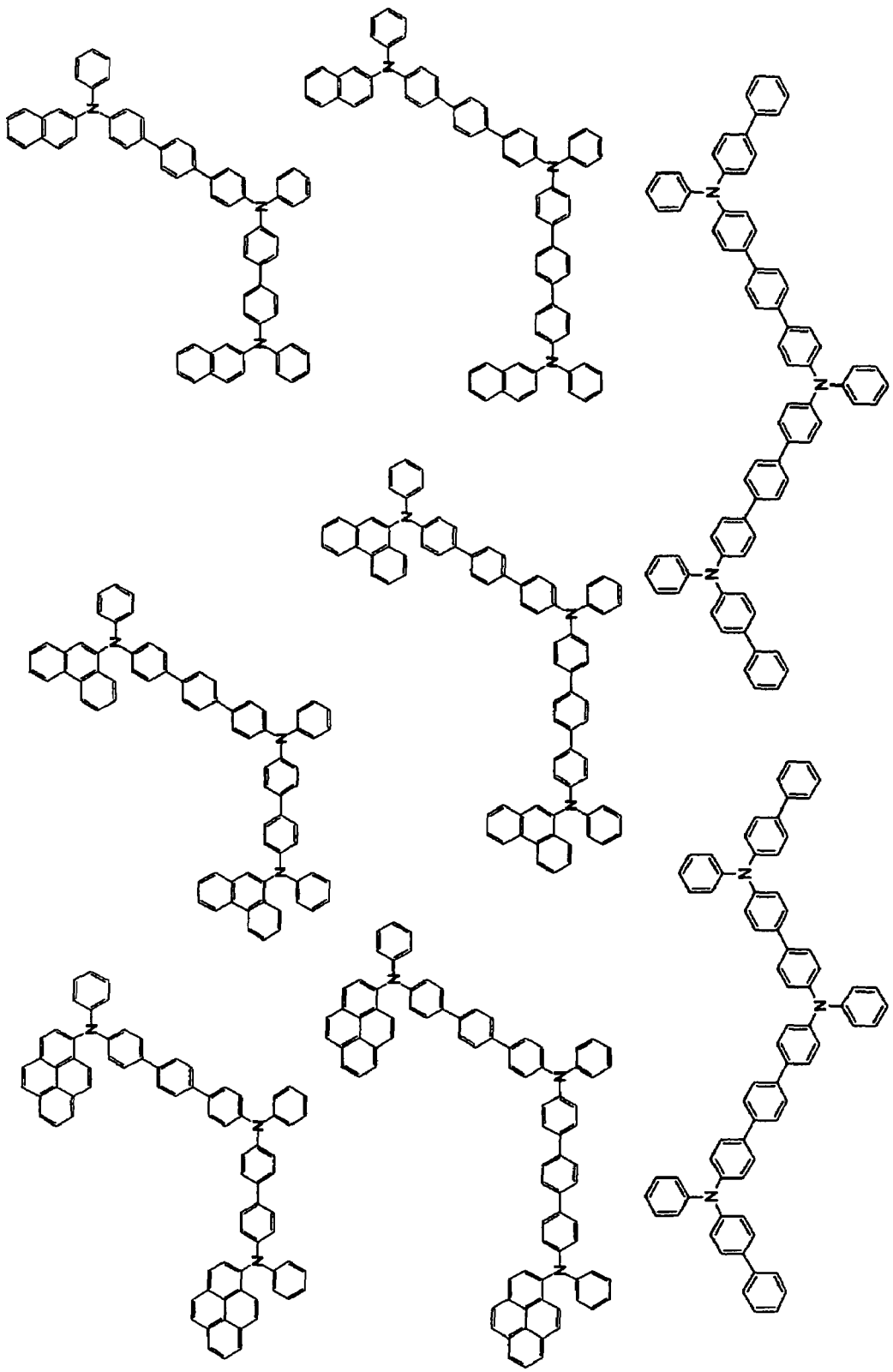
Figure 8:
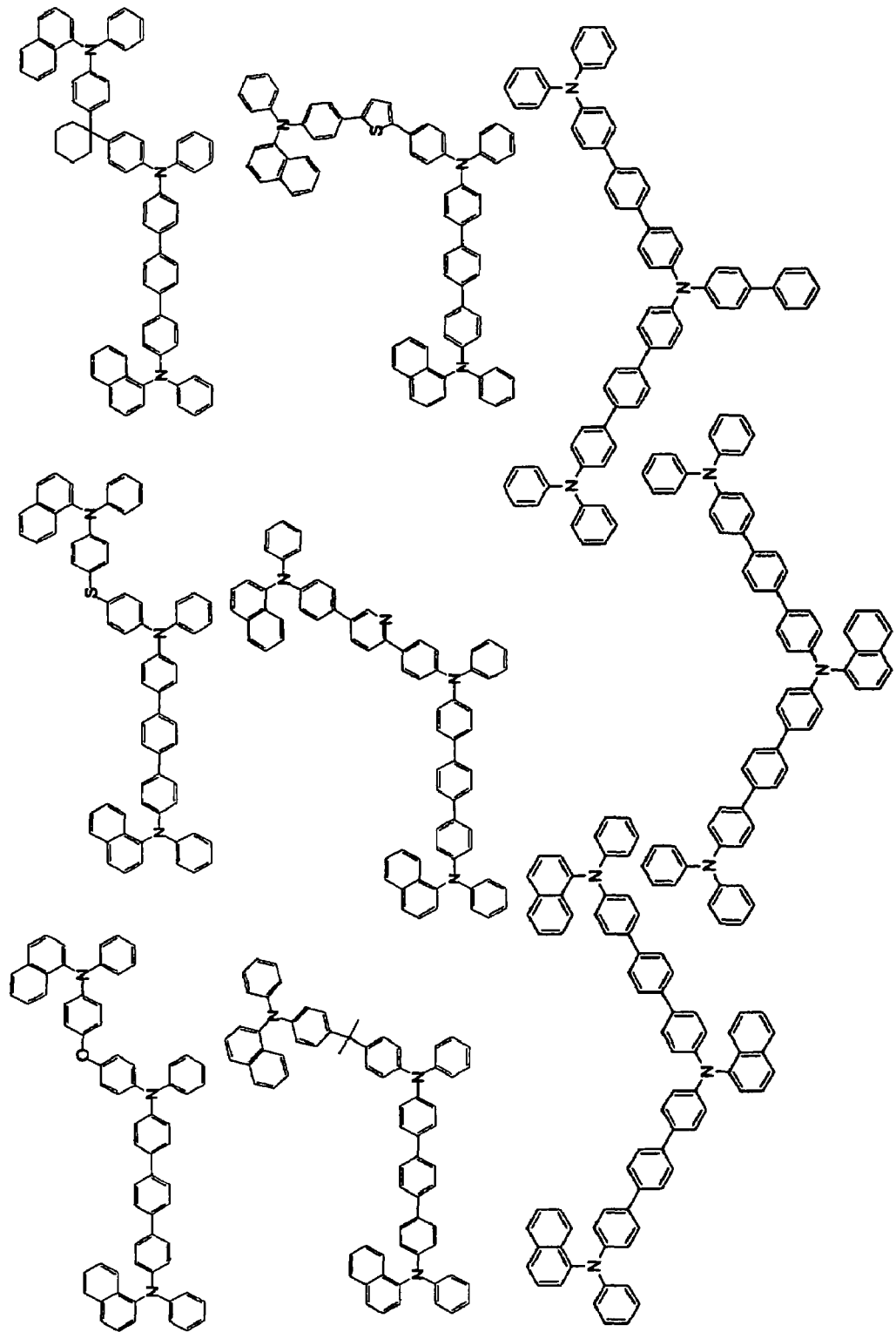

The specific examples of the aromatic triamine compound represented by Formula (1) in the present invention are shown in FIGS. 1-8, but they shall not be restricted to these compounds shown as the examples.

BRIEF DISCRIPTION OF THE DRAWINGS

FIGS. 1-8 show specific examples of the aromatic triamine compound represented by Formula (1)

The aromatic triamine compound of the present invention is preferably a material for an organic EL device, and it is suited particularly to a hole transporting material for an organic EL device and a hole injecting material for an organic EL device. Further, it can also be used as an electron transporting material for an electrophotographic photoreceptor and an organic semiconductor.

Next, the organic EL device of the present invention shall be explained.

In the organic EL device of the present invention in which an organic thin film layer comprising a single layer or plural layers having at least a luminescent layer is interposed between a cathode and an anode, at least one layer of the above organic thin film layers contains the aromatic triamine compound of the present invention in the form of a single component or a mixed component.

Further, the aromatic triamine compound of the present invention is preferably used particularly for an organic EL device which emits blue color.

The device structure of the organic EL device of the present invention shall be explained below.

(1) Structure of the Organic EL Device

The representative device structure of the organic EL device of the present invention include:
(1) anode/luminescent layer/cathode
(2) anode/hole injecting layer/luminescent layer/cathode
(3) anode/luminescent layer/electron injecting layer/cathode
(4) anode/hole injecting layer/luminescent layer/electron injecting layer/cathode
(5) anode/organic semiconductor layer/luminescent layer/cathode
(6) anode/organic semiconductor layer/electron barrier layer/luminescent layer/cathode
(7) anode/organic semiconductor layer/luminescent layer/adhesion improving layer/cathode
(8) anode/hole injecting layer/hole transporting layer/luminescent layer/electron injecting layer/cathode
(9) anode/insulating layer/luminescent layer/insulating layer/cathode
(10) anode/inorganic semiconductor layer/insulating layer/luminescent layer/insulating layer/cathode
(11) anode/organic semiconductor layer/insulating layer/luminescent layer/insulating layer/cathode
(12) anode/insulating layer/hole injecting layer/hole transporting layer/luminescent layer/insulating layer/cathode
(13) anode/insulating layer/hole injecting layer/hole transporting layer/luminescent layer/electron injecting layer/cathode Among them, usually the structures of (4) and (8) are preferably used, but it shall not be restricted to them.

The aromatic triamine compound of the present invention may be used for any organic thin film layer in the organic EL device. It is contained preferably in the hole transporting zone and/or the hole injecting zone, and it is contained more preferably in the hole transporting layer and/or the hole injecting layer. Usually, an amount thereof is selected particularly preferably from 30 to 100 mole %.

(2) Light Transmitting Substrate

The organic EL device of the present invention is prepared on a light transmitting substrate. The light transmitting substrate referred to herein is a substrate supporting the organic EL device, and it is preferably a flat substrate in which a transmission factor of light in a visible region of 400 to 700 nm is 50% or more.

To be specific, it includes a glass plate, a polymer plate and the like. In particular, the glass plate includes soda lime glass, barium.strontium-containing glass, lead glass, aluminosilicate glass, borosilicate glass, barium borosilicate glass and quartz. The polymer plate includes polycarbonate, acryl, polyethylene terephthalate, polyether sulfide and polysulfone.

(3) Anode

An anode in the organic EL device of the present invention has a function to inject a hole into the hole transporting layer or the luminescent layer, and it is effective that the anode has a work function of 4.5 eV or more. Indium tin oxide alloy (ITO), indium zinc oxide alloy (IZO), zinc oxide (NESA), gold, silver, platinum, copper and lanthanoid can be applied as the specific examples of a material for the anode used in the present invention. Further, alloys and laminates thereof may be used.

The anode can be prepared by forming a thin film of the above electrode substances by a method such as a deposition method or a sputtering method.

When light emitted from the luminescent layer is taken out from the anode, a transmission factor of the anode based on light emitted is preferably larger than 10%. A sheet resistance of the anode is preferably several hundred $\Omega/\square$ or less. A film thickness of the anode is selected, though depending on the material, in a range of usually 10 nm to 1 μm, preferably 10 to 200 nm.

(4) Luminescent Layer

The luminescent layer in the organic EL device has the following functions of (1) to (3) in combination.

(1) Injecting function: a function in which a hole can be injected from an anode or a hole injecting layer in applying an electric field and in which an electron can be injected from a cathode or an electron injecting layer.
(2) Transporting function: a function in which a charge (electron and hole) injected is migrated by virtue of a force of an electric field.
(3) Luminescent function: a function in which a field for recombination of an electron and a hole is provided and in which this is connected to luminescence.

Provided that a difference may be present between an easiness in injection of a hole and an easiness in injection of an electron and that a difference may be present in a transporting ability shown by the mobilities of a hole and an electron, but any one of the charges is preferably migrated.

A publicly known method such as, for example, a deposition method, a spin coating method and an LB method can be applied as a method for forming the above luminescent layer. In particular, the luminescent layer is preferably a molecular deposition film. In this case, the molecular deposition film means a thin film formed by depositing a material compound staying in a gas phase state and a film formed by solidifying a material compound staying in a solution state or a liquid phase state, and the above molecular deposition film can usually be distinguished from a thin film (molecular cumulative film) formed by the LB method by a difference in an aggregation structure and a higher order structure and a functional difference originating in it.

Further, as disclosed in Japanese Patent Application Laid-Open No. 51781/1982, the luminescent layer can be formed as well by dissolving a binding agent such as a resin and a material compound in a solvent to prepare a solution and then forming a thin film from it by a spin coating method.

When the aromatic triamine compound of the present invention is used as the luminescent material, other publicly known luminescent materials may be added, and a luminescent layer containing a different publicly known luminescent material may be laminated on the luminescent layer containing the luminescent material comprising the aromatic triamine compound of the present invention.

A host material or a doping material which can be used for the luminescent layer together with the aromatic triamine compound of the present invention includes, for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene and fluorescent coloring matters. However, it shall not be restricted to them.

The host material which can be used for the luminescent layer together with the aromatic triamine compound of the present invention is preferably compounds represented by the following Formulas (i) to (ix).

Asymmetric Anthracene Compound Represented by the Following Formula (i):

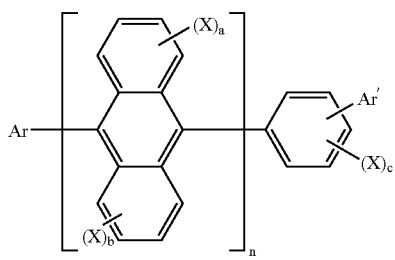

wherein Ar is a substituted or unsubstituted concentrated aromatic group having 10 to 50 nuclear carbon atoms; Ar' is a substituted or unsubstituted aromatic group having 6 to 50 nuclear carbon atoms; X is a substituted or unsubstituted aromatic group having 6 to 50 nuclear carbon atoms, a substituted or unsubstituted aromatic heterocyclic group having 5 to 50 nuclear carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 nuclear carbon atoms, a carboxyl group, a halogen atom, a cyano group, a nitro group or a hydroxyl group; a, b and c each are an integer of 0 to 4; n is an integer of 1 to 3; and when n is 2 or more, an inside of a parenthesis may be the same or different.

Asymmetric Monoanthracene Derivative Represented by the Following Formula (ii):

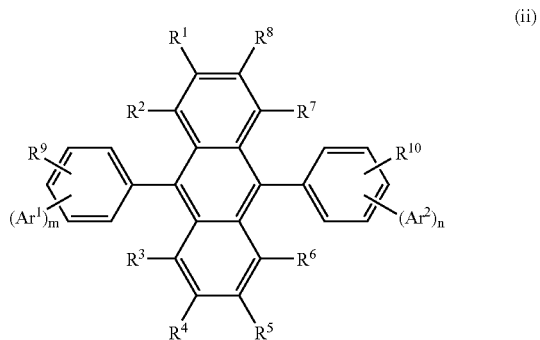

wherein $Ar^1$ and $Ar^2$ each are independently a substituted or unsubstituted aromatic ring group having 6 to 50 nuclear carbon atoms; m and n each are an integer of 1 to 4; provided that when m and n are 1 and the positions of $Ar^1$ and $Ar^2$ bonded to a benzene ring are bilaterally symmetric, $Ar^1$ and $Ar^2$ are not the same, and when m and n are an integer of 2 to 4, m and n are different integers; and $R^1$ to $R^{10}$ each are independently a hydrogen atom, a substituted or unsubstituted aromatic ring group having 6 to 50 nuclear carbon atoms, a substituted or unsubstituted aromatic heterocyclic group having 5 to 50 nuclear carbon atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 nuclear carbon atoms, a substituted or unsubstituted silyl group, a carboxyl group, a halogen atom, a cyano group, a nitro group or a hydroxyl group.

Asymmetric Pyrene Derivative Represented by the Following Formula (iii):

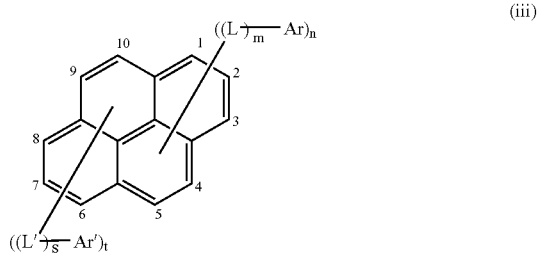

wherein Ar and Ar' each are a substituted or unsubstituted aromatic group having 6 to 50 nuclear carbon atoms;

L and L' each are a substituted or unsubstituted phenylene group, a substituted or unsubstituted naphthalene group, a substituted or unsubstituted fluorenylene group or a substituted or unsubstituted dibenzosilylene group;

m is an integer of 0 to 2; n is an integer of 1 to 4;

s is an integer of 0 to 2; t is an integer of 0 to 4;

L or Ar is bonded to any of 1- to 5-positions of pyrene, and L' or Ar' is bonded to any of 6- to 10-positions of pyrene; provided that n+t is an even number, Ar, Ar', L and L' satisfy (1) or (2) described below:

(1) Ar≠Ar' and/or L≠L' (in this case, ≠ shows that both are groups having different structures) and (2) when Ar=Ar' and L=L',
 (2-1) m≠s and/or n≠t or
 (2-2) when m=s and/or n=t,
 there are not a case in which (2-2-1) L and L' or pyrene each are bonded to different bonding positions on Ar and Ar' or (2-2-2) L and L' or pyrene each are bonded to the same bonding position on Ar and Ar' and a case in which the substitution positions of L and L' or Ar and Ar' in pyrene are a 1-position and a 6-position or a 2-position and a 7-position.

Asymmetric Anthracene Derivative Represented by the Following Formula (Iv):

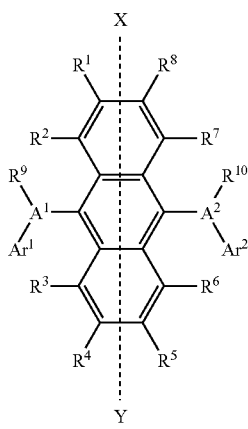

(iv)

wherein $A^1$ and $A^2$ each are independently a substituted or unsubstituted condensed aromatic group having 10 to 20 nuclear carbon atoms;

$Ar^1$ and $Ar^2$ each are independently a hydrogen atom or a substituted or unsubstituted aromatic ring group having 6 to 50 nuclear carbon atoms;

$R^1$ to $R^{10}$ each are independently a hydrogen atom, a substituted or unsubstituted aromatic ring group having 6 to 50 nuclear carbon ring atoms, a substituted or unsubstituted aromatic heterocyclic group having 5 to 50 nuclear carbon atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 nuclear carbon atoms, a substituted or unsubstituted silyl group, a carboxyl group, a halogen atom, a cyano group, a nitro group or a hydroxyl group;

$Ar^1$, $Ar^2$, $R^9$ and $R^{10}$ each may be plural, and adjacent ones may form a saturated or unsaturated cyclic structure; provided that there is no case in which in Formula (1), groups symmetric to an X-Y axis shown on the above anthracene are bonded to a 9-position and a 10-position of central anthracene.

Anthracene Derivative Represented by the Following Formula (v):

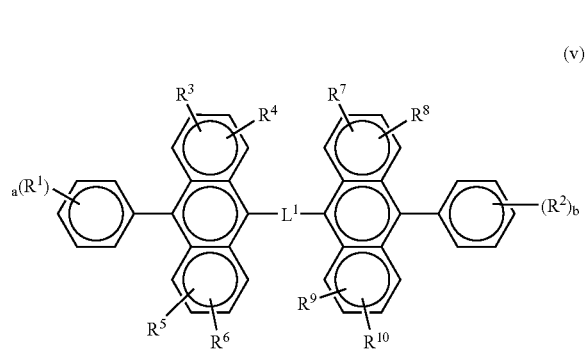

(v)

wherein $R^1$ to $R^{10}$ each represent independently a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; a and b each represent an integer of 1 to 5; when they are 2 or more, $R^1$'s themselves or $R^2$'s themselves each may be the same as or different from each other, and $R^1$'s themselves or $R^2$'s themselves may be combined with each other to form a ring; $R^3$ and $R^4$, $R^5$ and $R^6$, $R^7$ and $R^8$, and $R^9$ and $R^{10}$ may be combined with each other to form rings; and $L^1$ represents a single bond, —O—, —S—, —N(R)— (R is an alkyl group or an aryl group which may be substituted), an alkylene group or an arylene group.

Anthracene Derivative Represented by the Following Formula (vi):

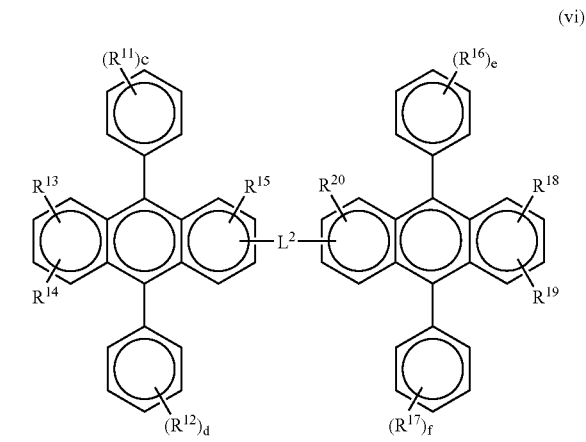

(vi)

wherein $R^{11}$ to $R^{20}$ each represent independently a hydrogen atom, an alkyl group, a cycloalkyl group, an aryl group, an alkoxyl group, an aryloxy group, an alkylamino group, an arylamino group or a heterocyclic group which may be substituted; c, d and e and f each represent an integer of 1 to 5; when they are 2 or more, $R^{11}$'s themselves, $R^{12}$'s themselves, $R^{16}$'s themselves or $R^{17}$'s themselves may be the same as or different from each other, and $R^{11}$'s themselves, $R^{12}$'s themselves, $R^{16}$'s themselves or $R^{17}$'s themselves may be combined with each other to form rings; $R^{13}$ and $R^{14}$ and $R^{18}$ and $R^{19}$ may be combined with each other to form rings; and $L^2$ represents a single bond, —O—, —S—, —N(R)— (R is an alkyl group or an aryl group which may be substituted), an alkylene group or an arylene group.

Spirofluorene Derivative Represented by the Following Formula (vii):

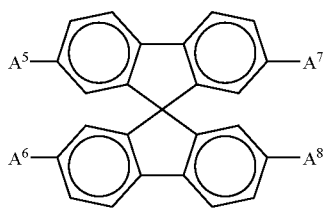

(vii)

wherein $A^5$ to $A^8$ each are independently a substituted or unsubstituted biphenyl group or a substituted or unsubstituted naphthyl group.

Condensed Ring-containing Compound Represented by the Following Formula (viii):

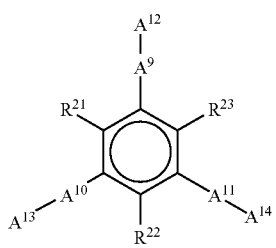

(viii)

wherein $A^9$ to $A^{14}$ are the same as those described above; $R^{21}$ to $R^{23}$ each represent independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of $A^9$ to $A^{14}$ is a group having 3 or more condensed aromatic rings.

Fluorene Compound Represented by the Following Formula (ix):

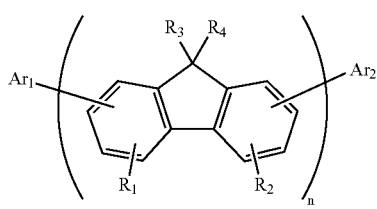

(ix)

wherein $R_1$ and $R_2$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group or a halogen atom; $R_1$'s themselves and $R_2$'s themselves which are bonded to the different fluorene groups may be the same as or different from each other, and $R_1$ and $R_2$ which are bonded to the same fluorene group may be the same or different; $R_3$ and $R_4$ represent a hydrogen atom, a substituted or unsubstituted alkyl group, a substituted or unsubstituted aralkyl group, a substituted or unsubstituted aryl group or a substituted or unsubstituted heterocyclic group; $R_3$'s themselves and $R_4$'s themselves which are bonded to the different fluorene groups may be the same as or different from each other, and $R_3$ and $R_4$ which are bonded to the same fluorene group may be the same or different; $Ar_1$ and $Ar_2$ represent a substituted or unsubstituted condensed polycyclic aromatic group in which the total of benzene rings is 3 or more or a condensed polycyclic heterocyclic group in which the total of benzene rings and heterocycles is 3 or more or and which is bonded to the fluorene group via substituted or unsubstituted carbon; $Ar_1$ and $Ar_2$ may be the same or different and n represents an integer of 1 to 10.

Among the host materials described above, the anthracene derivatives are preferred, and the monoanthracene derivatives are more preferred. The asymmetric anthracene derivatives are particularly preferred.

Phosphorescent compounds can also be used as the luminescent material of a dopant. Compounds containing a carbazole ring for a host material are preferred as the phosphorescent compound. The dopant is a compound which can emit light from a triplet exciton, and it shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred.

The host suited to phosphorescence comprising the compound containing a carbazole ring is a compound having a function in which transfer of energy from an excited state thereof to a phosphorescent compound takes place and in which as a result thereof, the phosphorescent compound emits light. The host compound shall not specifically be restricted as long as it is a compound which can transfer exciton energy to the phosphorescent compound, and it can suitably be selected according to the purposes. It may have an optional heterocycle in addition to a carbazole ring.

The specific examples of the above host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorene derivatives, hydrazone derivatives, stilbene derivatives, silazane derivatives, aromatic tertiary amine derivatives, styrylamine derivatives, aromatic dimethylidene base compounds, porphyrin base compounds, anthraquinonedimethane derivatives, anthrone derivatives, diphenylquinone derivatives, thiopyran dioxide derivatives, carbodiimide derivatives, fluorenilidenemethane derivatives, distyrylpyrazine derivatives, heterocyclic tetracarboxylic anhydride such as naphthaleneperylene, metal complexes of phthalocyanine derivatives and 8-quinolinol derivatives, various metal complex polysilane base compounds represented by metal complexes comprising metal phthalocyanine, benzoxazole and benzothiazole as ligands and high molecular compounds including poly(N-vinylcarbazole) derivatives, aniline base copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination two or more kinds thereof.

The specific examples thereof include the following compounds:

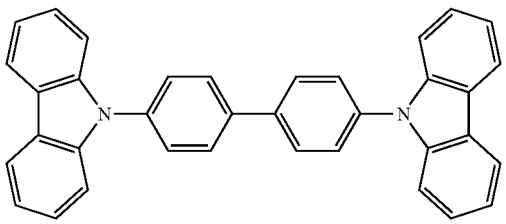

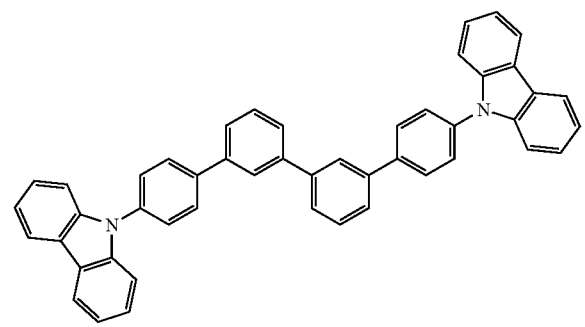

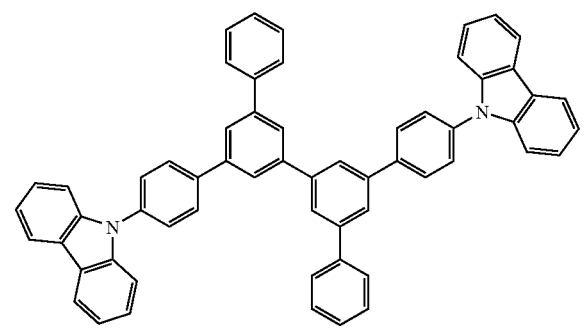

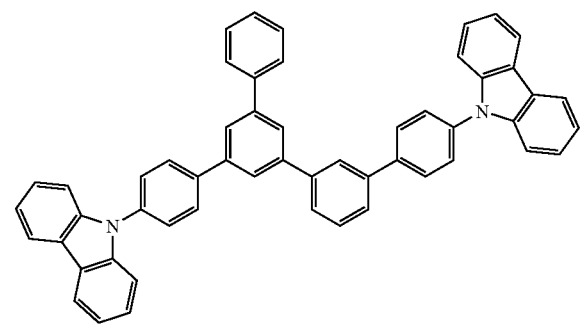

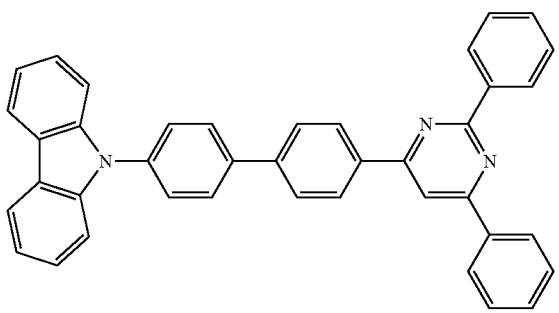

-continued

The phosphorescent dopant is a compound which can emit light from a triplet exciton. It shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred. The porphyrin metal complex is preferably a porphyrin platinum complex. The phosphorescent compounds may be used alone or in combination of two or more kinds thereof.

A ligand forming the ortho-metallated metal complex includes various ones, and the preferred ligand includes 2-phenylpyridine derivatives, 7,8-benzoquinoline derivatives, 2-(2-thienyl)pyridine derivatives, 2-(1-naphthyl)pyridine derivatives and 2-phenylquinoline derivatives. The above derivatives may have, if necessary, substituents. In particular, the compounds into which fluorides and trifluoromethyl are introduced are preferred as a blue color dopant. Further, it may have, as an auxiliary ligand, ligands other than the ligands described above such as acetylacetonate and picric acid.

A content of the phosphorescent dopant in the luminescent layer shall not specifically be restricted, and it can suitably be selected according to the purposes. It is, for example, 0.1 to 70 mass %, preferably 1 to 30 mass %. If A content of the phosphorescent dopant is less than 0.1 mass %, luminescence is faint, and an addition effect thereof is not sufficiently exhibited. On the other hand, if it exceeds 70 mass %, a phenomenon called concentration quenching becomes marked, and the device performance is reduced.

The luminescent layer may contain, if necessary, a hole transporting material, an electron transporting material and a polymer binder.

A film thickness of the luminescent layer is preferably 5 to 50 nm, more preferably 7 to 50 nm and most preferably 10 to 50 nm. If it is less than 5 nm, it is difficult to form the luminescent layer, and controlling of the chromaticity is likely to become difficult. On the other hand, if it exceeds 50 nm, the driving voltage is likely to go up.

(5) Hole Injecting and Transporting Layer

The hole injecting and transporting layer is a layer for assisting injection of a hole into the luminescent layer to transport it to the luminescent region, and it has a large hole mobility and shows a small ionization energy of usually 5.5 eV or less. A material which transports a hole to the luminescent layer by a lower electric field intensity is preferred as the above hole injecting and transporting layer, and more preferred is a material in which a mobility of a hole is at least $10^{-4}$ $cm^2$/V·second in applying an electric field of, for example, $10^4$ to $10^6$ V/cm.

When the aromatic triamine compound of the resent invention is used in the hole injecting and transporting zone, the hole injecting and transporting layer may be formed from the aromatic triamine compound of the resent invention alone or it may be used in a mixture with other materials.

The material for forming the hole injecting and transporting layer by mixing with the aromatic triamine compound of the present invention shall not specifically be restricted as long as they have the preferred properties described above, and capable of being used are optional materials selected from materials which have so far been conventionally used as charge transporting materials of holes in photoconductive materials and publicly known materials which are used for a hole injecting and transporting layer in an organic EL device.

The specific examples thereof include triazole derivatives (refer to U.S. Pat. No. 3,112,197), oxadiazole derivatives (refer to U.S. Pat. No. 3,189,447), imidazole derivatives (refer to Japanese Patent Publication No. 16096/1962), polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto 10983/1976 and Japanese Patent Application Laid-Open No. 93224/1976, ditto 17105/1980, ditto 4148/1981, ditto 10866/1980, ditto 156953/1980 and ditto 36656/1981), pyrazoline derivatives and pyrazolone derivatives (refer to U.S. Pat. No. 3,180,729 and ditto U.S. Pat. No. 4,278,746 and Japanese Patent Application Laid-Open No. 88064/1980, ditto 88065/1980, ditto 105537/1974, ditto 51086/1980, ditto 80051/1981, ditto 88141/1981, ditto 45545/1982, ditto 112637/1979 and ditto 74546/1980), phenylenediamine derivatives (refer to U.S. Pat. No. 3,615,404, Japanese Patent Publication No. 10105/1976, ditto 3712/1971 and ditto 25336/1972 and Japanese Patent Application Laid-Open No. 53435/1979, ditto 110536/1979 and ditto 119925/1979), arylamine derivatives (refer to U.S. Pat. No. 3,567,450, ditto U.S. Pat. No. 3,180,703, ditto U.S. Pat. No. 3,240,597, ditto U.S. Pat. No. 3,658,520, ditto U.S. Pat. No. 4,232,103, ditto U.S. Pat. No. 4,175,961 and ditto U.S. Pat. No. 4,012,376, Japanese Patent Publication No. 35702/1974 and ditto 27577/1964, Japanese Patent Application Laid-Open No. 144250/1980, ditto 119132/1981 and ditto 22437/1981 and German Patent 1,110,518), amino-substituted chalcone derivatives (refer to U.S. Pat. No. 3,526,501), oxazole derivatives (disclosed in U.S. Pat. No. 3,257,203), styrylanthracene derivatives (refer to Japanese Patent Application Laid-Open No. 46234/1981), fluorenone derivatives (refer to Japanese Patent Application Laid-Open No. 110837/1979), hydrazone derivatives (refer to U.S. Pat. No. 3,717,462, Japanese Patent Application Laid-Open No. 59143/1979, ditto 52063/1980, ditto 52064/1980, ditto 46760/1980, ditto 85495/1980, ditto 11350/1982 and ditto 148749/1982 and Japanese Patent Application Laid-Open No. 311591/1990), stilbene derivatives (Japanese Patent Application Laid-Open No. 210363/1986, ditto 228451/1986, ditto 14642/1986, ditto 72255/1986, ditto 47646/1987, ditto 36674/1987, ditto 10652/1987, ditto 30255/1987, ditto 93455/1985, ditto 94462/1985, ditto 174749/1985 and ditto 175052/1985), silazane derivatives (refer to U.S. Pat. No. 4,950,950), polysilane base (refer to Japanese Patent Application Laid-Open No. 204996/1990), aniline base copolymers (refer to Japanese Patent Application Laid-Open No. 282263/1990) and electroconductive high molecular oligomers (particularly thiophene oligomers) disclosed in Japanese Patent Application Laid-Open No. 211399/1989.

The compounds described above can be used as the material for the hole injecting and transporting layer, and preferably used are porphyrin compounds (disclosed in Japanese Patent Application Laid-Open No. 295695/1988), aromatic tertiary amine compounds and styrylamine compounds (refer to U.S. Pat. No. 4,127,412 and Japanese Patent Application Laid-Open No. 27033/1978, ditto 58445/1979, ditto 149634/1979, ditto 64299/1979, ditto 79450/1980, ditto 144250/1980, ditto 119132/1981, ditto 295558/1986, ditto 98353/1986 and ditto 295695/1988), and the aromatic tertiary amine compounds are particularly preferably used.

Further, capable of being given are compounds having two condensed aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4"-tris(N-(3-methylphenyl)-N-phenylamino)triphenyl (hereinafter abbreviated as MTDATA) in which three triphenylamine units are combined in the form of a star burst type disclosed in Japanese Patent Application Laid-Open No. 308688/1992.

Further, inorganic compounds such as p type Si, p type SiC and the like can also be used as the material for the hole injecting and transporting layer in addition to the compounds described above shown as the materials for the luminescent layer.

The hole injecting and transporting layer can be formed by making a thin film by a publicly known method such as, for example, a vacuum deposition method, a spin coating method, a casting method and an LB method. A film thickness of the hole injecting and transporting layer shall not specifically be restricted, and it is usually 5 nm to 5 μm. When containing the aromatic triamine derivative of the resent invention, the above hole injecting and transporting layer may be constituted from a single layer comprising the aromatic triamine derivative of the present invention and at least one of the materials described above, and it may be formed by laminating a hole injecting and transporting layer comprising compounds which are different from those used in the hole injecting and transporting layer containing the aromatic triamine derivative of the present invention.

Further, an organic semiconductor layer may be provided as a layer for assisting injection of a hole or injection of an electron into the luminescent layer, and the layer having a conductance of $10^{-10}$ S/cm or more is suited. Capable of being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

(6) Electron Injecting and Transporting Layer

Next, the electron injecting layer and transporting layer is a layer for assisting injection of an electron into the luminescent layer to transport it to the luminescent region, and it has a large electron mobility. Also, the adhesion improving layer is a layer comprising particularly a material having a good adhesive property with the cathode in the above electron injecting layer.

It is known that since light emitted from an organic EL device is reflected by an electrode (in this case, a cathode), light emitted directly from an anode is interfered with light emitted via reflection by the electrode. In order to make efficient use of the above interference effect, the electron transporting layer is suitably selected in a film thickness of several nm to several μm, and particularly when the film thickness is large, the electron mobility is preferably at least $10^{-5}$ cm$^2$/Vs or more in applying an electric field of $10^4$ to $10^6$ V in order to avoid a rise in voltage.

The materials used for the electron injecting layer are suitably metal complexes of 8-hyroxyquinoline or derivatives thereof and oxadiazole derivatives. The specific examples of the metal complexes of 8-hyroxyquinoline or the derivatives thereof include metal chelate oxynoid compounds containing chelates of oxine (in general, 8-quinolinol or 8-hyroxyquinolinol), and, for example, tris(8-quinolinol)aluminum can be used as the electron injecting material.

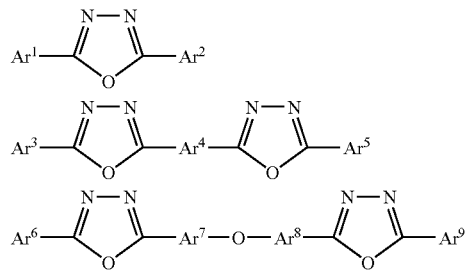

wherein $Ar^1$, $Ar^2$, $Ar^3$, $Ar^5$, $Ar^6$ and $Ar^9$ each represent a substituted or unsubstituted aryl group, and they may be the same as or different from each other; $Ar^4$ $Ar^7$ and $Ar^8$ each represent a substituted or unsubstituted arylene group, and they may be the same as or different from each other.

In this connection, the aryl group includes, for example, phenyl, biphenyl, anthranyl, perylenyl and pyrenyl. Also, the arylene group includes, for example, phenylene, naphthylene, biphenylene, anthranylene, perylenylene and pyrenylene. The substituents therefor include an alkyl group having 1 to 10 carbon atoms, an alkoxy group having 1 to 10 carbon atoms and a cyano group. The above electron transmitting compounds have preferably a thin film-forming property.

The following compounds can be given as the specific examples of the electron transmitting compounds described above:

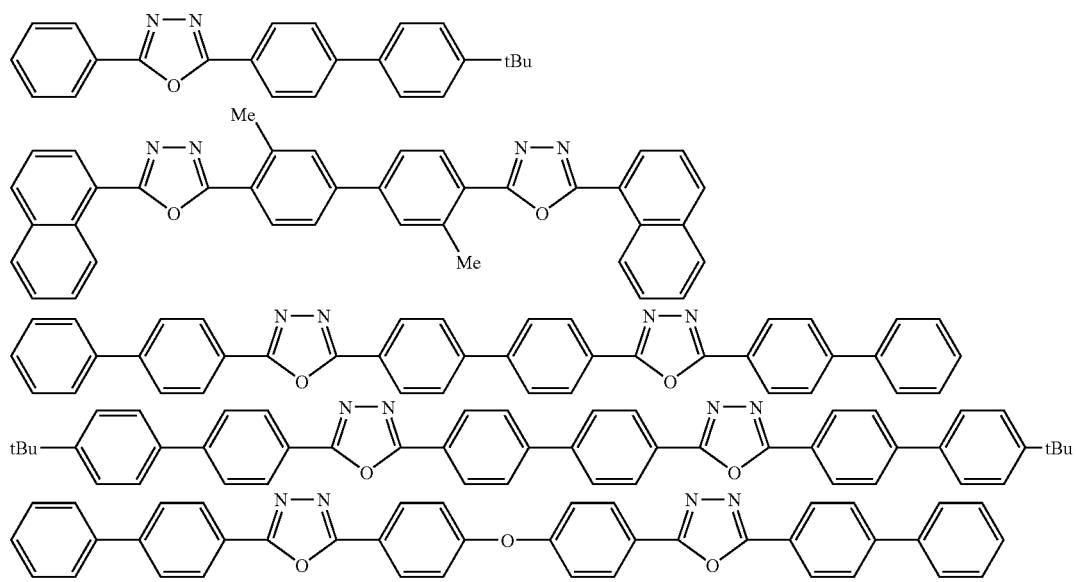

On the other hand, the oxadiazole derivative includes electron transmitting compounds represented by the following formulas:

Further, Compounds represented by the following Formulas (A) to (F) can be used as the materials used for the electron injecting layer and the transporting layer.

Nitrogen-containing Heterocyclic Derivatives Represented by:

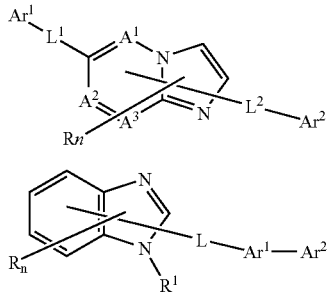

Silacyclopentadiene Derivative Represented by:

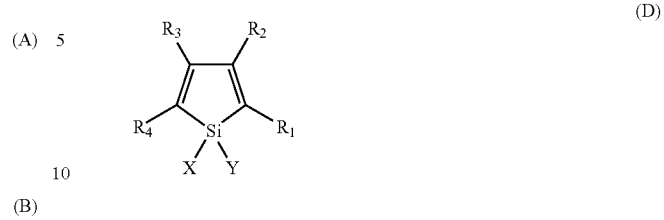

(wherein X and Y each are independently a saturated or unsaturated hydrocarbon group having 1 to 6 carbon atoms, an alkoxy group, an alkenyloxy group, an alkynyloxy group, a hydroxy group, a saturated or unsaturated aryl group, a substituted or unsubstituted heterocycle or a structure in which X is combined with Y to form a saturated or unsaturated ring; $R^1$ to $R^4$ each are independently a hydrogen atom, a halogen atom, a saturated or unsaturated alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, a cyano group or a structure in which substituted or unsubstituted rings are condensed when they are adjacent).

(in Formulas (A) and (B), $A^1$ to $A^3$ each are independently a nitrogen atom or an oxygen atom; $Ar^1$ is a substituted or unsubstituted aryl group having 6 to 60 nuclear carbon atoms or a substituted or unsubstituted heteroaryl group having 3 to 60 nuclear carbon atoms; $Ar^2$ is a hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxy group having 1 to 20 carbon atoms or a divalent group thereof; provided that any one of $Ar^1$ and $Ar^2$ is a substituted or unsubstituted condensed ring group having 10 to 60 nuclear carbon atoms or a substituted or unsubstituted monohetero condensed ring group having 3 to 60 nuclear carbon atoms;

$L_1$, $L_2$ and L each are independently a single bond, a substituted or unsubstituted arylene group having 6 to 60 nuclear carbon atoms, a substituted or unsubstituted heteroarylene group having 3 to 60 nuclear carbon atoms or a substituted or unsubstituted fluorenylene group;

R is a hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxy group having 1 to 20 carbon atoms; n is an integer of 0 to 5; when n is 2 or more, plural R's may be the same or different, and adjacent plural R's may be combined with each other to form a carbocyclic aliphatic ring or a carbocyclic aromatic ring).

Nitrogen-containing Heterocyclic Derivative Represented by:

 (C)

(wherein HAr is a nitrogen-containing heterocycle having 3 to 40 carbon atoms which may have a substituent; L is a single bond, an arylene group having 6 to 60 carbon atoms which may have a substituent, a heteroarylene group having 3 to 60 carbon atoms which may have a substituent or a fluorenylene group which may have a substituent; $Ar^1$ is a divalent hydrocarbon group having 6 to 60 carbon atoms which may have a substituent; and $Ar^2$ is an aryl group having 6 to 60 carbon atoms which may have a substituent or a heteroaryl group having 3 to 60 carbon atoms which may have a substituent).

Borane Derivative Represented by:

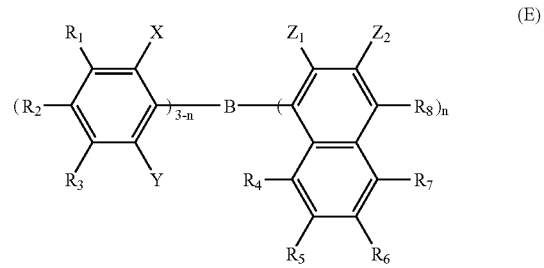

(wherein $R^1$ to $R^8$ each represent independently a hydrogen atom, a saturated or unsaturated hydrocarbon group, an aromatic group, a heterocyclic group, a substituted amino group, a saturated boryl group, an alkoxy group or an aryloxy group; X, Y and $Z_1$ each represent independently a hydrogen atom, a saturated or unsaturated hydrocarbon group, an aromatic group, a heterocyclic group, a substituted amino group, an alkoxy group or an aryloxy group; substituents of $Z_1$ and $Z_2$ may be combined with each other to form a condensed ring; n represents an integer of 1 to 3, and when n is 2 or more, $Z_1$'s may be differnt; provided that a case in which n is 1 and X, Y and $R_2$ are methyl and in which $R_8$ is a hydrogen atom or a saturated boryl group and a case in which n is 3 and $Z_1$ is methyl are not included).

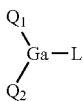

(F)

[wherein $Q^1$ and $Q^2$ each represent independently a ligand represented by the following Formula (G), and L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ ($R^1$ is a hydrogen atom, a substituted or unsubstituted alkyl group, a substituted or unsubstituted cycloalkyl group, a substituted or unsubstituted aryl group or a substituted or unsubstituted heterocyclic group) or —O—Ga-$Q^3(Q^4)$ ($Q^3$ and $Q^4$ are the same as $Q^1$ and $Q^2$)]:

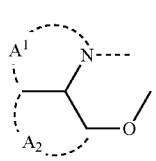

(G)

[wherein rings $A^1$ and $A^2$ are a six-membered aryl ring structure which may have a substituent and in which they are condensed with each other].

This metal complex has a strong property of an n type semiconductor and a large electron injecting ability. Further, since it has low production energy in forming the complex, a bonding property between the metal and the ligand of the metal complex formed becomes firm, and a fluorescence quantum efficiency of the luminescent material becomes large.

The specific examples of substituents of the rings $A^1$ and $A^2$ forming the ligand represented by Formula (G) include a halogen atom such as chlorine, bromine, iodine and fluorine, a substituted or unsubstituted alkyl group such as methyl, ethyl, propyl, butyl, sec-butyl, tert-butyl, pentyl, hexyl, heptyl, octyl, stearyl and trichloromethyl, a substituted or unsubstituted aryl group such as phenyl, naphthyl, 3-methylphenyl, 3-methoxyphenyl, 3-fluorophenyl, 3-trichloromethylphenyl, 3-trifluoromethylphenyl and 3-nitrophenyl, a substituted or unsubstituted alkoxy group such as methoxy, n-butoxy, tert-butoxy, trichloromethoxy, trifluoromethoxy, pentafluoropropoxy, 2,2,3,3-tetrafluoropropoxy, 1,1,3,3,3-hexafluoro-2-propoxy and 6-(perfluoromethyl)hexyloxy, a substituted or unsubstituted aryloxy group such as phenoxy, p-nitrophenoxy, p-tert-butylphenoxy, 3-fluorophenoxy, pentafluorophenoxy and 3-trifluoromethylphenoxy, a substituted or unsubstituted alkylthio group such as methylthio, ethylthio, tert-butylthio, hexylthio, octylthio and trifluoromethylthio, a substituted or unsubstituted arylthio group such as phenylthio, p-nitrophenylthio, tert-butylphenylthio, 3-fluorophenylthio, pentafluorophenylthio and 3-trifluoromethylphenylthio, a cyano group, a nitro group, a mono- or disubstituted amino group such as amino, methylamino, diethylamino, ethylamino, diethylamino, dipropylamino, dibutylamino and diphenylamino, an acylamino group such as bis(acetoxymethyl)amino, bis(acetoxyethyl)amino, bis (acetoxypropyl)amino and bis(acetoxybutyl)amino, a hydroxyl group, a hydroxy group, an acyl group, a carbamoyl group such as methylcarbamoyl, dimethylcarbamoyl, ethylcarbamoyl, diethylcarbamoyl, propylcarbamoyl, butylcarbamoyl and phenylcarbamoyl, a carboxylic acid group, a sulfonic acid group, an imide group, a cycloalkyl group such as cyclopentane and cyclohexyl, an aryl group such as phenyl, naphthyl, biphenyl, anthranyl, phenanthryl, fluorenyl, pyrenyl and a heterocyclic group such as pyridinyl, pyrazinyl, pyrimidinyl, pyridazinyl, triazinyl, indolinyl, quinolinyl, acridinyl, pyrrolidinyl, dioxanyl, piperidinyl, morpholidinyl, piperazinyl, triatinyl, carbazolyl, furanyl, thiophenyl, oxazolyl, oxadiazolyl, benzoxazolyl, thiazolyl, thiadiazolyl, benzothiazolyl, triazolyl, imidazolyl, benzimidazolyl and furanyl. Further, the substituents described above may be combined with each other to form a six-membered aryl ring or heterocycle.

The preferred form of the organic EL device of the present invention includes a device containing a reducing dopant in a region in which an electron is transported or an interfacial region between the cathode and the organic thin film layer. In this case, the reducing dopant is defined as a substance which can reduce an electron transporting compound. Accordingly, various compounds can be used as long as they have a fixed reducing property, and capable of being suitably used is, for example, at least one substance selected from the group consisting of alkali metals, alkali earth metals, rare earth metals, oxides of alkali metals, halides of alkali metals, oxides of alkali earth metals, halides of alkali earth metals, oxides of rare earth metals or halides of rare earth metals, organic complexes of alkali metals, organic complexes of alkali earth metals and organic complexes of rare earth metals.

To be more specific, the preferred reducing dopant includes at least one alkali metal selected from the group consisting of Na (work function: 2.36 eV), K (work function: 2.28 eV), Rb (work function: 2.16 eV) and Cs (work function: 1.95 eV) and at least one alkali earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, more preferred reducing dopant is at least one alkali metal selected from the group consisting of K, Rb and Cs, and it is more preferably Rb or Cs. It is most preferably Cs. The above alkali metals have a particularly high reducing ability, and addition of a relatively small amount thereof to the electron injecting zone provides a rise in a light emitting luminance and an extension in a life in the organic EL device. The combination of two or more kinds of the above alkali metals is preferred as the reducing dopant having a work function of 2.9 eV or less, and particularly preferred is the combination containing Cs, for example, Cs and Na, Cs and K, Cs and Rb or Cs, Na and K. Containing Cs in combination makes it possible to efficiently exhibit the reducing ability, and addition thereof to the electron injecting zone provides a rise in a light emitting luminance and an extension in a life in the organic EL device.

In the present invention, an electron injecting layer constituted from an insulator and a semiconductor may further be provided between the cathode and the organic layer. This makes it possible to effectively prevent an electric current from leaking and raise the electron injecting property. Preferably used as the above insulator is at least one metal compound selected from the group consisting of alkali metal chalcogenides, alkali earth metal chalcogenides, halides of alkali metals and halides of alkali earth metals. If the electron injecting layer is constituted from the above alkali metal chalcogenides, it is preferred in the point that the electron injecting property can further be enhanced. To be specific, the preferred alkali metal chalcogenides include, for example, Li$_2$O, LiO, Na$_2$S, Na$_2$Se and NaO, and the preferred alkali earth metal chalcogenides include, for example, CaO, BaO, SrO, BeO, BaS and CaSe. Also, the preferred halides of alkali metals include, for example, LiF, NaF, KF, LiCl, KCl and NaCl. The preferred halides of alkali earth metals include, for example, fluorides such as CaF$_2$, BaF$_2$, SrF$_2$, MgF$_2$ and BeF$_2$ and halides other than the fluorides.

The semiconductor constituting the electron transporting layer includes a single kind of oxides, nitrides or nitride oxides containing at least one element of Ba, Ca, Sr, Yb, Al, Ga, In, Li, Na, Cd, Mg, Si, Ta, Sb and Zn or combination of two or more kinds thereof. The inorganic compound constituting the electron transporting layer is preferably a microcrystalline or amorphous insulating thin film. If the electron transporting layer is constituted from the above insulating thin film, more homogeneous thin film is formed, and therefore picture element defects such as dark spots can be reduced. The above inorganic compound includes the alkali metal chalcogenides, the alkali earth metal chalcogenides, the halides of alkali metals and the halides of alkali earth metals each described above.

(7) Cathode

Substances using metals, alloys, electroconductive compounds and mixtures thereof each having a small work function (4 eV or less) for the electrode material are used as the cathode in order to inject electrons into the electron injecting and transporting layer or the luminescent layer. The specific examples of the above electrode material include sodium, sodium-potassium alloys, magnesium, lithium, magnesium-.silver alloys, aluminum/aluminum oxide, aluminum.lithium alloys, indium and rare earth metals.

The above cathode can be prepared by forming a thin film from the above electrode materials by a method such as deposition and sputtering.

In this respect, when light emitted from the luminescent layer is taken out from the cathode, a transmission factor of the cathode based on light emitted is preferably larger than 10%.

A sheet resistance of the cathode is preferably several hundred Ω/□ or less, and a film thickness thereof is usually 10 nm to 1 μm, preferably 50 to 200 nm.

(8) Insulating Layer

The organic EL device is liable to cause picture element defects by leak and short. In order to prevent this, an insulating thin film is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide, and mixtures and laminates thereof may be used.

(9) Production Process for Organic EL Device

According to the materials and the forming methods which have been exemplified above, the anode, the luminescent layer, if necessary, the hole injecting and transporting layer and, if necessary, the electro injecting and transporting layer are formed, and further the cathode is formed, whereby the organic EL device can be prepared. Also, the organic EL device can be prepared as well from the cathode to the anode in an order which is reverse to what was described above.

A preparation example of an organic EL device having a structure in which an anode/a hole injecting layer/a luminescent layer/an electron injecting layer/a cathode are provided in order on a light transmitting substrate shall be described below.

First, a thin film comprising an anode material is formed on a suitable light transmitting substrate by a method such as deposition and sputtering so that a film thickness falls in a range of 1 μm or less, preferably 10 to 200 nm, whereby an anode is prepared. Next, a hole injecting layer is provided on this anode. The hole injecting layer can be formed, as described above, by a method such as a vacuum deposition method, a spin coating method, a casting method and an LB method, and it is preferably formed by the vacuum deposition method from the viewpoints that the homogeneous film is liable to be obtained and that pinholes are less liable to be produced. When forming the hole injecting layer by the vacuum deposition method, the depositing conditions thereof are varied according to the compounds used (materials for the hole injecting layer) and the crystal structure of the targeted hole injecting layer, and in general, they are suitably selected preferably in the ranges of a depositing source temperature of 50 to 450° C., a vacuum degree of $10^{-7}$ to $10^{-3}$ torr, a depositing speed of 0.01 to 50 nm/second, a substrate temperature of −50 to 300° C. and a film thickness of 5 nm to 5 μm.

Next, a luminescent layer can be formed on the hole injecting layer by making a thin film from the desired organic luminescent material by a method such as a vacuum deposition method, sputtering, a spin coating method and a casting method, and it is preferably formed by the vacuum deposition method from the viewpoints that the homogeneous film is liable to be obtained and that pinholes are less liable to be produced. When forming the luminescent layer by the vacuum deposition method, the depositing conditions thereof are varied according to the compounds used, and in general, they can be selected from the same condition ranges as in the hole injecting layer.

Next, an electron injecting layer is provided on the above luminescent layer. It is preferably formed by the vacuum deposition method as is the case with the hole injecting layer and the luminescent layer since the homogeneous film has to be obtained. The depositing conditions thereof can be selected from the same condition ranges as in the hole injecting layer and the luminescent layer.

The aromatic triamine compound of the present invention can be codeposited together with the other materials, though varied depending on that it is added to any layer in the luminescent zone and the hole injecting zone, when using the vacuum deposition method. When using the spin coating method, it can be added by mixing with the other materials.

Lastly, a cathode is laminated, whereby an organic EL device can be obtained.

The cathode is constituted from metal, and therefore the deposition method and the sputtering method can be used. However, the vacuum deposition method is preferred in order to protect the organic substance layer of the base from being damaged in making the film.

The above organic EL device is preferably prepared serially from the anode up to the cathode in one vacuuming.

The forming methods of the respective layers in the organic EL device of the present invention shall not specifically be restricted, and the forming methods carried out by the vacuum deposition method and the spin coating method which have so far publicly been known can be used. The organic thin film containing the compound represented by Formula (1) described above which is used for the organic EL device of the present invention can be formed by a publicly known method carried out by a coating method such as a vacuum deposition method, a molecular beam evaporation method (MBE method), a dipping method using a solution prepared by dissolving the compound in a solvent, a spin coating method, a casting method, a bar coating method and a roll coating method.

The film thicknesses of the respective organic layers in the organic EL device of the present invention shall not specifically be restricted, and in general, if the film thickness is too small, defects such as pinholes are liable to be caused. On the other hand, if it is too large, high voltage has to be applied, and the efficiency is deteriorated, so that it falls preferably in a range of several nm to 1 μm.

When applying a direct voltage to the organic EL device, luminescence can be observed by applying a voltage of 5 to 40 V setting a polarity of the anode to plus and that of the cathode to minus. An electric current does not flow only by applying a voltage at a reverse polarity, and luminescence is not caused at all. Further, when applying an AC voltage, uniform luminescence can be observed only when the anode has a plus polarity and the cathode has a minus polarity. The waveform of an alternating current applied may be optional.

EXAMPLES

Next, the present invention shall be explained in further details with reference to examples.

Synthetic Example 1

Synthesis of Aromatic Triamine Compound 1

The following compound 1 was synthesized by the following reaction process:

(1) Synthesis of 4,4"-dibromo-p-terphenyl

Toluene 600 ml and a 2M sodium carbonate aqueous solution 300 ml were added to 1,4-diiodobenzene 33.0 g, 4-bromophenylboronic acid 48.2 g and tetrakis(triphenylphosphine)palladium (0) 4.62 g under argon atmosphere, and the mixture was refluxed for 10 hours under heating.

After finishing the reaction, the mixture was immediately filtered, and the aqueous layer was removed. The organic layer was dried on sodium sulfate and then concentrated. A solid matter thus obtained was recrystallized from toluene to obtain 32.6 g of white crystal of 4,4"-dibromo-p-terphenyl (yield: 84%)

(2) Synthesis of 4-bromo-4"-diphenylamino-p-terphenyl

Charged under argon flow were N,N-diphenylamine 10.6 g, 4,4"-dibromo-p-terphenyl 24.3 g, potassium carbonate 13.0 g, copper powder 0.400 g and decalin 40 ml, and they were reacted at 200° C. for 6 days.

After finishing the reaction, the mixture was filtered while kept hot, and the insoluble matter was washed with toluene. The filtrates were put together and concentrated. Toluene 30 ml was added to the residue to remove deposited crystal by filtering, and the filtrate was concentrated. Then, methanol 100 ml was added to the residue, and after stirring, the supernatant was disposed. Further, 30 ml of methanol was added thereto, and after stirring, the supernatant was disposed to carry out column refining, whereby yellow powder was obtained. This was dissolved in 15 ml of toluene under heat-

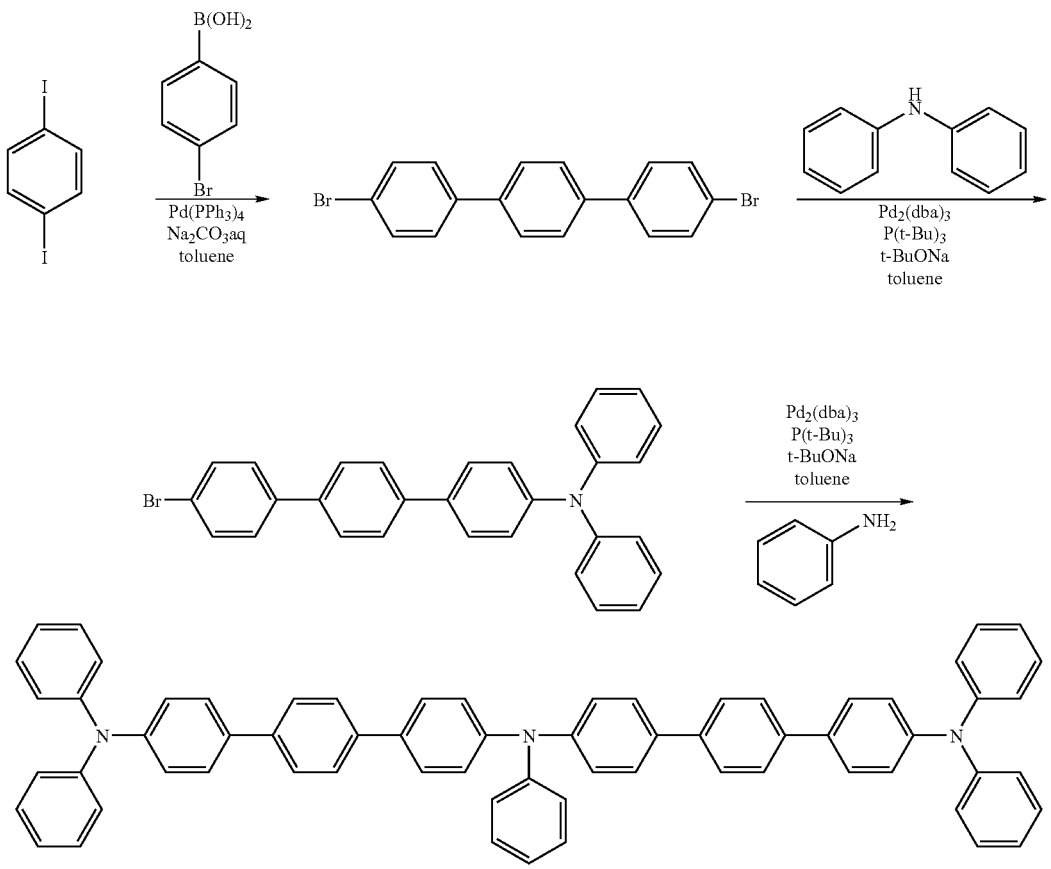

ing, and 15 ml of hexane was added and cooled down to filter deposited crystal, whereby 13.4 g of 4-bromo-4"-diphenylamino-p-terphenyl was obtained.

(3) Synthesis of 4-diphenylamino-4"-N-phenylamino-p-terphenyl

A 0.66 weight % toluene solution 100 μl of tri-t-butylphosphine was added to a toluene 100 ml solution of 4-bromo-4"-diphenylamino-p-terphenyl 10.0 g, aniline 2.35 g, tris(benzylideneacetone)-dipalladium (0) 192 mg and t-butoxysodium 2.82 g under Ar atmosphere, and the mixture was stirred at room temperature for 5 hours. The mixture was filtered through celite, and the filtrate was extracted with toluene. This was concentrated under reduced pressure, and the resulting crude product was subjected to column refining to obtain 8.02 g of pale yellow powder.

(4) Synthesis of Compound 1

A 0.66 weight % toluene solution 190 μl of tri-t-butylphosphine was added to a toluene 100 ml solution of 4-diphenylamino-4"-N-phenylamino-p-terphenyl 8.00 g, aniline 0.710 g, tris(benzylideneacetone)dipalladium (0) 350 mg and s t-butoxysodium 2.05 g under Ar atmosphere, and the mixture was refluxed for 5 hours under heating. After cooled down to room temperature, the mixture was filtered through celite, and the filtrate was extracted with toluene. This was concentrated under reduced pressure, and the resulting crude product was subjected to column refining to obtain 6.21 g of pale yellow powder. This compound was analyzed by a mass spectrum to result in finding that it was the targeted product and that m/e was 883 versus a molecular weight of 883.39.

Synthetic Example 2 synthesis of Aromatic Triamine Compound 2

The following compound 2 was synthesized by the following reaction process:

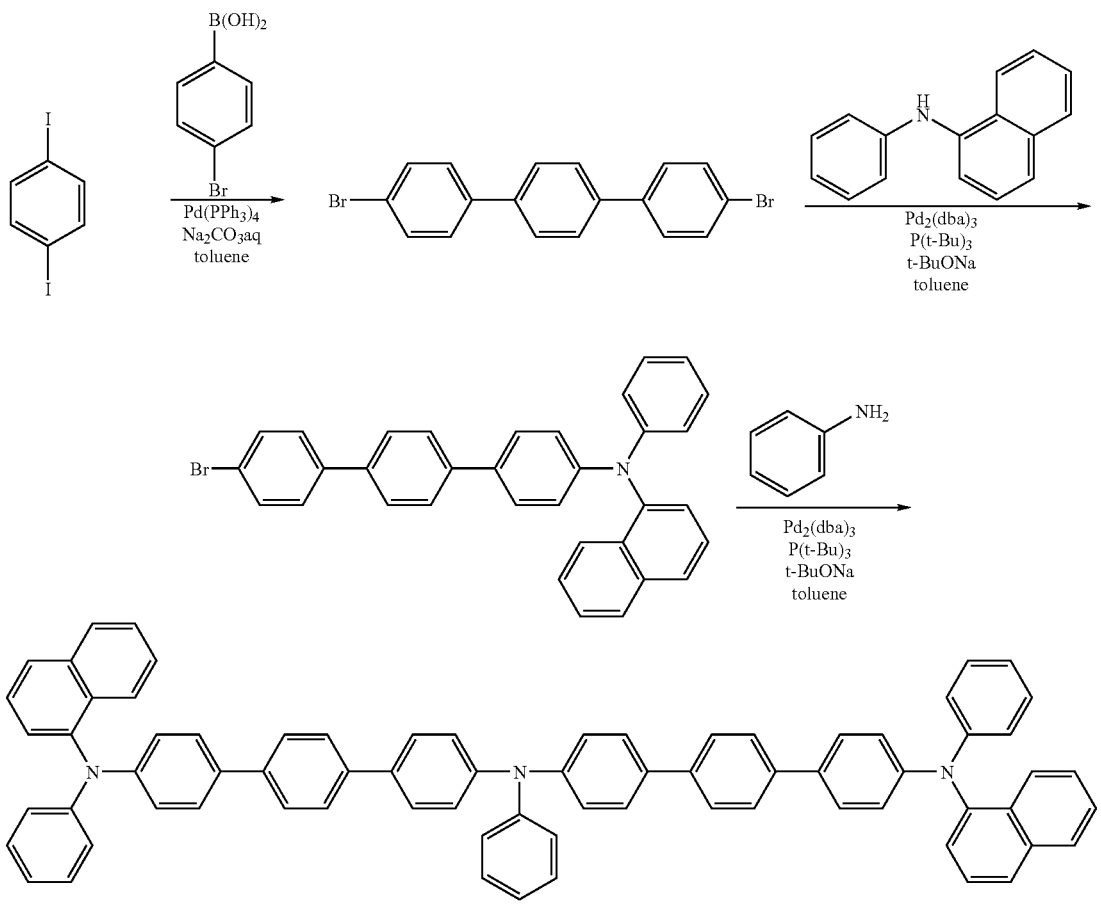

2

The compound 2 was synthesized by the same method, except that in Synthetic Example 1, N-phenyl-1-naphthylamine was used in place of N,N-diphenylamine. This compound was analyzed by a mass spectrum to result in finding that it was the targeted product and that m/e was 983 versus a molecular weight of 983.42.

Synthetic Example 3

Synthesis of Aromatic Triamine Compound 3

The following compound 3 was synthesized by the following reaction process:

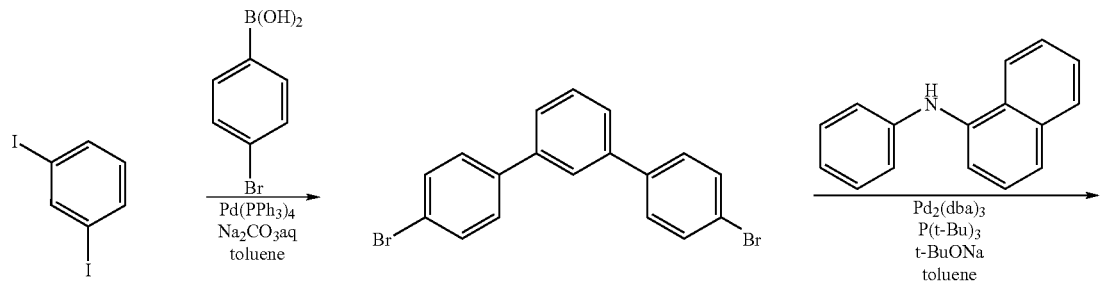

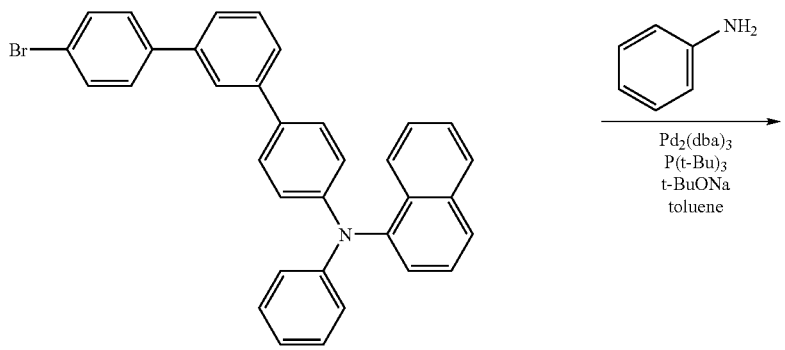

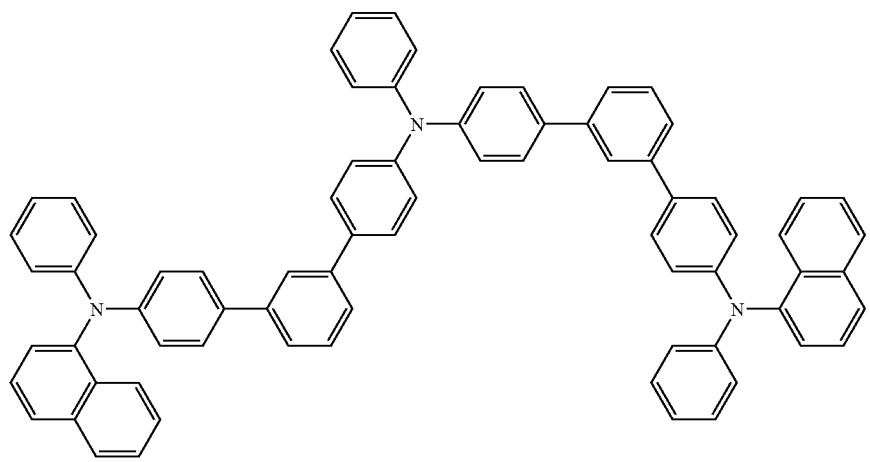

3

The compound 3 was synthesized by the same method, except that in Synthetic Example 2, 1,3-diiodobenzene was used in place of 1,4-diiodobenzene. This compound was analyzed by a mass spectrum to result in finding that it was the targeted product and that m/e was 983 versus a molecular weight of 983.42.

Synthetic Example 4

Synthesis of Aromatic Triamine Compound 4

The following compound 4 was synthesized by the following reaction process:

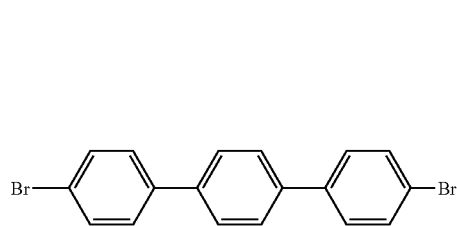 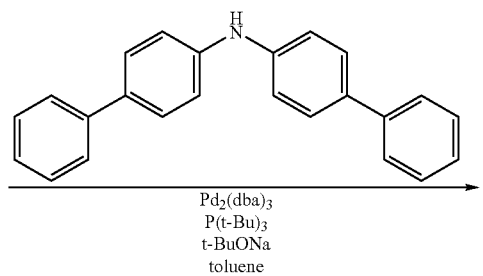

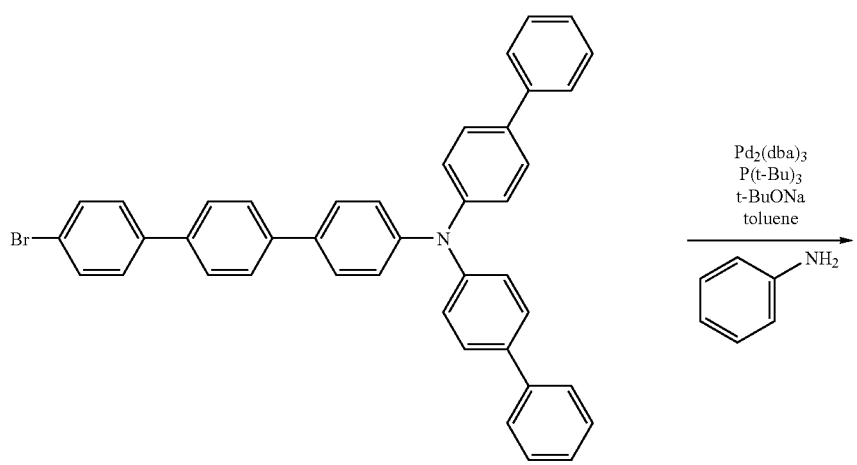

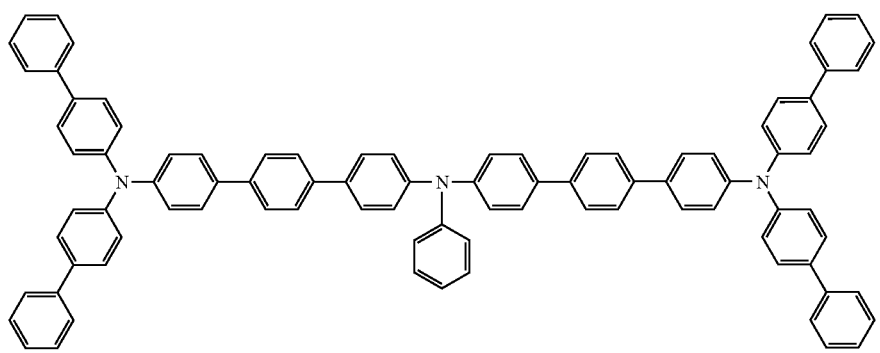

4

The compound 4 was synthesized by the same method, except that in Synthetic Example 1, bis(4-biphenyl)amine was used in place of N,N-diphenylamine. This compound was analyzed by a mass spectrum to result in finding that it was the targeted product and that m/e was 1187 versus a molecular weight of 1187.52.

Synthetic Example 5

Synthesis of Aromatic Triamine Compound 5

The following compound 5 was synthesized by the following reaction process:

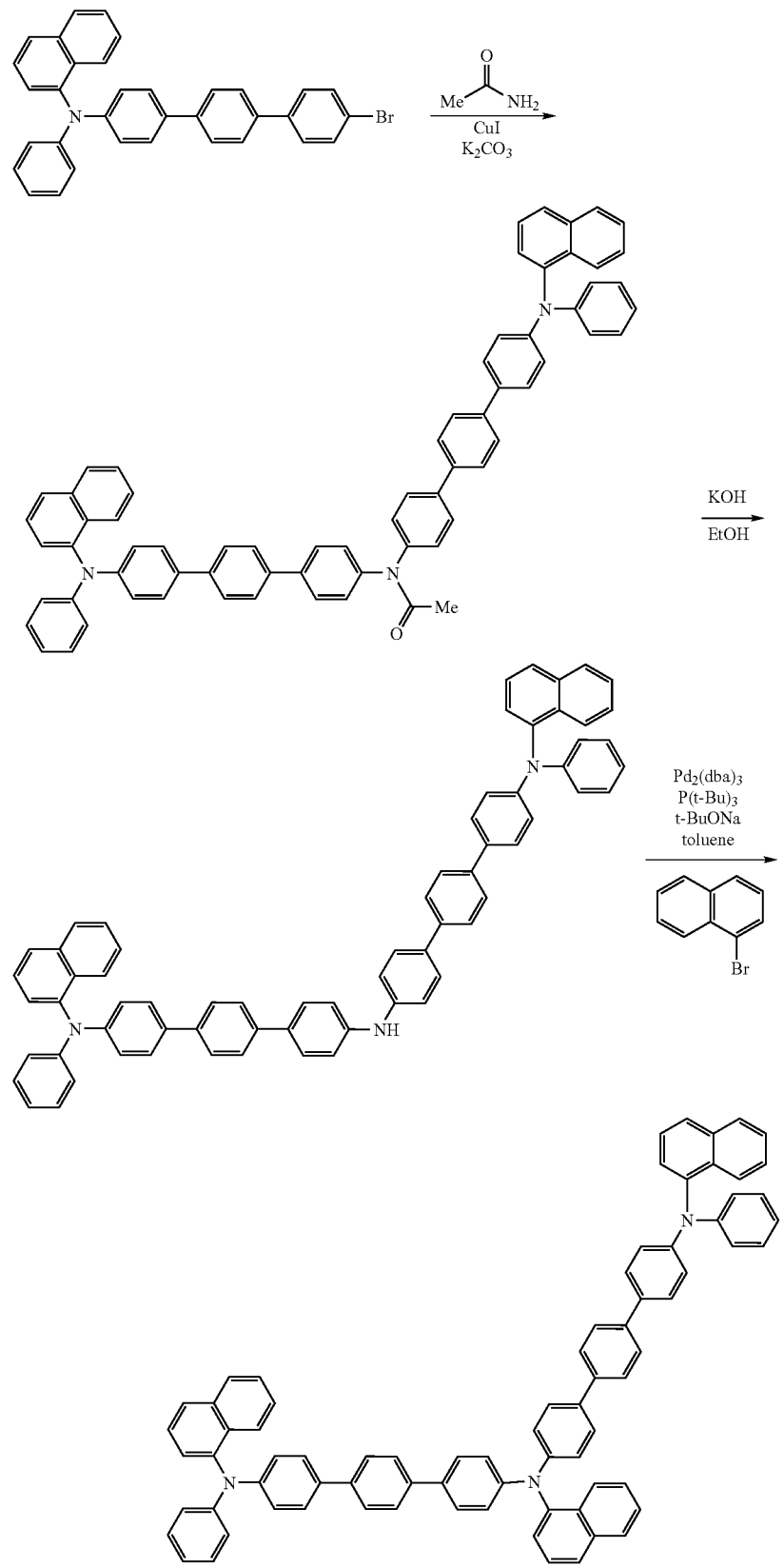

(1) Synthesis of N,N-bis[4"-(N-phenyl-1-naphthylamino)-p-terphenyl-4-yl]acetamide Charged were 4-bromo-4"-(N-phenyl-1-naphthylamino)-p-terphenyl 105 g, acetamide 5.90 g, copper iodide 0.95 g, potassium carbonate 276 g, N,N'-dimethylethylenediamine 0.88 g and decalin 1 L, and the mixture was heated and refluxed for 6 days under argon atmosphere. After finishing the reaction, the insoluble matter was filtered. The insoluble matter was washed with hot toluene and dichloromethane, and the filtrates were put together and concentrated. The solid matter thus obtained was washed with methanol and then recrystallized from toluene to obtain 82.0 g of white crystal of N,N-bis[4"-(N-phenyl-1-naphthylamino)-p-terphenyl-4-yl]acetamide.

(2) Synthesis of N,N-bis[4"-(N-phenyl-1-naphthylamino)-p-terphenyl-4-yl]amine

Charged were N,N-bis[4"-(N-phenyl-1-naphthylamino)-p-terphenyl-4-yl]acetamide 82.0 g, a 50% potassium hydroxide aqueous solution 39 g and diethylbenzene 100 ml, and the mixture was heated and refluxed for 3 days. After finishing the reaction, the mixture was left cooling down, and water 100 ml and hexane 500 ml were added thereto. The brown solid matter deposited was filtered off and dried under reduced pressure to obtain 67 g of N,N-bis[4"-(N-phenyl-1-naphthylamino)-p-terphenyl-4-yl]amine.

(3) Synthesis of Compound 5

A 0.66 weight % toluene solution 100 µl of tri-t-butylphosphine was added to a toluene 100 ml solution of N,N-bis[4"-(N-phenyl-1-naphthylamino)-p-terphenyl-4-yl]amine 9.08 g, 1-bromonaphthalene 2.48 g, tris(benzylideneacetone)dipalladium (0) 183 mg and t-butoxysodium 1.35 g, and the mixture was refluxed for 5 hours under heating. After cooled down to room temperature, the mixture was filtered through celite, and the filtrate was extracted with toluene. This was concentrated under reduced pressure, and the resulting crude product was subjected to column refining to obtain 5.20 g of pale yellow powder. This compound was analyzed by a mass spectrum to result in finding that it was the targeted product and that m/e was 1033 versus a molecular weight of 1033.44.

Synthetic Example 6

Synthesis of Aromatic Triamine Compound 6

The following compound 6 was synthesized by the following reaction process:

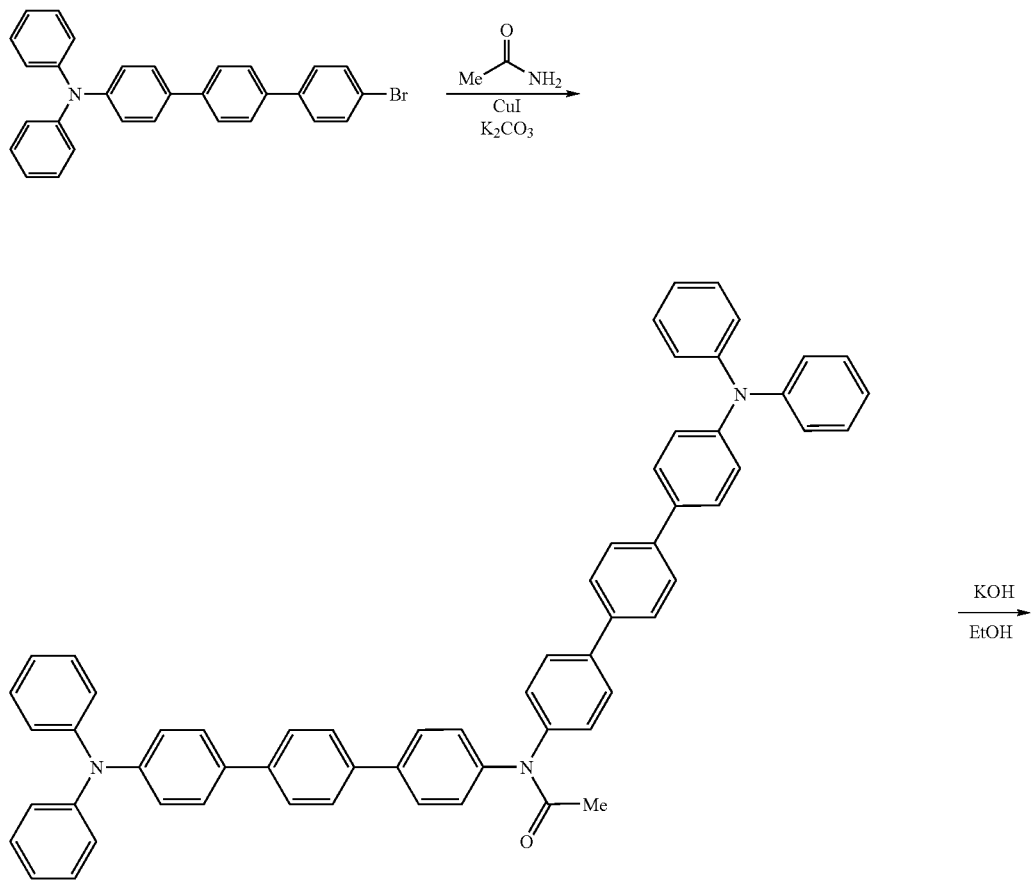

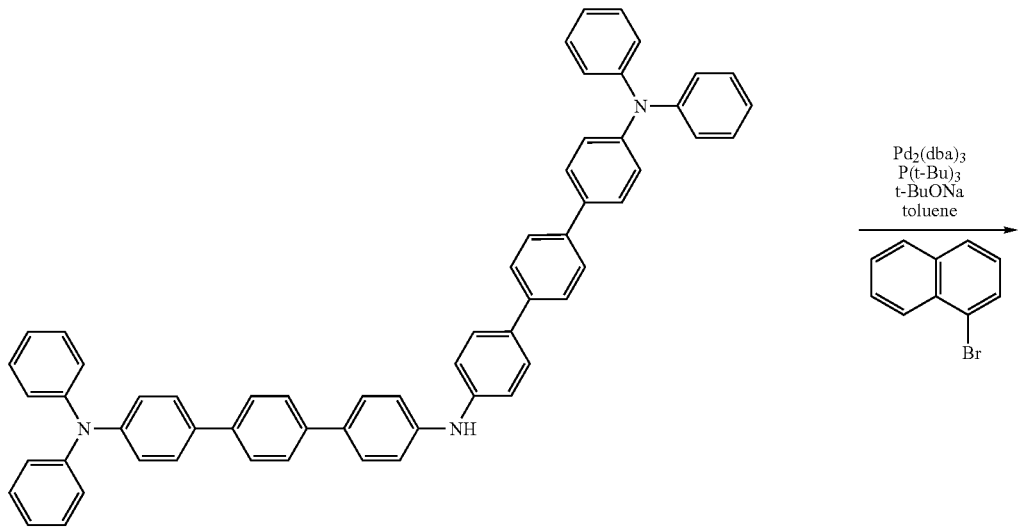

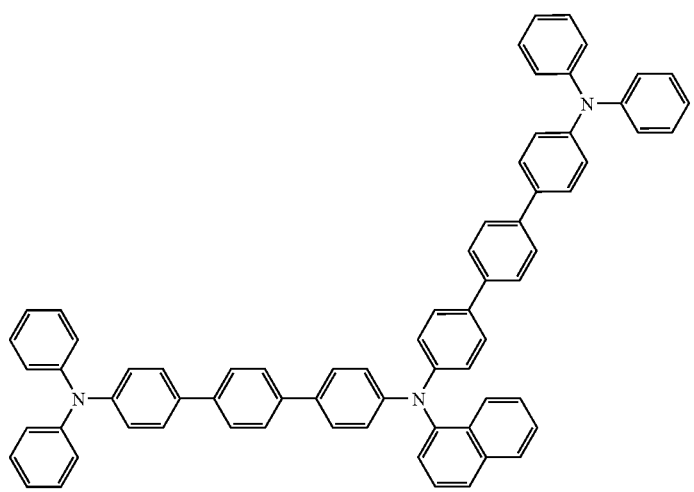

6

The compound 6 was synthesized by the same method, except that in Synthetic Example 5, 4-bromo-4"-(N,N-diphenylamino)-p-terphenyl was used in place of 4-bromo-4"-(N-phenyl-1-naphthylamino)-p-terphenyl. This compound was analyzed by a mass spectrum to result in finding that it was the targeted product and that m/e was 933 versus a molecular weight of 933.41.

Synthetic Example 7

Synthesis of Aromatic Triamine Compound 7

The following compound 7 was synthesized by the following reaction process:

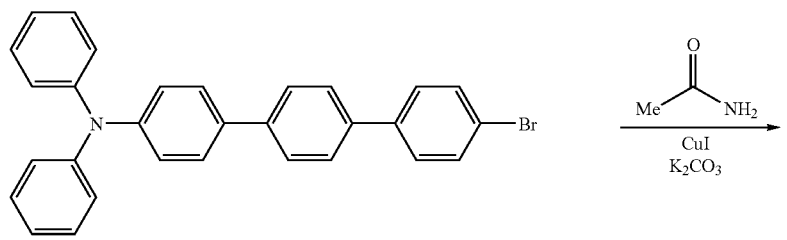
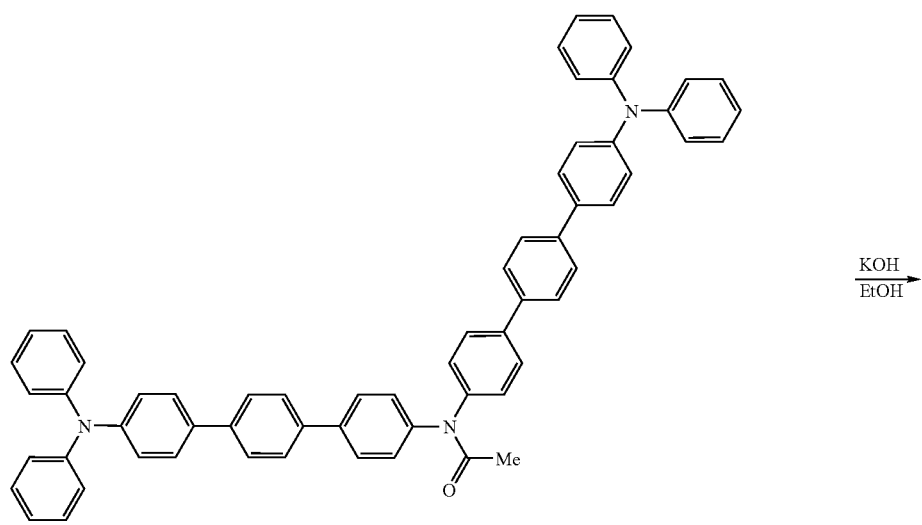
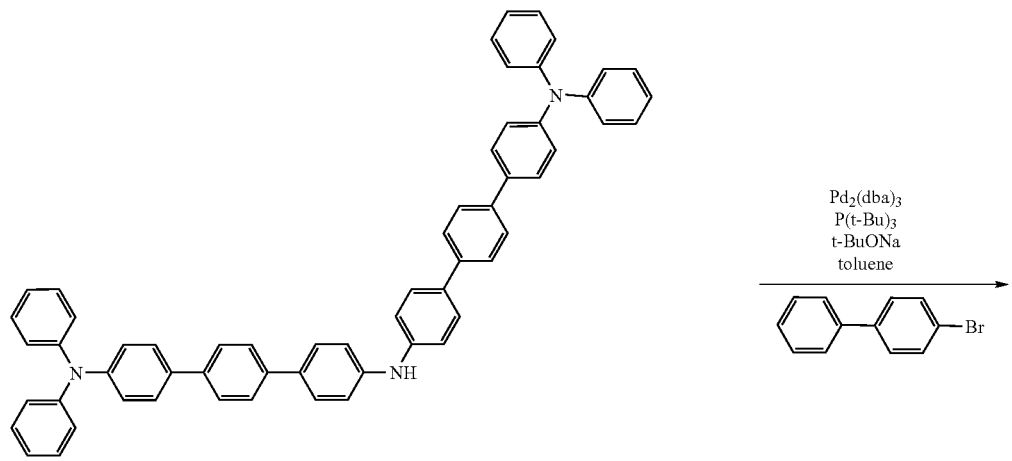

-continued

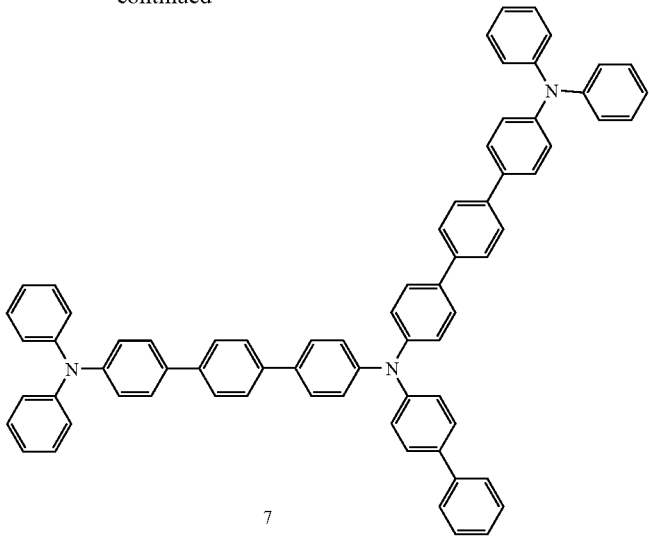

7

The compound 7 was synthesized by the same method, except that in Synthetic Example 6, 4-bromobiphenyl was used in place of 1-bromonaphthalene. This compound was analyzed by a mass spectrum to result in finding that it was the targeted product and that m/e was 959 versus a molecular weight of 959.42.

Synthetic Example 8

Synthesis of Aromatic Triamine Compound 8

The following compound 8 was synthesized by the following reaction process:

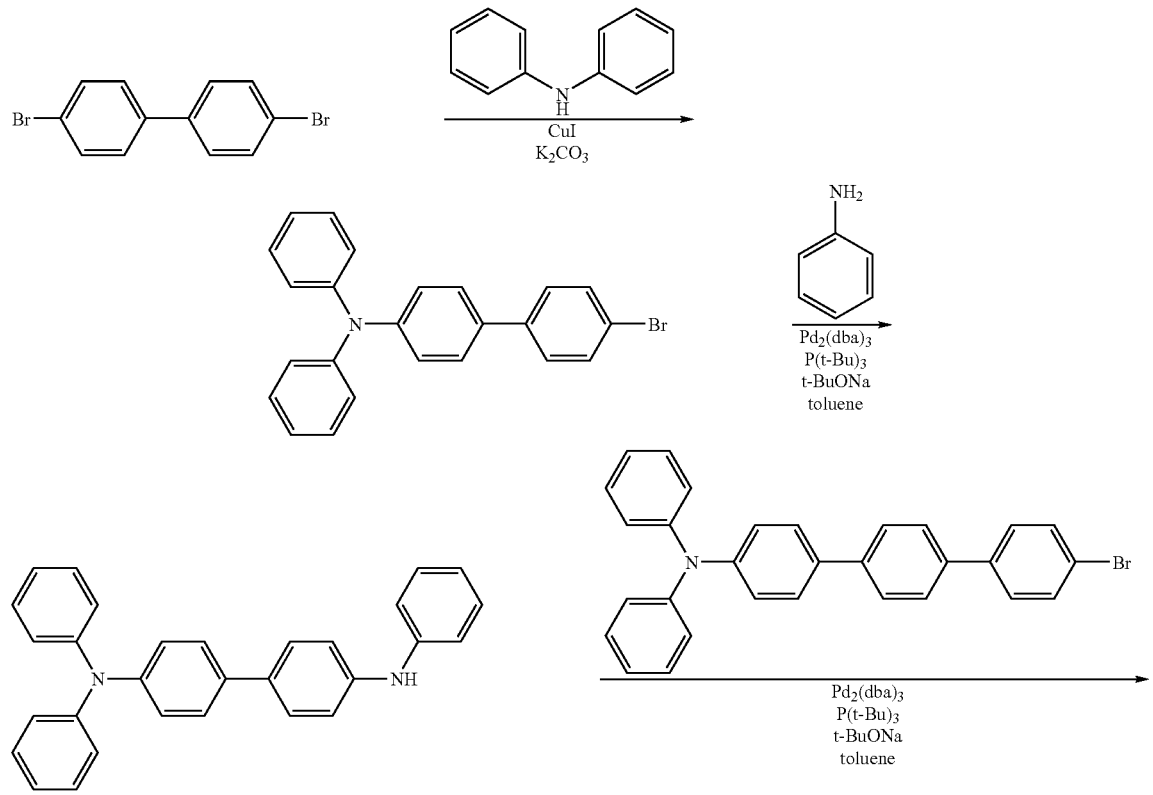

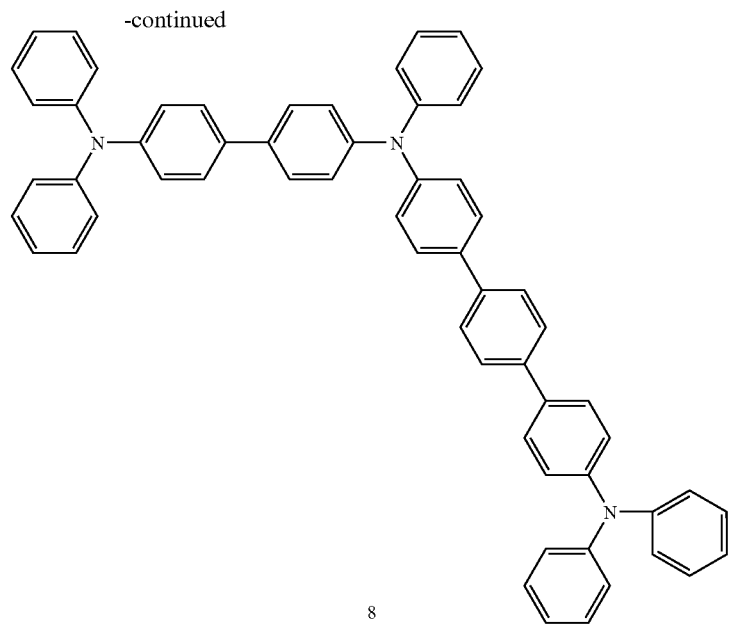

8

(1) Synthesis of 4-bromo-4'-(N,N-diphenylamino)biphenyl

Charged under argon flow were N,N-diphenylamine 10.6 g, 4,4''-dibromobiphenyl 19.5 g, potassium carbonate 13.0 g, copper powder 0.400 g and decalin 40 ml, and they were reacted at 200° C. for 6 days.

After finishing the reaction, the mixture was filtered while kept hot, and the insoluble matter was washed with toluene. The filtrates were put together and concentrated. Toluene 30 ml was added to the residue to remove deposited crystal by filtering, and the filtrate was concentrated. Then, methanol 100 ml was added to the residue, and after stirring, the supernatant was disposed. Further, 30 ml of methanol was added thereto, and after stirring, the supernatant was disposed to carry out column refining, whereby yellow powder was obtained. This was dissolved in 15 ml of toluene under heating, and 15 ml of hexane was added thereto and cooled down to filter deposited crystal, whereby 13.4 g of 4-bromo-4'-(N, N-diphenylamino)biphenyl was obtained.

(8-2) Synthesis of N,N,N'-triphenylbenzidine

A 0.66 weight % toluene solution 100 μl of tri-t-butylphosphine was added to a toluene 100 ml solution of 4-bromo-4'-(N,N-diphenylamino)biphenyl 4.00 g, aniline 1.11 g, tris(benzylideneacetone)-dipalladium (0) 183 mg and t-butoxysodium 1.35 g, and the mixture was stirred at room temperature for 5 hours. After finishing the reaction, the mixture was filtered through celite, and the filtrate was extracted with toluene. This was concentrated under reduced pressure, and the resulting crude product was subjected to column refining to obtain 3.20 g of pale yellow powder of N,N,N'-triphenylbenzidine.

(8-3) Synthesis of Compound 8

A 0.66 weight % toluene solution 50 μl of tri-t-butylphosphine was added to a toluene 100 ml solution of 4-bromo-4''-diphenylamino-p-terphenyl 2.38 g, N,N,N'-triphenylbenzidine 2.48 g, tris(benzylideneacetone)dipalladium (0) 92 mg and t-butoxysodium 0.67 g, and the mixture was refluxed for 5 hours under heating. After cooled down to room temperature, the mixture was filtered through celite, and the filtrate was extracted with toluene. This was concentrated under reduced pressure, and the resulting crude product was subjected to column refining to obtain 3.20 g of pale yellow powder. This compound was analyzed by a mass spectrum to result in finding that it was the targeted product and that m/e was 807 versus a molecular weight of 807.36.

Synthetic Example 9

Synthesis of Aromatic Triamine Compound 9

The following compound 9 was synthesized by the following reaction process:

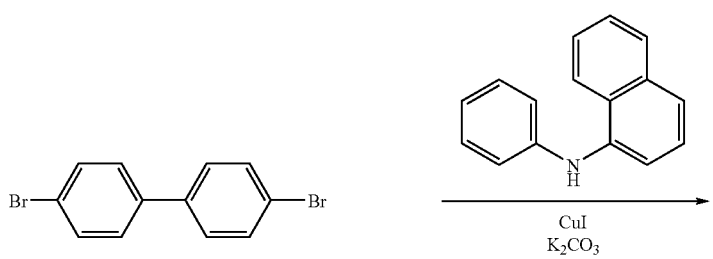

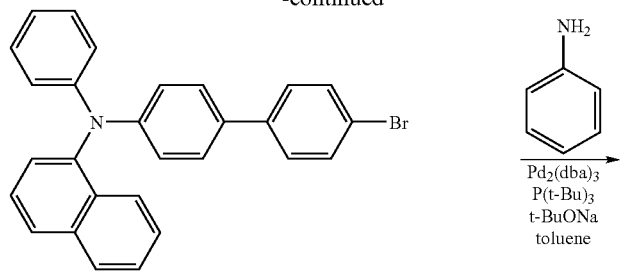

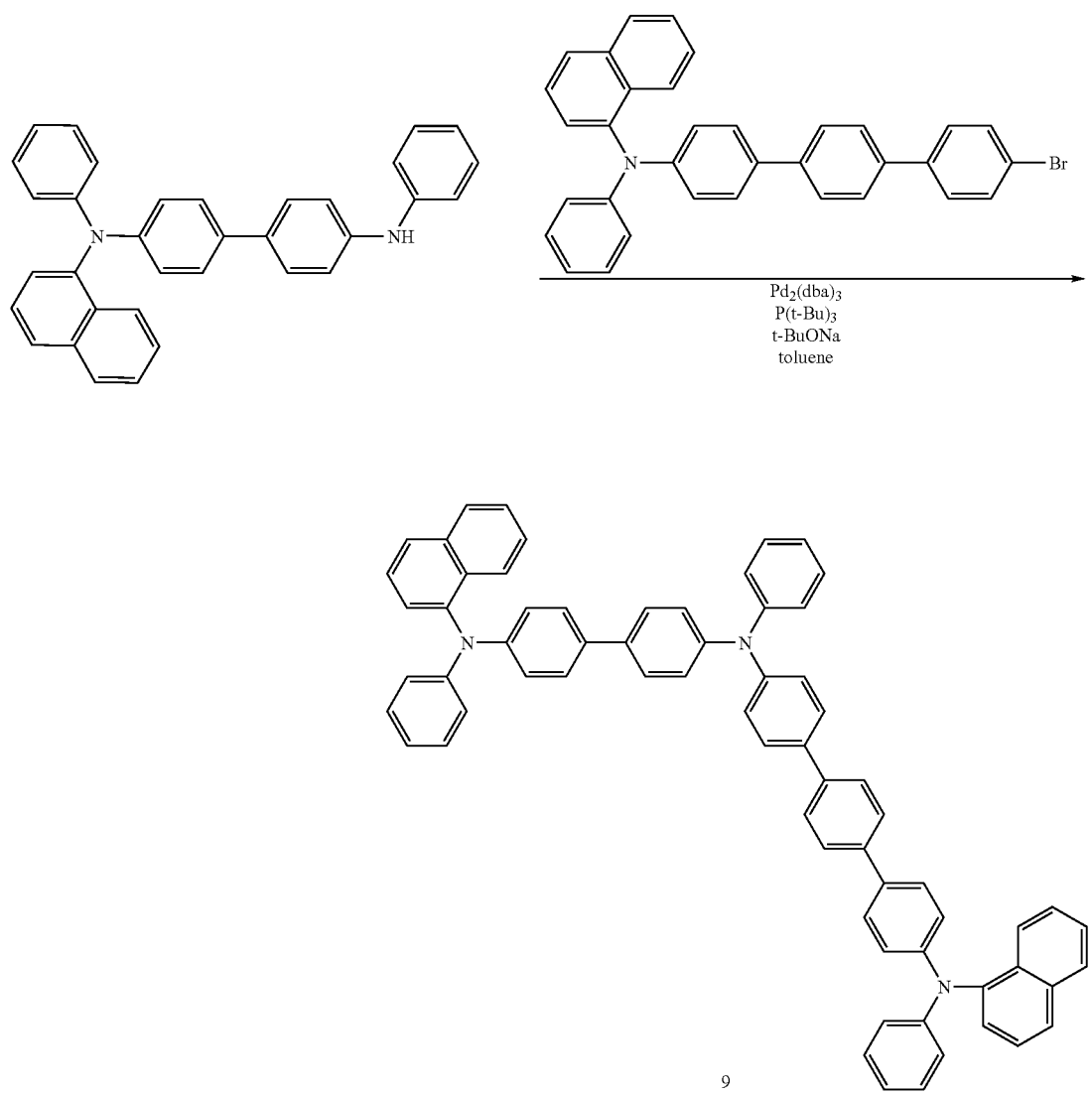

The compound 9 was synthesized by the same method, except that in Synthetic Example 8, N-phenyl-1-naphthylamine was used in place of N,N-diphenylamine. This compound was analyzed by a mass spectrum to result in finding that it was the targeted product and that m/e was 907 versus a molecular weight of 907.39.

Synthetic Example 10

Synthesis of Aromatic Triamine Compound 10

The following compound 10 was synthesized by the following reaction process:

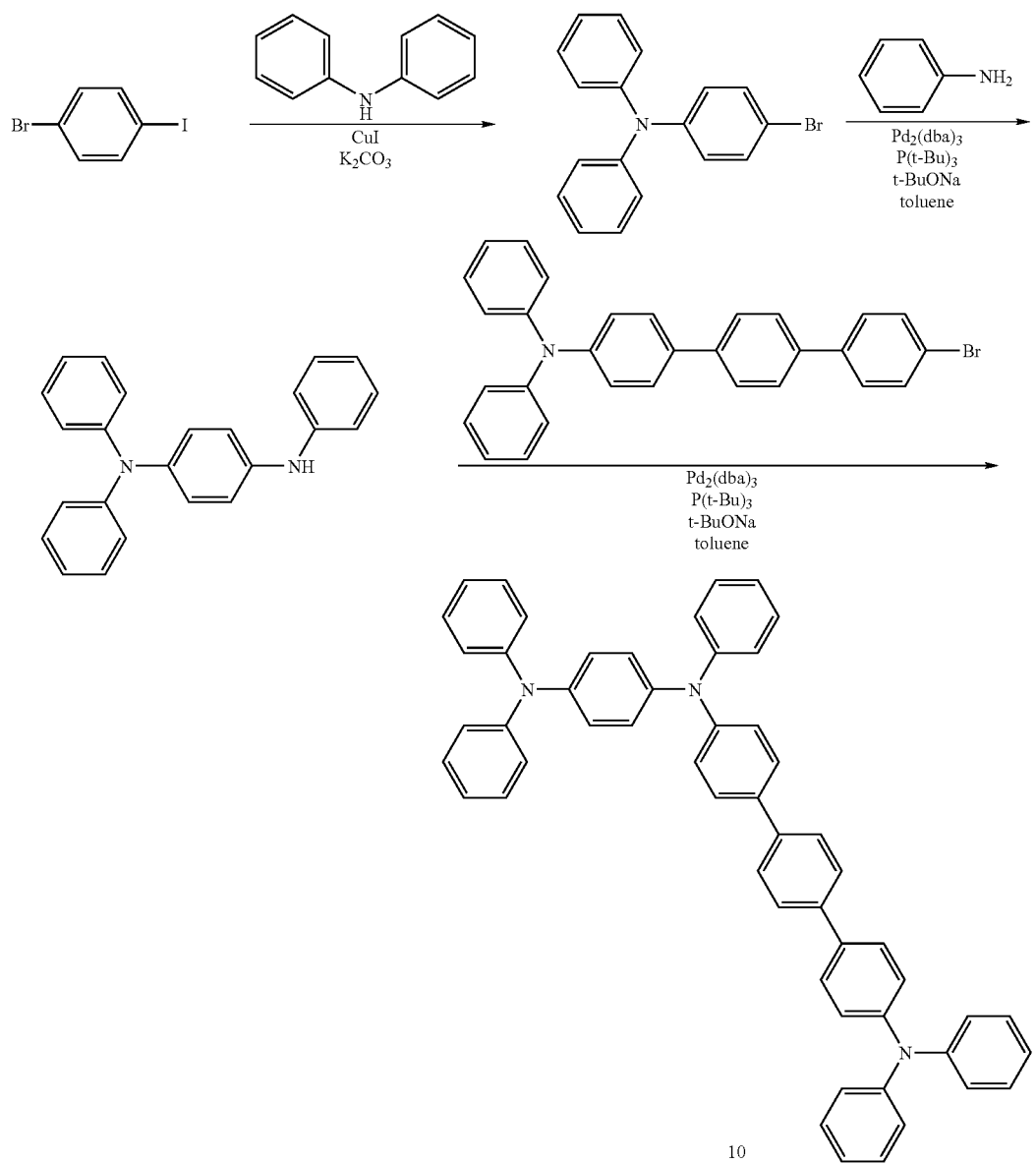

(1) Synthesis of 4-bromo-triphenylamine

Charged under argon flow were N,N-diphenylamine 10.6 g, p-bromoiodobenzene 14.8 g, potassium carbonate 14.4 g, copper powder 0.500 g and decalin 40 ml, and they were reacted at 200° C. for 6 days.

After finishing the reaction, the mixture was filtered while kept hot, and the insoluble matter was washed with toluene. The filtrates were put together and concentrated. Toluene 30 ml was added to the residue to remove deposited crystal by filtering, and the filtrate was concentrated. Then, methanol 100 ml was added to the residue, and after stirring, the supernatant was disposed. Further, 30 ml of methanol was added thereto, and after stirring, the supernatant was disposed to carry out column refining, whereby yellow powder was obtained. This was dissolved in 15 ml of toluene under heating, and 15 ml of hexane was added thereto and cooled down to filter deposited crystal, whereby 10.8 g of 4-bromo-triphenylamine was obtained.

(2) Synthesis of N,N,N'-triphenyl-1,4-phenylenediamine

A 0.66 weight % toluene solution 150 μl of tri-t-butylphosphine was added to a toluene 50 ml solution of 4-bromo-triphenylamine 5.00 g, aniline 1.72 g, tris(benzylideneacetone)dipalladium (0) 282 mg and t-butoxysodium 2.07 g, and the mixture was stirred at room temperature for 5 hours. After finishing the reaction, the mixture was filtered through celite, and the filtrate was extracted with toluene. This was concentrated under reduced pressure, and the resulting crude product was subjected to column refining to obtain 4.20 g of pale yellow powder of N,N,N'-triphenyl-1,4-phenylenediamine.

(3) Synthesis of Compound 10

A 0.66 weight % toluene solution 50 μl of tri-t-butylphosphine was added to a toluene 100 ml solution of 4-bromo-4"-diphenylamino-p-terphenyl 2.38 g, N,N,N'-triphenyl-1,4-phenylenediamine 2.01 g, tris(benzylideneacetone)dipalladium (0) 92 mg and t-butoxysodium 0.67 g, and the mixture was refluxed for 5 hours under heating. After cooled down to room temperature, the mixture was filtered through celite, and the filtrate was extracted with toluene. This was concentrated under reduced pressure, and the resulting crude product was subjected to column refining to obtain 2.50 g of pale yellow powder. This compound was analyzed by a mass spectrum to result in finding that it was the targeted product and that m/e was 731 versus a molecular weight of 731.33.

Synthetic Example 11

Synthesis of Aromatic Triamine Compound 11

The following compound 11 was synthesized by the following reaction process:

The compound 11 was synthesized by the same method, except that in Synthetic Example 10, N-phenyl-1-naphthylamine was used in place of N,N-diphenylamine. This compound was analyzed by a mass spectrum to result in finding that it was the targeted product and that m/e was 831 versus a molecular weight of 831.36.

Synthetic Example 12

Synthesis of Aromatic Triamine Compound 12

The following compound 12 was synthesized by the following reaction process:

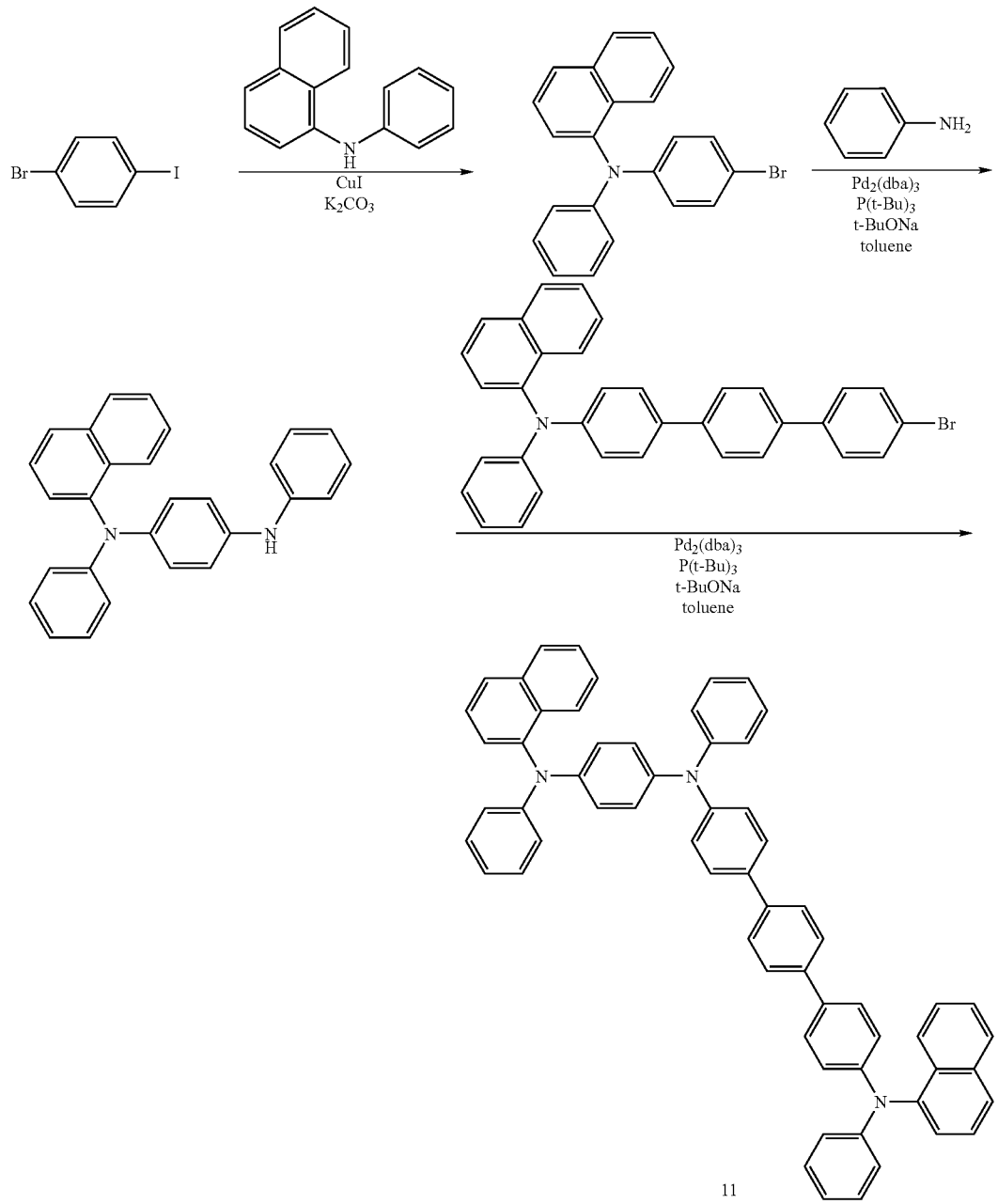

11

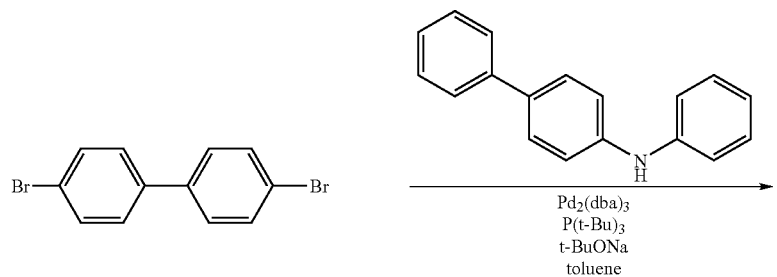
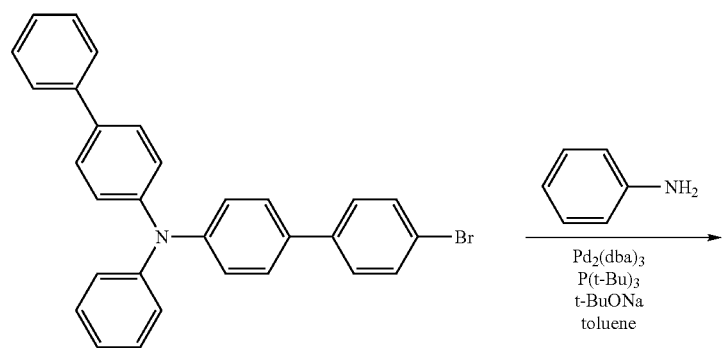
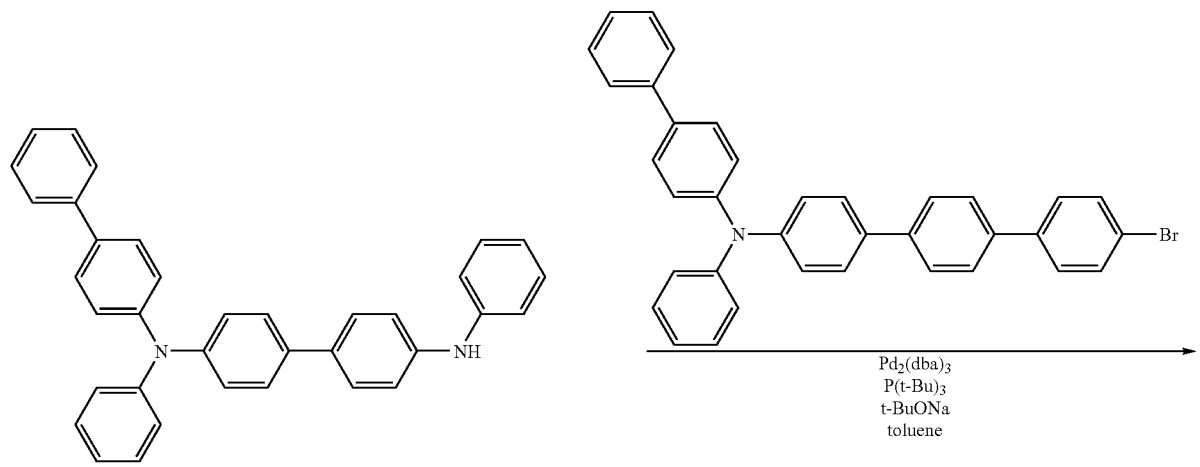

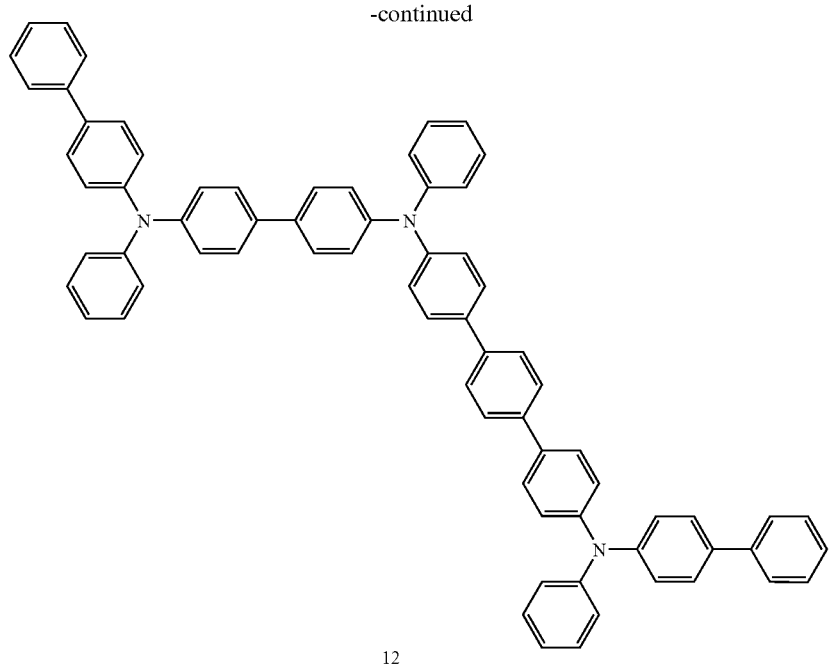

12

The compound 12 was synthesized by the same method, except that in Synthetic Example 8, (4-biphenyl)phenylamine was used in place of N,N-diphenylamine. This compound was analyzed by a mass spectrum to result in finding that it was the targeted product and that m/e was 959 versus a molecular weight of 959.42.

Synthetic Example 13

Synthesis of Aromatic Triamine Compound 13

The following compound 13 was synthesized by the following reaction process:

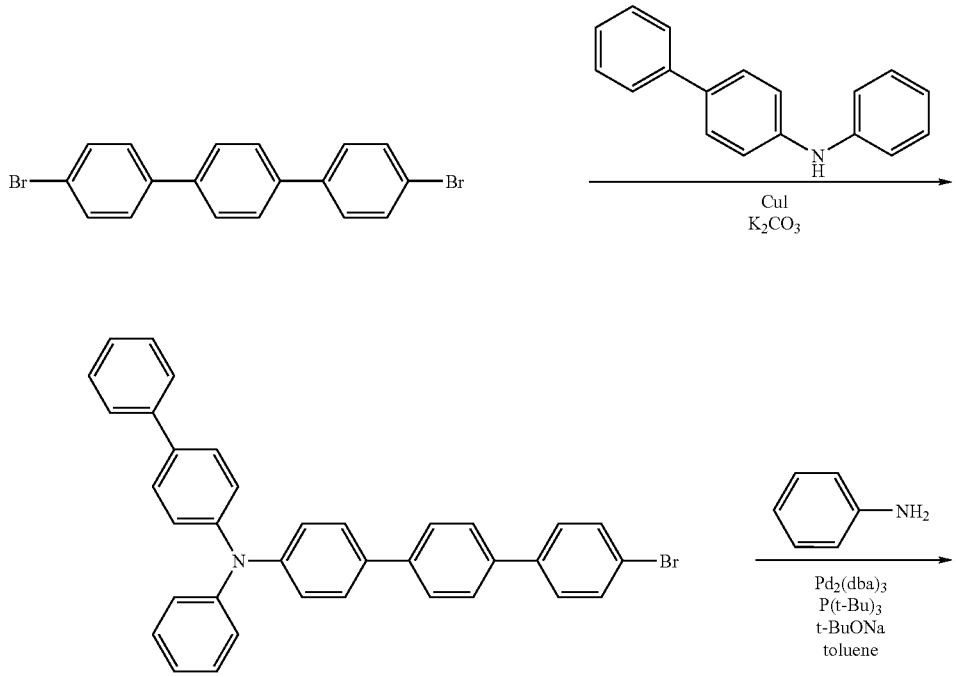

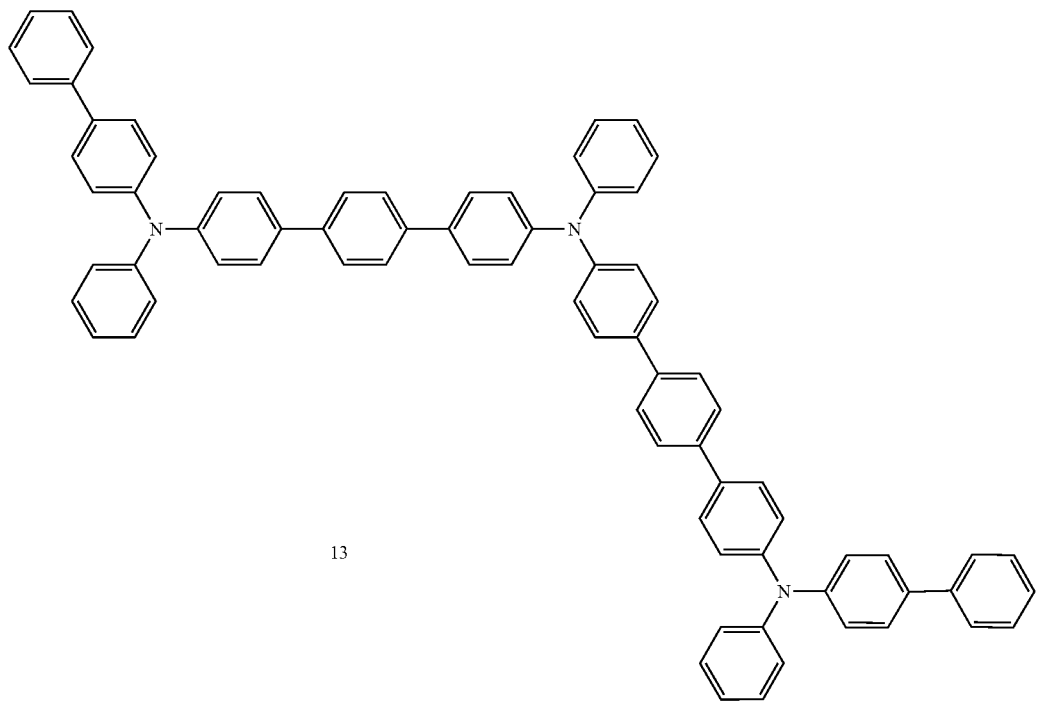

13

The compound 13 was synthesized by the same method, except that in Synthetic Example 1, (4-biphenyl)phenylamine was used in place of N,N-diphenylamine. This compound was analyzed by a mass spectrum to result in finding that it was the targeted product and that m/e was 1035 versus a molecular weight of 1035.46.

Synthetic Example 14

Synthesis of Aromatic Triamine Compound 14

The following compound 14 was synthesized by the following reaction process:

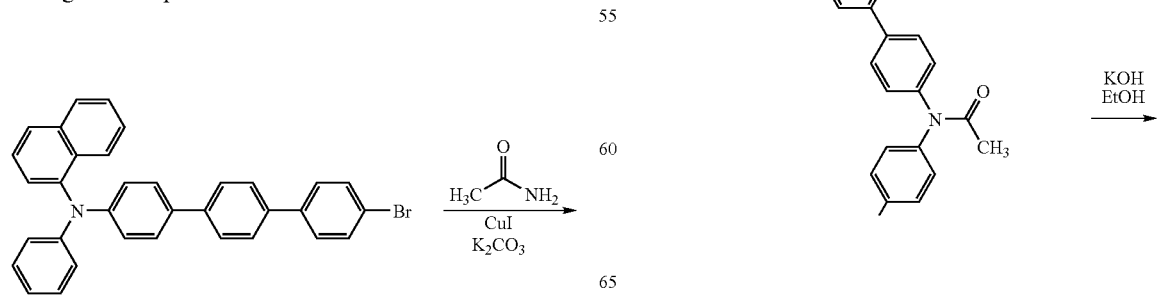

-continued

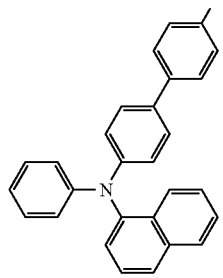

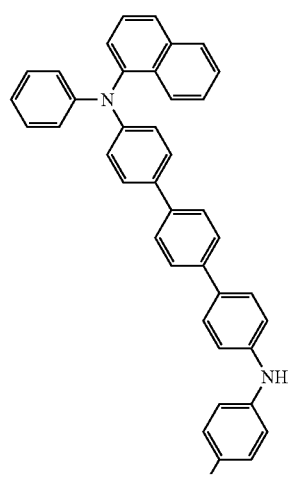 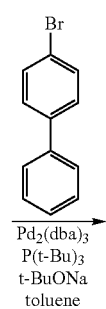 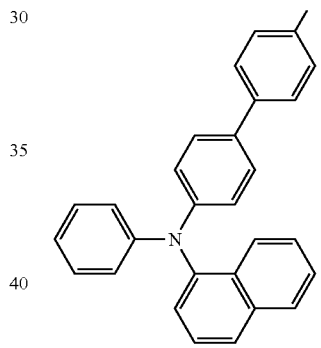

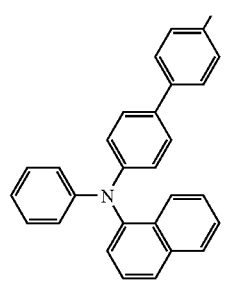

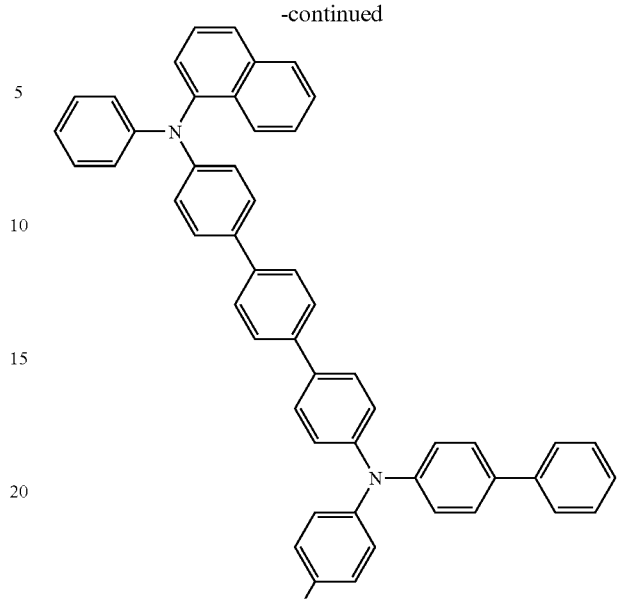

14

The compound 14 was synthesized by the same method, except that in Synthetic Example 5, 4-bromobiphenyl was used in place of 1-bromonaphthalene. This compound was analyzed by a mass spectrum to result in finding that it was the targeted product and that m/e was 1059 versus a molecular weight of 1059.46.

Synthetic Example 15

Synthesis of Aromatic Triamine Compound 15

The compound 15 was synthesized by the same method, except that in Synthetic Example 1, N-phenyl-2-naphthylamine was used in place of N,N-diphenylamine. This compound was analyzed by a mass spectrum to result in finding that it was the targeted product and that m/e was 983 versus a molecular weight of 983.42.

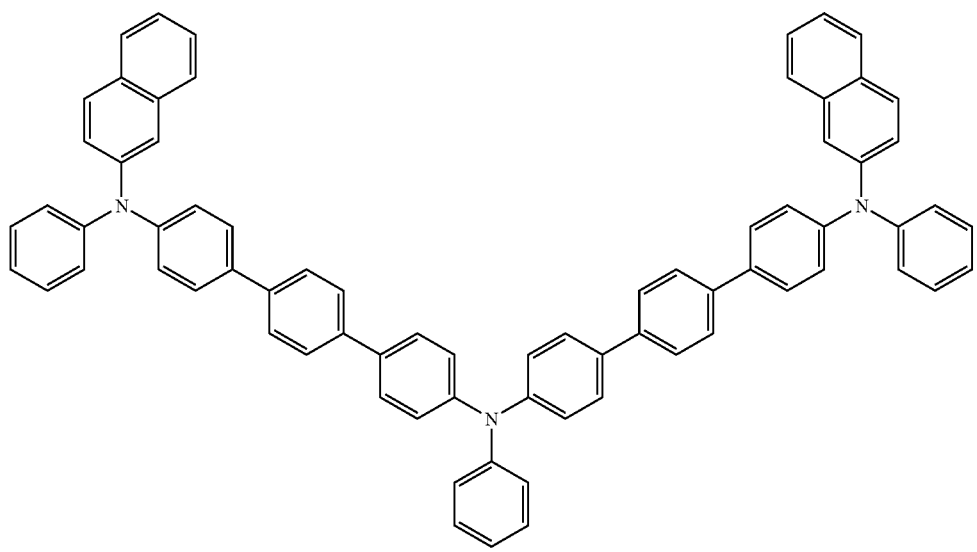
15
Synthetic Example 16
Synthesis of Aromatic Triamine Compound 16
The compound 16 was synthesized by the same method, except that in Synthetic Example 6, 2-bromonaphthalene was used in place of 1-bromonaphthalene. This compound was analyzed by a mass spectrum to result in finding that it was the targeted product and that m/e was 933 versus a molecular weight of 933.41.
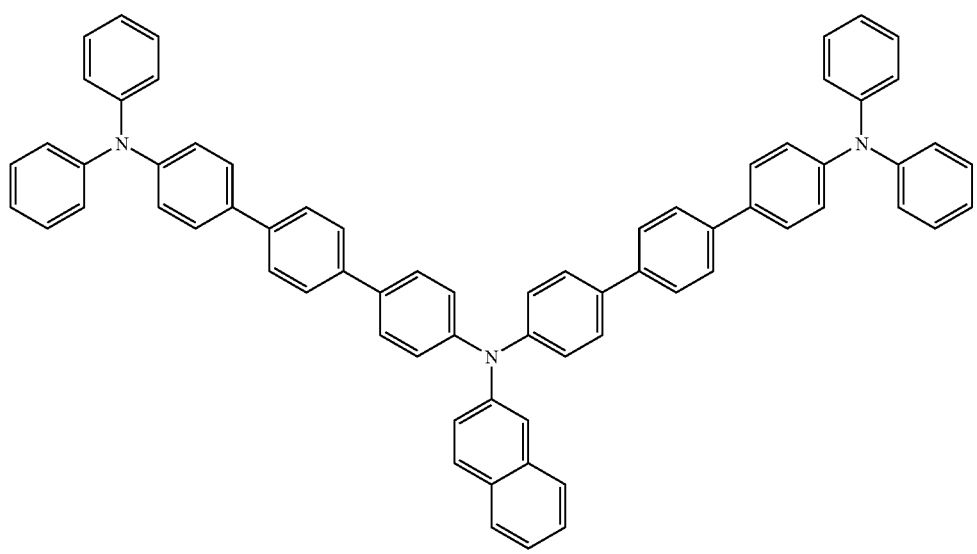
16

Synthetic Example 17
Synthesis of Aromatic Triamine Compound 17
The following compound 17 was synthesized by the following reaction process:
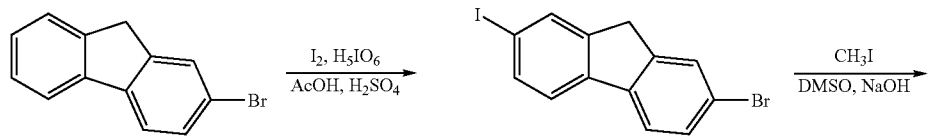
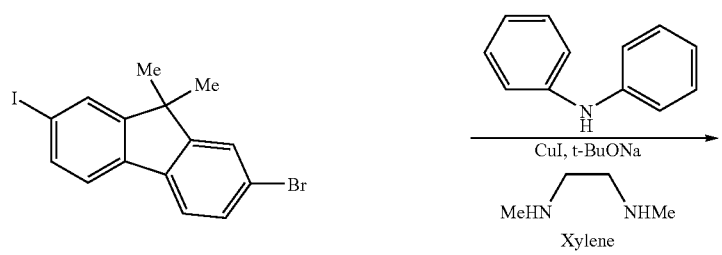
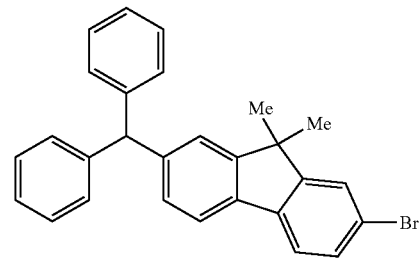
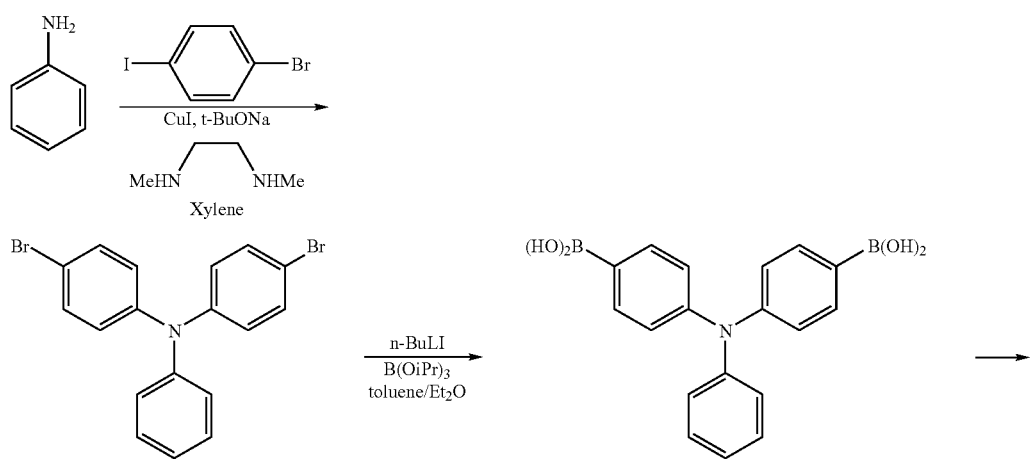

-continued

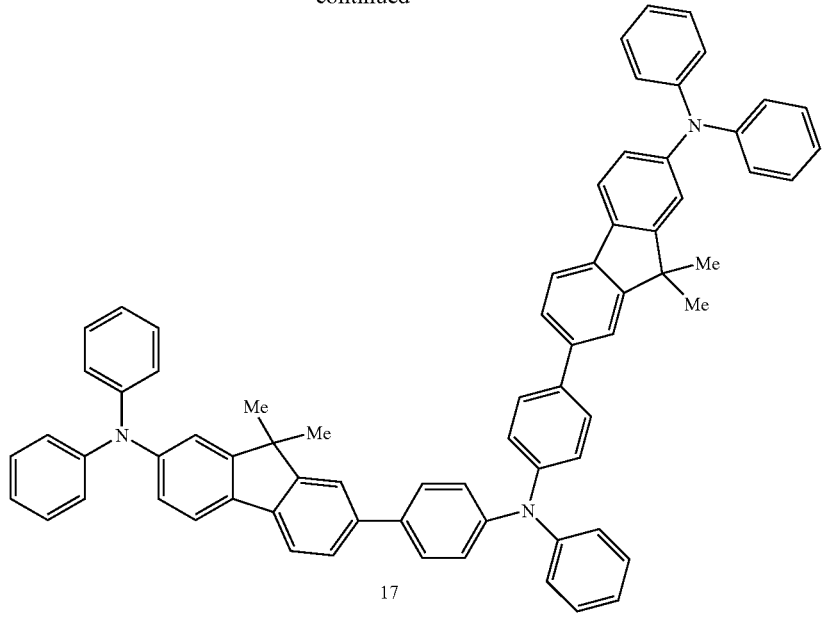

17

(1) Synthesis of 2-bromo-7-iodofluorene

Charged were 2-bromofluorene 25.0 g, iodine 11.5 g, orthoperiodic acid 4.88 g, acetic acid 150 ml, conc. sulfuric acid 3 ml and water 10 ml, and the mixture was heated at 60° C. for 30 minutes while stirring. Further, the temperature was elevated up to 90° C., and the mixture was heated for 3 hours while stirring. The reaction solution was left cooling down to room temperature and poured into 500 ml of water. The precipitate formed was filtered and washed with ethanol and water. The solid matter thus obtained was recrystallized from ethanol to obtain 26.5 g of yellow crystal of 2-bromo-7-iodofluorene.

(2) Synthesis of 2-bromo-7-iodo-9,9-dimethylfluorene

A reaction vessel was charged with 2-bromo-7-iodofluorene 26.5 g, dimethylsulfoxide (DMSO) 100 ml, benzyltriethylammonium chloride 0.500 g and a sodium hydroxide aqueous solution 100 g of 50% by weight under Ar atmosphere.

This reaction vessel was put in a water bath, and methyl iodide 22.3 g was added thereto.

After carrying out reaction for 5 hours, 500 ml of water was added thereto, and the resulting precipitate was filtered. The solid matter obtained was washed with water and methanol to obtain 20.0 g of yellow crystal of 2-bromo-7-iodo-9,9-dimethylfluorene.

(3) Synthesis of 2-(N,N-diphenylamino)-7-bromo-9,9-dimethylfluorene

Charged under Ar atmosphere were 2-bromo-7-iodo-9,9-dimethylfluorene 20.0 g, diphenylamine 8.46 g, copper iodide 0.476 g, N,N'-dimethylethylene-diamine 0.441 g, sodium t-butoxide 7.21 g and xylene 50 ml, and the mixture was refluxed for 24 hours under heating. After cooled down to room temperature, the mixture was extracted with toluene, and the insoluble matter was filtered. The filtrate was concentrated, and then the concentrate was refined by silica gel chromatography to obtain 15.4 g of a yellow solid matter of 2-(N,N-diphenylamino)-7-bromo-9,9-dimethylfluorene.

(4) Synthesis of 4,4'-dibromotriphenylamine

Charged under Ar atmosphere were bromoiodobenzene 62.2 g, aniline 9.31 g, copper iodide 1.90 g, N,N'-dimethylethylenediamine 1.76 g, sodium t-butoxide 28.8 g and xylene 200 ml, and the mixture was refluxed for 24 hours under heating. After cooled down to room temperature, the mixture was extracted with toluene, and the insoluble matter was filtered. The filtrate was concentrated, and then the concentrate was refined by silica gel chromatography to obtain 20.1 g of a white solid matter of 4,4'-dibromotriphenylamine.

(5) Synthesis of triphenylamine-4,4'-bisboronic acid

A dry ethyl ether 200 ml and dry toluene 200 ml solution of 4,4'-dibromotriphenylamine 20.0 g was cooled down to −78° C. under argon atmosphere, and a hexane solution 66 ml of 1.6M normal butyllithium was dropwise added thereto. The reaction solution was stirred for one hour while heating up to 0° C. The reaction solution was cooled down again to −78° C., and a dry ether 100 ml solution of triisopropyl borate 47.0 g was dropwise added thereto. The reaction solution was stirred at room temperature for 5 hours. 1N hydrochloric acid 200 ml was added thereto and stirred for one hour, and then the aqueous layer was removed. The organic layer was dried on magnesium sulfate, and the solvent was distilled off. The solid matter thus obtained was washed with hexane and toluene to obtain 8.32 g of white powder of triphenylamine-4,4'-bisboronic acid.

(6) Synthesis of Compound 17

Charged under Ar atmosphere were 2-(N,N-diphenylamino)-7-bromo-9,9-dimethylfluorene 9.68 g, triphenylamine-4,4'-bisboronic acid 3.33 g, tetrakis(triphenylphosphine)palladium (0) 231 mg, toluene 60 ml and a 2M sodium carbonate aqueous solution 30 ml, and the mixture was refluxed for 8 hours under heating. After finishing the reaction, the reaction solution was filtered. The solid matter thus obtained was washed with water and methanol and then recrystallized from toluene to obtain 5.02 g of pale yellow crystal. This compound was analyzed by a mass spectrum to result in finding that it was the targeted product and that m/e was 963 versus a molecular weight of 963.46.

Synthetic Example 18
Synthesis of Aromatic Triamine Compound 18
The following compound 18 was synthesized by the following reaction process:
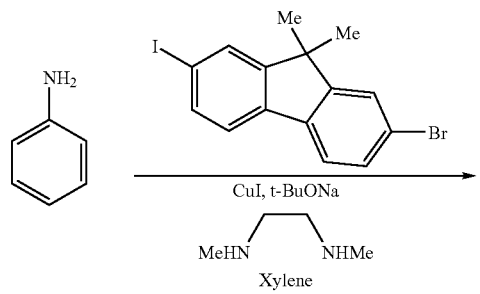
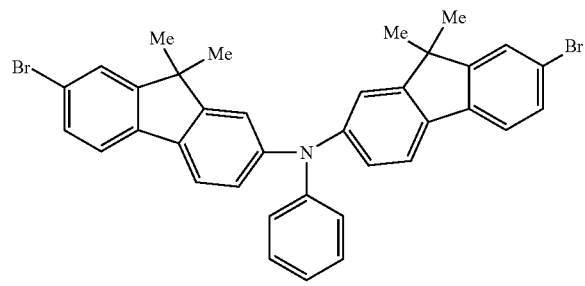
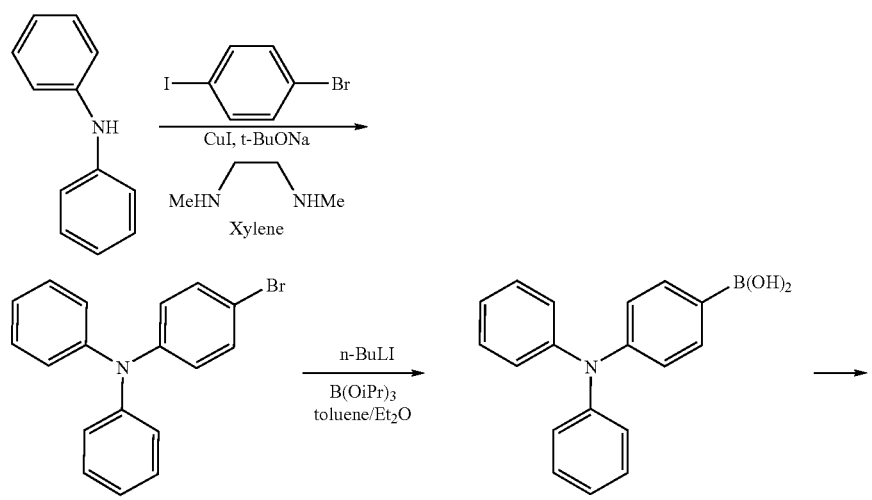

-continued

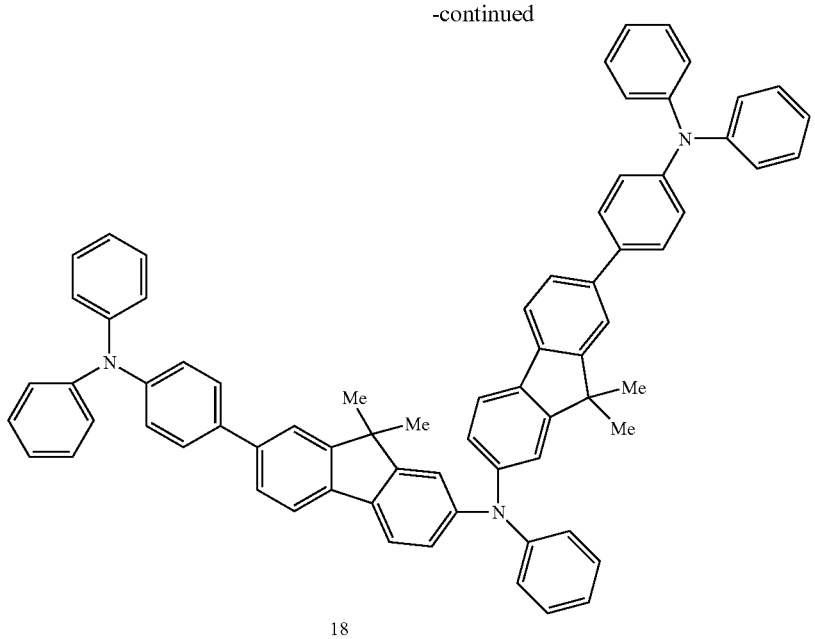

18

(1) Synthesis of 4-bromotriphenylamine

N,N'-dimethylethylenediamine 1.76 g was added to diphenylamine 16.9 g, 4-bromoiodobenzene 28.2 g sodium t-butoxide 14.4 g, copper powder 3.81 g and a xylene 100 ml solution, and the mixture was heated and refluxed for 24 hours under argon atmosphere. After cooled down to room temperature, the mixture was filtered to remove an insoluble matter, and the filtrate was concentrated. The residue was refined by silica gel chromatography to obtain 22.7 g of white crystal of 4-bromotriphenylamine.

(2) Synthesis of triphenylamine-4-boronic acid

A dry ethyl ether 100 ml and dry toluene 100 ml solution of 4-bromotriphenylamine 16.2 g was cooled down to −78° C. under argon atmosphere, and a hexane solution 32.8 ml of 1.6M normal butyllithium was dropwise added thereto. The reaction solution was stirred for one hour while heating up to 0° C. The reaction solution was cooled down again to −78° C., and a dry ether 50 ml solution of triisopropyl borate 23.5 g was dropwise added thereto. The reaction solution was stirred at room temperature for 5 hours. 1N hydrochloric acid 100 ml was added thereto and stirred for one hour, and then the aqueous layer was removed. The organic layer was dried on magnesium sulfate, and the solvent was distilled off. The solid matter thus obtained was washed with hexane and toluene to obtain 10.2 g of triphenylamine-4-boronic acid.

(3) Synthesis of N,N-bis(7-bromo-9,9-dimethylfluorene-2-yl)aniline

Charged under Ar atmosphere were bromoiodobenzene 80.0 g, aniline 9.31 g, copper iodide 1.90 g, N,N'-dimethylethylenediamine 1.76 g, sodium t-butoxide 28.8 g and xylene 200 ml, and the mixture was refluxed for 24 hours under heating. After cooled down to room temperature, the mixture was extracted with toluene, and the insoluble matter was filtered. The filtrate was concentrated, and then the concentrate was refined by silica gel chromatography to obtain 20.1 g of a pale yellow solid matter of N,N-bis(7-bromo-9,9-dimethylfluorene-2-yl)aniline.

(4) Synthesis of Compound 15

Charged under Ar atmosphere were N,N-bis(7-bromo-9,9-dimethylfluorene-2-yl)aniline 6.35 g, triphenylamine-4-boronic acid 6.36 g, tetrakis(triphenylphosphine)palladium (0) 462 mg, toluene 80 ml and a 2M sodium carbonate aqueous solution 40 ml, and the mixture was refluxed for 8 hours under heating. After finishing the reaction, the mixture was filtered. The solid matter thus obtained was washed with water and methanol and recrystallized from toluene to obtain 5.12 g of pale yellow crystal. This compound was analyzed by a mass spectrum to result in finding that it was the targeted product and that m/e was 963 versus a molecular weight of 963.46.

Example 1

Production of Organic EL Device

A glass substrate (manufactured by Geomatec Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes. The glass substrate equipped with an ITO transparent electrode line after washing was mounted on a substrate holder of a vacuum depositing apparatus, and a compound 1 film having a film thickness of 80 nm was formed by resistance heating deposition on a face at a side on which the transparent electrode line was formed so that the transparent electrode described above was covered. This compound 1 film functions as a hole injecting and transporting layer. Next, a 9-(2-naphthyl)-10-[4-(1-naphthyl)-phenyl] anthracene (hereinafter abbreviated as AN-1) film was formed on the above compound 1 film in a film thickness of 40 nm by resistance heating deposition. Then, the following compound D-1 having a styryl group was deposited as a luminescent molecule at the same time as above at a weight ratio of 2:40 to AN-1. This film functions as a luminescent layer. An Alq film having a film thickness of 10 nm was formed on the above film. This Alq film functions as an electron injecting layer. Thereafter, Li (Li source: manufactured by Saes Getters Co., Ltd.) which was a reducing dopant and Alq were subjected to binary deposition to form an Alq:Li film (film thickness: 10 nm) as an electron injecting layer (cathode). Metal Al was deposited on the above Alq:Li film to form a metal cathode, whereby an organic EL device was produced.

Shown in Table 1 are results obtained by measuring an electric current density in applying an electric current to the device thus obtained at a voltage of 5 V and a luminous efficiency at a luminance of 100 cd/m² and a luminescent color. Further, shown in Table 1 is a half life (hour) in driving this device in a constant electric current at an initial luminance of 1000 cd/m². Also, a glass transition temperature (Tg) of the compound 1 used for the hole injecting and transporting layer is shown in Table 1.

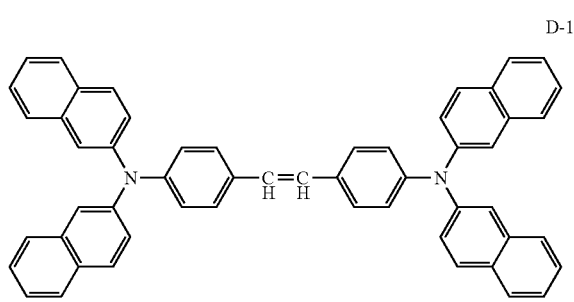

D-1

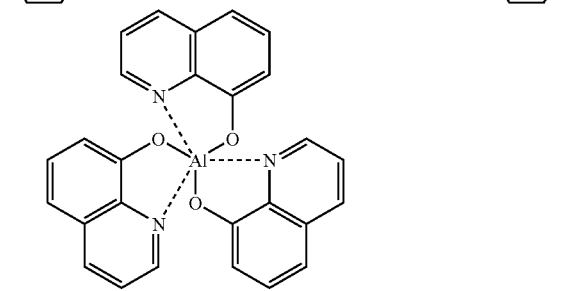

Alq

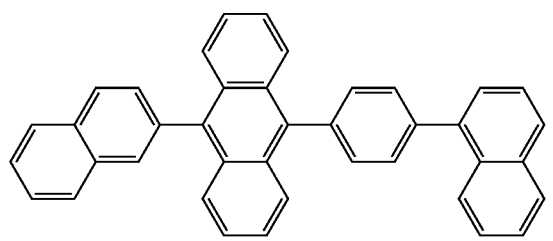

AN-1

Examples 2 to 12

Organic EL devices were prepared in the same manner, except that in Example 1, compounds shown in Table 1 were used in place of the compound 1 as the material for forming the hole injecting and transporting layer.

Shown in Table 1 are results obtained by measuring an electric current density in applying an electric current to the devices thus obtained at a voltage of 5 V and a luminous efficiency at a luminance of 100 cd/m² and a luminescent color. Further, shown in Table 1 is a half life (hour) in driving this device in a constant electric current at an initial luminance of 1000 cd/m². Also, Tg's of the respective compounds used for the hole injecting and transporting layer are shown in Table 1.

Comparative Examples 1 to 5

Organic EL devices were prepared in the same manner, except that in Example 1, the following compounds (A) to (E) shown in Table 1 were used in place of the compound 1 as the material for forming the hole injecting and transporting layer.

Shown in Table 1 are results obtained by measuring an electric current density in applying an electric current to the devices thus obtained at a voltage of 5 V and a luminous efficiency at a luminance of 100 cd/m² and a luminescent color. Further, shown in Table 1 is a half life (hour) in driving this device in a constant electric current at an initial luminance of 1000 cd/m². Also, Tg's of the respective compounds used for the hole injecting and transporting layer are shown in Table 1.

TABLE 1

| | Material of hole injecting & transporting layer | Current density (mA/cm²) @5 V | Luminous efficiency (cd/A) @100 cd/m² | Luminescent color | Half life (hour) @1000 cd/m² | Tg (° C.) |
|---|---|---|---|---|---|---|
| Example 1 | Compound 1 | 3.26 | 6.4 | Blue | 3500 | 125 |
| Example 2 | Compound 2 | 3.31 | 6.5 | Blue | 5200 | 135 |
| Example 3 | Compound 3 | 4.26 | 6.6 | Blue | 5000 | 140 |
| Example 4 | Compound 4 | 3.35 | 6.4 | Blue | 5600 | 135 |
| Example 5 | Compound 5 | 3.12 | 6.8 | Blue | 5500 | 156 |
| Example 6 | Compound 6 | 3.41 | 6.3 | Blue | 5800 | 121 |
| Example 7 | Compound 7 | 3.24 | 6.4 | Blue | 5800 | 120 |

TABLE 1-continued

| | Material of hole injecting & transporting layer | Current density (mA/cm$^2$) @5 V | Luminous efficiency (cd/A) @100 cd/m$^2$ | Luminescent color | Half life (hour) @1000 cd/m$^2$ | Tg (° C.) |
|---|---|---|---|---|---|---|
| Example 8 | Compound 8 | 3.67 | 6.7 | Blue | 7400 | 115 |
| Example 9 | Compound 9 | 3.56 | 6.6 | Blue | 7800 | 125 |
| Example 10 | Compound 12 | 3.61 | 6.6 | Blue | 7700 | 120 |
| Example 11 | Compound 13 | 3.27 | 6.4 | Blue | 5600 | 135 |
| Example 12 | Compound 14 | 3.22 | 6.5 | Blue | 5800 | 140 |
| Comparative Example 1 | Compound (A) | 2.43 | 5.9 | Blue | 2000 | 110 |
| Comparative Example 2 | Compound (B) | 2.32 | 5.8 | Blue | 2300 | 100 |
| Comparative Example 3 | Compound (C) | 1.51 | 5.1 | Blue | 1800 | 126 |
| Comparative Example 4 | Compound (D) | 1.43 | 4.8 | Blue | 1500 | 115 |
| Comparative Example 5 | Compound (E) | 1.11 | 3.8 | Blue | 1000 | 95 |

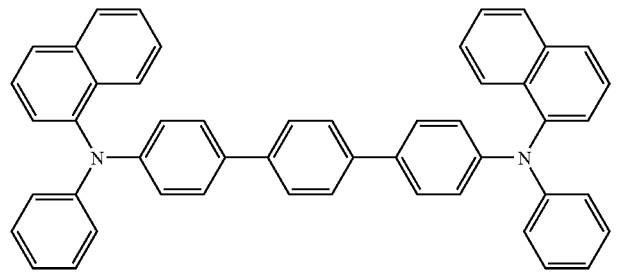

(A)

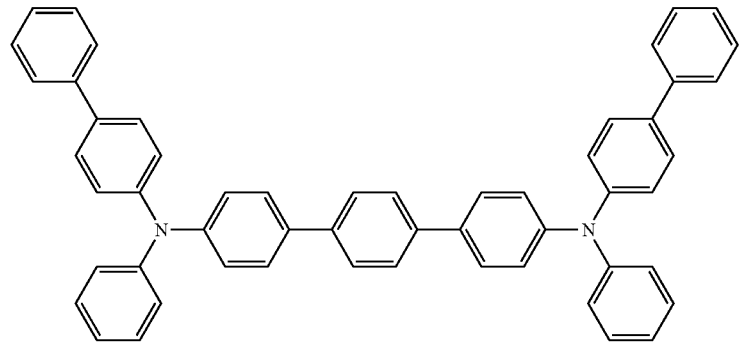

(B)

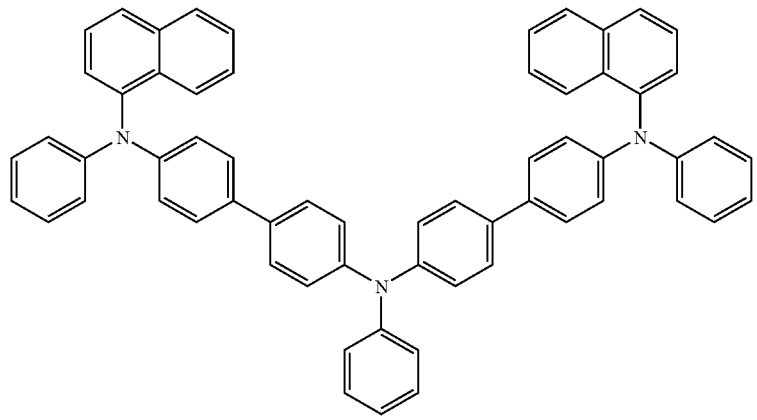

(C)

TABLE 1-continued

| Material of hole injecting & transporting layer | Current density (mA/cm$^2$) @5 V | Luminous efficiency (cd/A) @100 cd/m$^2$ | Luminescent color | Half life (hour) @1000 cd/m$^2$ | Tg (° C.) |
| --- | --- | --- | --- | --- | --- |

(D)

(E)

As shown in Table 1, the organic EL devices in which the compounds of the present invention are used for the hole injecting and transporting layer have a long life and a high hole injecting property and therefore have a high luminous efficiency.

Example 13

Production of Organic EL Device

A glass substrate (manufactured by Geomatec Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes. The glass substrate equipped with an ITO transparent electrode line after washing was mounted on a substrate holder of a vacuum depositing apparatus, and a compound 1 film having a film thickness of 60 nm was formed by resistance heating deposition on a face at a side on which the transparent electrode line was formed so that the transparent electrode described above was covered. This compound 1 film functions as a hole injecting layer. Next, a 4,4'-bis[N-(1-naphthyl)-N-phenylamino]biphenyl film (hereinafter abbreviated as an "NPD film") having a film thickness of 20 nm was formed as a hole transporting material on the above compound 1 film by resistance heating deposition. This NPD film functions as a hole transporting layer. Further, an AN-1 film was formed in a film thickness of 40 nm on the above NPD film by resistance heating deposition. Then, an amine compound D-1 was deposited as a luminescent molecule at the same time as above at a weight ratio of 2:40 to AN-1. This film functions as a luminescent layer. An Alq film having a film thickness of 10 nm was formed on the above film. This Alq film functions as an electron injecting layer. Thereafter, Li (Li source: manufactured by Saes Getters Co., Ltd.) which was a reducing dopant and Alq were subjected to binary deposition to form an Alq:Li film (film thickness: 10 nm) as an electron injecting layer (cathode). Metal Al was deposited on the above Alq:Li film to form a metal cathode, whereby an organic EL device was produced.

Shown in Table 2 are results obtained by measuring an electric current density in applying an electric current to the device thus obtained at a voltage of 5 V and a luminous efficiency at a luminance of 100 cd/m$^2$ and a luminescent color. Further, shown in Table 2 is a half life (hour) in driving this device in a constant electric current at an initial luminance of 1000 cd/m$^2$. Also, Tg of the compound 1 used for the hole injecting layer is shown in Table 2.

Examples 14 to 27

Organic EL devices were prepared in the same manner, except that in Example 13, compounds shown in Table 2 were used in place of the compound 1 as the material for forming the hole injecting layer.

Shown in Table 2 are results obtained by measuring an electric current density in applying an electric current to the devices thus obtained at a voltage of 5 V and a luminous efficiency at a luminance of 100 cd/m² and a luminescent color. Further, shown in Table 2 is a half life (hour) in driving this device in a constant electric current at an initial luminance of 1000 cd/m². Also, Tg's of the respective compounds used for the hole injecting layer are shown in Table 2.

Comparative Examples 6 to 10

Organic EL devices were prepared in the same manner, except that in Example 13, the compounds (A) to (E) described above shown in Table 2 were used in place of the compound 1 as the material for forming the hole injecting layer.

Shown in Table 2 are results obtained by measuring an electric current density in applying an electric current to the devices thus obtained at a voltage of 5 V and a luminous efficiency at a luminance of 100 cd/m² and a luminescent color. Further, shown in Table 2 is a half life (hour) in driving this device in a constant electric current at an initial luminance of 1000 cd/m². Also, Tg's of the respective compounds used for the hole injecting layer are shown in Table 2.

INDUSTRIAL APPLICABILITY

As explained above in details, the organic EL devices using the aromatic triamine compounds of the present invention are excellent in a hole injecting property and have a high luminous efficiency and a long life. Accordingly, the organic EL devices of the present invention have a high practical use and are useful as light sources for plain luminants of wall-mounted televisions and backlights for displays.

What is claimed is:

1. An aromatic triamine compound represented by the following Formula (1):

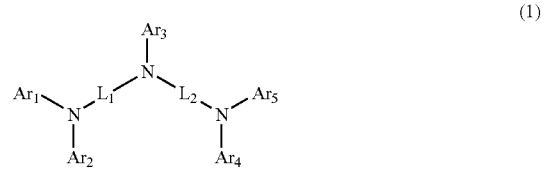

wherein $Ar_1$ to $Ar_5$ each are independently a substituted or unsubstituted aryl group having 6 to 30 nuclear carbon atoms;
$L_1$ and $L_2$ each are independently a linkage group having 6 to 30 nuclear carbon atoms which has one or more benzene rings, and one of $L_1$ and $L_2$ is a substituted or unsubstituted terphenylene group,

TABLE 2

| | Material of hole injecting layer | Current density (mA/cm²) @ 5 V | Luminous efficiency (cd/A) @ 100 cd/m² | Luminescent color | Half life (hour) @ 1000 cd/m² | Tg (° C.) |
|---|---|---|---|---|---|---|
| Example 13 | Compound 1 | 2.60 | 6.5 | Blue | 10000 | 125 |
| Example 14 | Compound 2 | 2.60 | 6.4 | Blue | 10000 | 135 |
| Example 15 | Compound 3 | 2.61 | 6.0 | Blue | 10000 | 140 |
| Example 16 | Compound 4 | 2.48 | 6.9 | Blue | 7000 | 135 |
| Example 17 | Compound 5 | 2.61 | 6.5 | Blue | 10000 | 156 |
| Example 18 | Compound 6 | 2.60 | 6.5 | Blue | 10000 | 121 |
| Example 19 | Compound 7 | 2.59 | 6.5 | Blue | 10000 | 120 |
| Example 20 | Compound 8 | 2.51 | 6.9 | Blue | 7000 | 115 |
| Example 21 | Compound 9 | 2.50 | 6.9 | Blue | 7000 | 125 |
| Example 22 | Compound 10 | 2.36 | 6.4 | Blue | 5500 | 110 |
| Example 23 | Compound 11 | 2.42 | 6.5 | Blue | 5200 | 125 |
| Example 24 | Compound 15 | 2.60 | 6.5 | Blue | 10000 | 140 |
| Example 25 | Compound 16 | 2.60 | 6.5 | Blue | 10000 | 140 |
| Example 26 | Compound 17 | 2.56 | 6.8 | Blue | 9000 | 135 |
| Example 27 | Compound 18 | 2.58 | 6.8 | Blue | 9000 | 135 |
| Comparative Example 6 | Compound (A) | 2.12 | 4.5 | Blue | 2300 | 110 |
| Comparative Example 7 | Compound (B) | 2.22 | 4.6 | Blue | 2500 | 100 |
| Comparative Example 8 | Compound (C) | 2.01 | 4.5 | Blue | 1800 | 126 |
| Comparative Example 9 | Compound (D) | 2.03 | 4.6 | Blue | 1600 | 115 |
| Comparative Example 10 | Compound (E) | 2.24 | 5.2 | Blue | 2000 | 95 |

As shown in Table 2, the organic EL devices in which the compounds of the present invention are used for the hole injecting layer have a long life and a high hole injecting property and therefore have a high luminous efficiency.

wherein one of $L_1$ and $L_2$ is not a terphenylene group, and wherein the linkage group of $L_1$ or $L_2$ that is not a terphenylene group is a group represented by the following Formula (2):

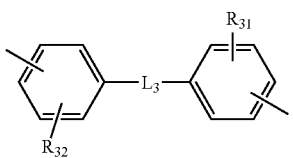
(2)

wherein $L_3$ is a hetero atom, a substituted or unsubstituted alkylene group having 1 to 6 carbon atoms, a substituted or unsubstituted cycloalkylene group having 3 to 30 carbon atoms, a substituted or unsubstituted arylene group having 6 to 30 nuclear carbon atoms, wherein the substituted or unsubstituted arylene group does not comprise 6 nuclear carbon atoms, or a substituted or unsubstituted heteroarylene group having 5 to 30 nuclear carbon atoms;

$R_{31}$, and $R_{32}$ each are independently a hydrogen atom, a substituted or unsubstituted alkyl group having 1 to 6 carbon atoms, a substituted or unsubstituted cycloalkyl group having 3 to 30 carbon atoms or a substituted or unsubstituted aryl group having 6 to 30 nuclear carbon atoms; $R_{31}$ and $R_{32}$ described above each may be plural, and in such case, plural $R_{31}$ themselves and $R_{32}$ themselves may be combined with each other to form saturated or unsaturated rings.

2. The aromatic triamine compound as described in claim 1, wherein the linkage group of $L_1$ or $L_2$ described above a group represented by the following Formula (3):

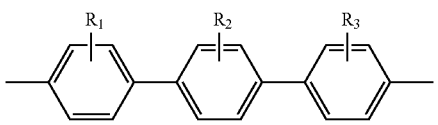
(3)

wherein $R_1$, $R_2$ and $R_3$ each are independently a hydrogen atom, a substituted or unsubstituted alkyl group having 1 to 6 carbon atoms, a substituted or unsubstituted cycloalkyl group having 3 to 30 carbon atoms or a substituted or unsubstituted aryl group having 6 to 30 nuclear carbon atoms; $R_1$, $R_2$ and $R_3$ each may be plural; in such case, $R_1$ themselves, $R_2$ themselves and $R_3$ themselves may be combined with each other to form saturated or unsaturated rings; $R_1$ and $R_2$, and $R_2$ and $R_3$ may be combined with each other to form a saturated or unsaturated ring.

3. An organic electroluminescence device in which an organic thin film layer comprising a single layer or plural layers having at least a luminescent layer is interposed between a cathode and an anode, wherein at least one layer of the above organic thin film layers contains the aromatic triamine compound as described in claim 1 in the form of a single component or a mixed component.

4. The organic electroluminescence device as described in claim 3, wherein the organic thin film layer described above has a hole transporting zone and/or a hole injecting zone, and the aromatic triamine derivative described above is contained in the above hole transporting zone and/or the hole injecting zone.

5. The organic electroluminescence device as described in claim 3, wherein the organic thin film layer described above has a hole transporting layer and/or a hole injecting layer, and the aromatic triamine compound described above is contained in the above hole transporting layer and/or the hole injecting layer.

6. The organic electroluminescence device as described in claim 3, wherein blue color is emitted.

* * * * *